United States Patent
Röder et al.

(10) Patent No.: US 9,211,314 B2
(45) Date of Patent: Dec. 15, 2015

(54) TREATMENT SELECTION FOR LUNG CANCER PATIENTS USING MASS SPECTRUM OF BLOOD-BASED SAMPLE

(71) Applicant: Biodesix, Inc., Boulder, CO (US)

(72) Inventors: Heinrich Röder, Steamboat Springs, CO (US); Joanna Röder, Steamboat Springs, CO (US)

(73) Assignee: Biodesix, Inc., Boulder, CO (US)

( * ) Notice: Subject to any disclaimer, the term of this patent is extended or adjusted under 35 U.S.C. 154(b) by 0 days.

(21) Appl. No.: 14/460,769

(22) Filed: Aug. 15, 2014

(65) Prior Publication Data

US 2015/0283206 A1 Oct. 8, 2015

Related U.S. Application Data

(60) Provisional application No. 61/975,267, filed on Apr. 4, 2014.

(51) Int. Cl.
| | |
|---|---|
| *G01N 33/48* | (2006.01) |
| *A61K 38/17* | (2006.01) |
| *H01J 49/26* | (2006.01) |
| *H01J 49/00* | (2006.01) |
| *G01N 33/49* | (2006.01) |
| *G06F 19/24* | (2011.01) |

(52) U.S. Cl.
CPC .............. *A61K 38/179* (2013.01); *G01N 33/49* (2013.01); *G06F 19/24* (2013.01); *H01J 49/0036* (2013.01); *H01J 49/26* (2013.01)

(58) Field of Classification Search
CPC ..................................................... G06F 19/24
USPC .......................................................... 702/19
See application file for complete search history.

(56) References Cited

U.S. PATENT DOCUMENTS

| | | |
|---|---|---|
| 7,294,468 B2 | 11/2007 | Bell |
| 7,736,905 B2 | 6/2010 | Röder |
| 7,858,380 B2 | 12/2010 | Baker |
| 7,858,389 B2 | 12/2010 | Röder |
| 7,867,774 B2 | 1/2011 | Lugade |
| 8,148,076 B2 | 4/2012 | Baker |
| 8,467,988 B1 | 6/2013 | Röder |
| 2005/0048547 A1 | 3/2005 | Zhao |
| 2005/0164218 A1 | 7/2005 | Agus |
| 2006/0029574 A1 | 2/2006 | Albitar |
| 2011/0208433 A1 | 8/2011 | Grigorieva |
| 2013/0320203 A1 | 12/2013 | Röder |

FOREIGN PATENT DOCUMENTS

| | | |
|---|---|---|
| EP | 2251044 A1 | 11/2010 |
| WO | 2005/098445 | 10/2005 |

OTHER PUBLICATIONS

Elkan, "Maximum Likelihood, Logistic Regression, and Stochastic Gradient Training", elkan@cs.ucsd.edu, (2013).
Wager et al., "Dropout Training as Adaptive Regularization", arXiv:1307.1493[stat.ML] (2013).
Hinton et al., "Improving neural networks by preventing co-adaptation of feature detectors", arXiv:1307.1493[stat.ML] (2012).
Wang et al., "Fast "dropout" training for logistic regression"; Neural Information Processing Systems 2012 Workshop on Log-Linear Models.
"Logistic Regression", (2011), http://classes.engr.oregonstate.edu/eecs/winter2011/cs434/notes/Logistic-regression-7.pdf.
Wang et al., "Fast dropout training", International Conference on Machine Learning (2013).
Taguchi et al., "Mass Spectrometry to Classify Non-Small-Cell Lung Cancer Patients for Clinical Outcome after Treatment with Epidermal Growth Factor Receptor Tyrosine Kinase Inhibitors: A Multicohort Cross-Institutional Study", JNCI, 99(11):838-846 (2007).
Xiao et al., "Serum Proteomic Profiles Suggest Celecoxib-Modulated Targets and Response Predictors", Cancer Research, 64:2904-2909 (2004).
Girosi et al., "Regularization Theory and Neural Networks Architectures", Neural Computation, 7:219-269 (1995).
Tibshirani, "Regression Shrinkage and Selection via the Lasso", J.R. Statist. Soc. B, 58(1):267-288 (1996).
Tikhonov, "On the Stability of Inverse Problems", Comptes Rendus (Doklady) de l' Academie des Sciences de l'URSS, vol. XXXIX, No. 5, pp. 195-198 (1943).
Lazzari et al., "Randomized proteomic stratified phase III study of secnd-line erlotinib (E) versus chemotherapy (CT) in patients with inoperable non-small cell lung cancer (PROSE)", 2013 ASCO Annual Meeting.
Srivastava, "Improving Neural Networks with Dropout", Master Thesis submitted 2013.
Wikipedia page, "Logistic regression", Sep. 8, 2014.
Tulyakov et al., "Review of Classifier Combination Methods", Studies in Computational Intelligence, 90:361-386 (2008).
Rokach, "Ensemble-based classifiers", Artificial Intelligence Review, Kluwer Academic Publishers, 33(1-2):1-39 (2009).
International Search Report for corresponding PCT application No. PCT/US2014/051247, dated Oct. 20, 2015.

*Primary Examiner* — Jerry Lin
(74) *Attorney, Agent, or Firm* — McDonnell Boehnen Hulbert & Berghoff LLP

(57) ABSTRACT

A test for predicting whether a non-small-cell lung cancer patient is more likely to benefit from an EGFR-I as compared to chemotherapy uses a computer-implemented classifier operating on a mass spectrum of a blood-based sample obtained from the patient. The classifier makes use of a training set which includes mass spectral data from blood-based samples of other cancer patients who are members of a class of patients predicted to have overall survival benefit on EGFRI-Is, e.g., those patients testing VS Good under the test described in U.S. Pat. No. 7,736,905. This class-labeled group is further subdivided into two subsets, i.e., those patients which exhibited early (class label "early") and late (class label "late") progression of disease after administration of the EGFR-I in treatment of cancer.

30 Claims, 19 Drawing Sheets

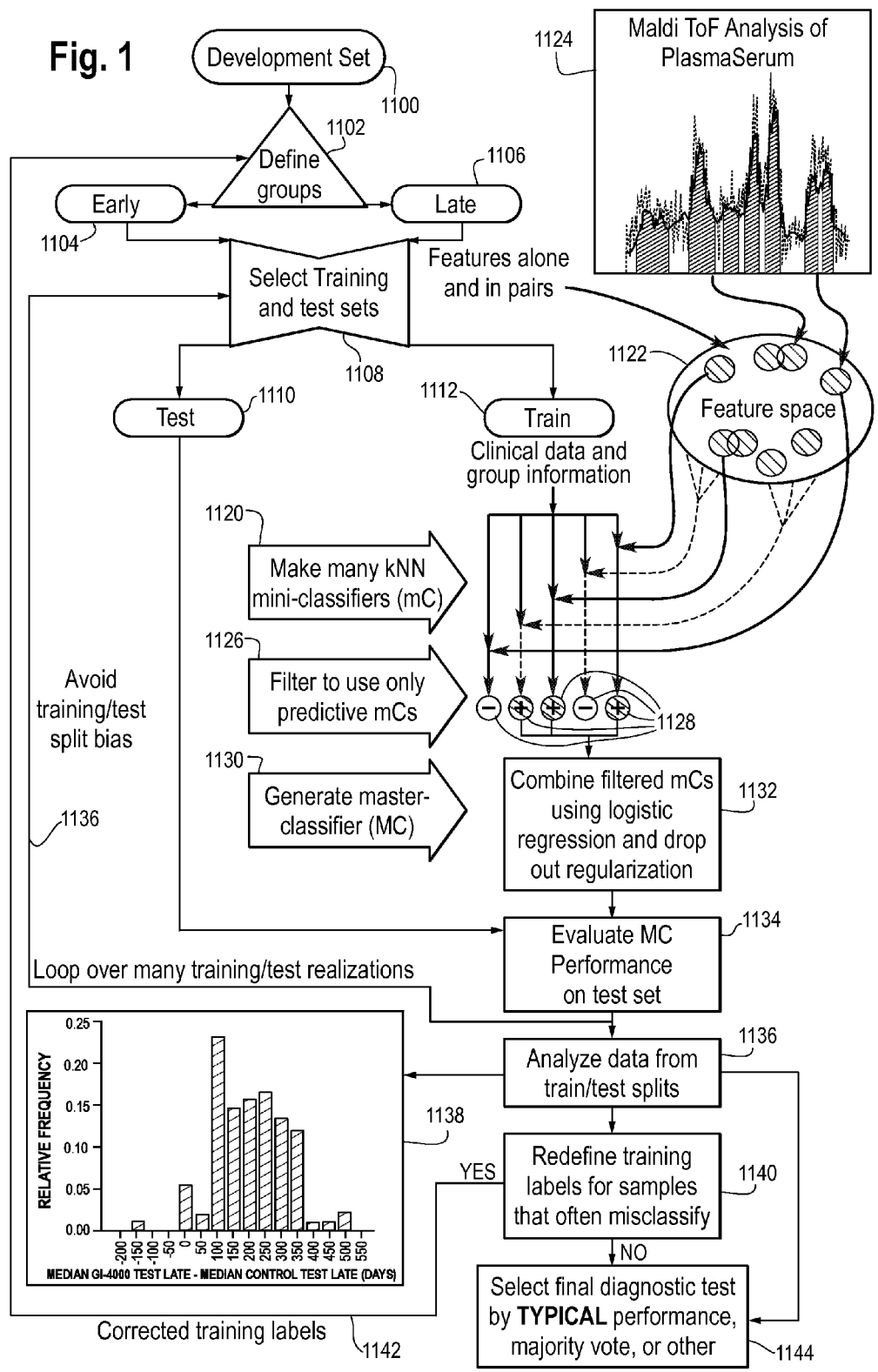

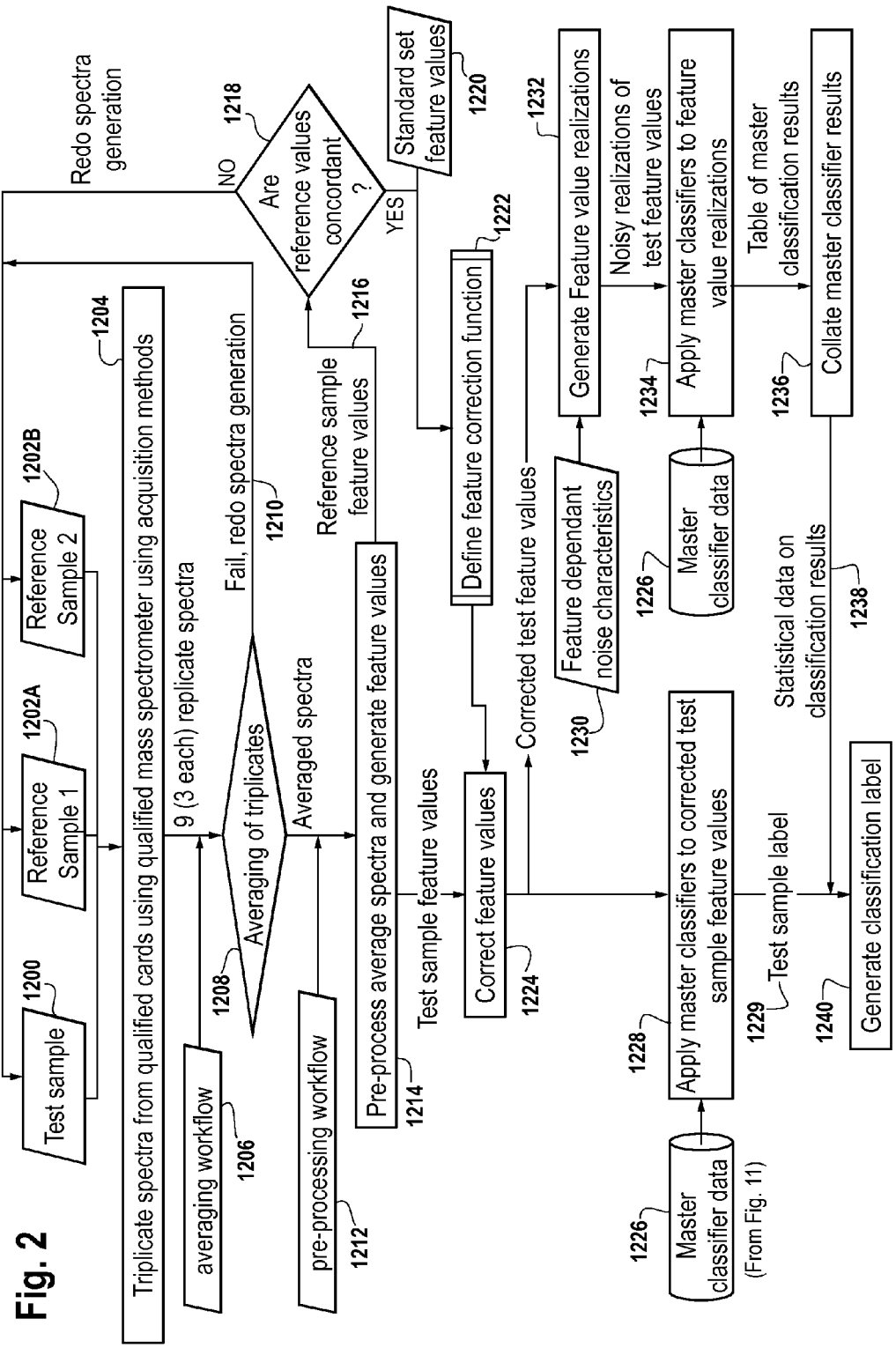

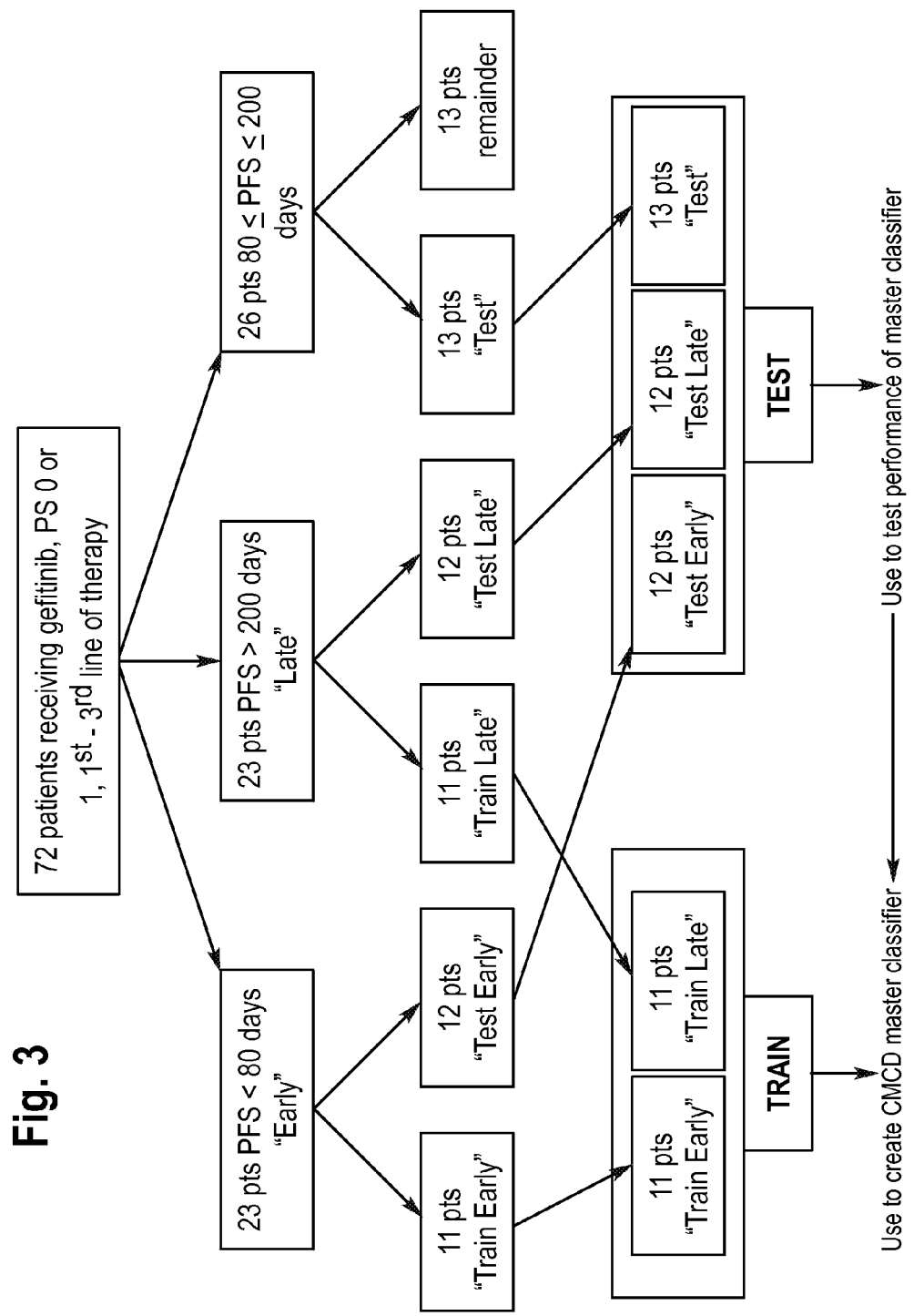

HR (95% CI): 0.67 (0.32-1.42)
log-rank p = 0.294    CPH p = 0.294
Median: Late CT:   15.1 months
        Late ERL:  17.1 months HR (95% CI): 0.93 (0.47-1.84)
log-rank p = 0.830    CPH p = 0.830
Median: Late CT:   6.1 months
        Late ERL:  3.9 months

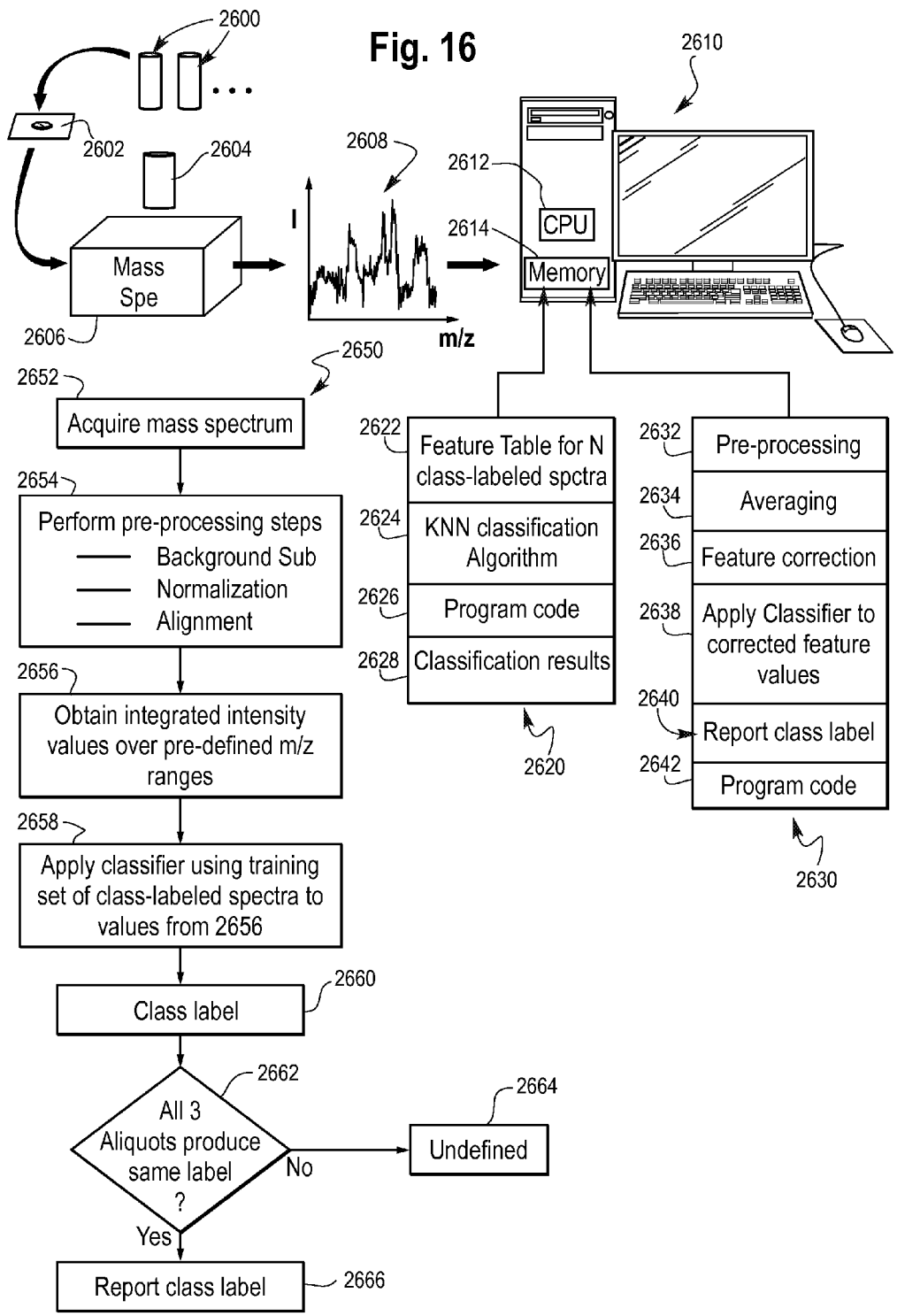

TREATMENT SELECTION FOR LUNG CANCER PATIENTS USING MASS SPECTRUM OF BLOOD-BASED SAMPLE

CROSS-REFERENCE TO RELATED APPLICATION

This application claims priority under 35 U.S.C. §119 to U.S. provisional application Ser. No. 61/975,267 filed Apr. 4, 2014, which is incorporated by reference herein.

BACKGROUND

This invention relates to the fields of biomarker discovery and personalized medicine, and more particularly relates to a method for predicting, in advance of treatment, whether a non-small-cell lung cancer (NSCLC) patient is likely to obtain more benefit from an Epidermal Growth Factor Receptor Inhibitor (EGFR-I) such as erlotinib or gefitinib as compared to chemotherapy.

Non-Small-Cell Lung Cancer is a leading cause of death from cancer in both men and women in the United States. There are at least four (4) distinct types of NSCLC, including adenocarcinoma, squamous cell, large cell, and bronchoaldeolar carcinoma. Squamous cell (epidermoid) carcinoma of the lung is a microscopic type of cancer most frequently related to smoking Adenocarcinoma of the lung accounts for over 50% of all lung cancer cases in the U.S. This cancer is more common in women and is still the most frequent type seen in non-smokers. Large cell carcinoma, especially those with neuroendocrine features, is commonly associated with spread of tumors to the brain. When NSCLC enters the blood stream, it can spread to distant sites such as the liver, bones, brain, and other places in the lung.

Treatment of NSCLC has been relatively poor over the years. Chemotherapy, the mainstay treatment of advanced cancers, is only marginally effective, with the exception of localized cancers. While surgery is the most potentially curative therapeutic option for NSCLC, it is not always possible depending on the stage of the cancer.

Recent approaches for developing anti-cancer drugs to treat the NSCLC patient focus on reducing or eliminating the ability for cancer cells to grow and divide. These anti-cancer drugs are used to disrupt the signals to the cells to tell them whether to grow or die. Normally, cell growth is tightly controlled by the signals that the cells receive. In cancer, however, this signaling goes wrong and the cells continue to grow and divide in an uncontrollable fashion, thereby forming a tumor. One of these signaling pathways begins when a chemical in the body, called epidermal growth factor, binds to a receptor that is find on the surface of many cells in the body. The receptor, known as the epidermal growth factor receptor (EGFR) sends signals to the cells, through the activation of an enzyme called tyrosine kinase (TK) that is found within the cells. The signals are used to notify cells to grow and divide.

Two EGFR-I anti-cancer drugs that were developed and prescribed to the NSCLC patients are called gefitinib (trade name "Iressa") and erlotinib (trade name "Tarceva"). These anti-cancer drugs target the EGFR pathway and have shown promise in being effective toward treating NSCLC cancer. Iressa inhibits the enzyme tyrosine kinase that is present in lung cancer cells, as well as other cancers in normal tissues, and that appears to be important to the growth of cancer cells. Iressa has been used as a single agent of the treatment of NSCLC that has progressed after, or failed to respond to, two other types of chemotherapies. There are other drugs in development and in validation that address the same EGFR pathway using different compounds, e.g. the irreversible EGFR-TKI inhibitors affatinib (Boehringer-Ingelheim) and dacomitinib (Pfizer).

The assignee of the present inventors has developed a test known as VeriStrat® which predicts whether NSCLC patients are likely or not likely to benefit from treatment of EGFR pathway targeting drugs, including gefitinib and erlotinib. The test, also referred to herein as "VS 1.0," is described in U.S. Pat. No. 7,736,905, the content of which is incorporated by reference herein. The test is also described in Taguchi F. et al., J. Nat. Cancer Institute, 2007 v. 99 (11), 838-846, the content of which is also incorporated by reference herein. Additional applications of the test are described in other patents of the present assignee, including U.S. Pat. Nos. 7,858,380; 7,858,389 and 7,867,774, the contents of which are incorporated by reference herein.

In brief, the VeriStrat test is based on serum and/or plasma samples of cancer patients. Through a combination of MALDI-TOF mass spectrometry and data analysis algorithms implemented in a computer, it compares a set of eight integrated peak intensities at predefined m/z ranges with those from a training cohort with the aid of a classification algorithm. The classification algorithm generates a class label for the patient sample: either VeriStrat "good", VeriStrat "poor", or VeriStrat "indeterminate." In multiple clinical validation studies it has been shown that patients, whose pre-treatment serum/plasma was VeriStrat "good", have significantly better outcome when treated with epidermal growth factor receptor inhibitor drugs than those patients whose sample results in a VeriStrat "poor" signature. In few cases (less than 2%) no determination can be made, resulting in a VeriStrat "indeterminate" label. VeriStrat is commercially available from Biodesix, Inc., the assignee of the present invention, and is used in treatment selection for non-small cell lung cancer patients.

The VeriStrat test was developed from analysis of a multi-institutional study of NSCLC patients treated with gefitinib. The test was developed using a training set of pre-treatment serum samples from patients who experienced either long term stable disease or early progression on gefitinib therapy. Mass spectra (MS) from these patients' serum samples were used to define 12 mass spectrometry features (i.e. spectral peaks), differentiating these two outcome groups. The test utilized eight of these features based on a k-nearest neighbors (KNN) classification scheme and its parameters optimized using additional spectra from the training cohort. The test was further qualified in a blinded fashion on the pre-treatment serum of two independent cohorts of patients who were treated with gefitinib or erlotinib. These studies confirmed that patients classified as VeriStrat Good (VSG) had better outcome than patients classified as VeriStrat Poor (VSP) (Hazard Ratio [HR] of death=0.43 P=0.004 in one cohort, HR of death=0.33 P=0.0007 in the other). The test was shown to correlate with clinical outcome following epidermal EGFR TKI therapy, but not following chemotherapy or post-surgery as there was no statistically significant difference seen in the overall survival (OS) of patients classified as VSG or VSP prior to receiving second-line chemotherapy (HR=0.74, P=0.42 in one cohort and HR=0.81, P=0.54 in another). In a third control cohort of patients with resected early-stage NSCLC, the HR for OS was 0.90 (P=0.79).

The VeriStrat test was later formally, prospectively qualified in a study known as the PROSE study. See *Randomized Proteomic Stratified Phase III Study of Second-Line Erlotinib Versus Chemotherapy in Patients with Inoperable Non-Small Cell Lung Cancer*, ClinicalTrials.gov # NCT00989690, presentation presented to 2013 ASCO conference, June 2013. In brief, PROSE was a multi-center, randomized, Phase 3 study of 285 patients with advanced NSCLC who had progressed after first line chemotherapy treatment. Patients were randomized 1:1 to receive either standard dose erlotinib or chemotherapy (docetaxel or pemetrexed at the Investigator's discretion), stratified by Eastern Cooperative Oncology Group (ECOG)-Performance Status, smoking status, and blinded pre-treatment VeriStrat classification. PROSE results confirm that patients classified as VSP have better survival on chemotherapy versus erlotinib, and that patients classified as VSG have similar OS when treated with erlotinib or chemotherapy. The study reached its primary objective of showing significant interaction between treatment outcome and VeriStrat classification with an interaction p-value of 0.031.

While the PROSE results confirm that VeriStrat is a useful test for the de-selection of erlotinib (i.e., those patients testing VSP do not obtain benefit from erlotinib and obtain better survival on chemotherapy), further review of the data indicated that a test that would identify patients likely to have superior survival on erlotinib over chemotherapy would be of additional clinical value. This unmet clinical need led to the development of a new test, described in this document, which makes this identification.

SUMMARY

In a first aspect, a method for predicting in advance of treatment whether a non-small-cell lung cancer (NSCLC) patient is a member of a class of cancer patients likely to obtain greater benefit from a treatment for the NSCLC in the form of administration of an epidermal growth factor receptor inhibitor (EGFR-I) as compared to chemotherapy, e.g., docetaxel or pemexetred. The method includes a step (a): storing in a computer readable medium non-transient data in the form of a training set comprising class-labeled mass spectral data obtained from a multitude of cancer patients who are determined by mass spectrometry of a blood-based sample to be members of a class of patients that are predicted to obtain overall survival benefit from an EGFR-I in treatment of the cancer, e.g., patients with VS 1.0 status of "Good", such class of patients further divided into two sub-classes:
1. those patients which exhibited early progression of disease after administration of the EGFR-I in treatment of cancer, mass spectral data of such patients having a class label of "early" or the equivalent; and
2. those patients which exhibited late progression of disease after administration of an EGFR-I in treatment of cancer (class label "late" or the equivalent).

The method continues with step (b): providing a blood-based sample from the NSCLC patient to a mass spectrometer and conducting mass spectrometry on the blood-based sample and thereby generating a mass spectrum for the blood-based sample.

The method continues with step (c): conducting pre-defined pre-processing steps on the mass spectrum obtained in step (b) with the aid of a programmed computer.

The method continues with step (d): obtaining integrated intensity feature values of selected features in said mass spectrum at a plurality of predefined m/z ranges after the pre-processing steps on the mass spectrum recited in step (c) have been performed.

The method continues with a step (e): executing in the programmed computer a classifier including a classification algorithm comparing the integrated intensity values obtained in step (d) with the training set stored in step (a) and responsively generating a class label for the blood-based sample. If the class label generated in step (e) is "late" or the equivalent for the mass spectrum of the blood based sample, the patient is identified as being likely to obtain greater benefit from the EGFR-I as compared to chemotherapy in treatment of the cancer.

The step (a) of storing the training set is preferably performed prior to the performance of steps (b), (c), (d) and (e). For example, a training set can be developed from a set of samples subject to mass spectroscopy, using the peak finding and other methods disclosed herein, and subject to suitable validation studies, and then stored in a computer system, portable computer medium, cloud storage or other form for later use. At the time when a given blood-based sample is to be tested and processed in accordance with steps (b)-(e) the training set is accessed and used for classification in accordance with step (e).

In one particular embodiment, the EGFR-I in the combination treatment is a small molecule EGFR tyrosine kinase inhibitor such as gefitinib or the equivalent, e.g., erlotinib. In other possible embodiments, the EGFR-Is can take the form of second generation EGFR-Is, such as dacomitinib and affitinib.

In one embodiment, the training set is in the form of class-labeled mass spectra obtained from a multitude of NSCLC patients. However, the class labelled spectra could be obtained from other types of solid epithelial tumor cancer patents, such as for example, colorectal cancer patients or SCCHN cancer patients.

In one embodiment, the classifier takes the form of a combination of filtered mini-classifiers after dropout regularization and logistical training (CMC/D classifier). Methods of generation of such a classifier from a development set of samples are described herein.

In one further embodiment, the method includes the steps of: conducting mass spectrometry of a reference sample and obtaining a set of reference sample feature values from a mass spectrum of the reference sample; checking the reference sample feature values for concordance with a predefined set of feature values; defining a feature correction function for the mass spectrum of the sample from the reference sample feature values; and correcting the feature values of the mass spectrum of the blood-based sample in accordance with the feature correction function.

In another embodiment, the method includes the steps of: a) storing a set of feature dependent noise characteristics; b) generating a set of noisy feature value realizations of the feature values of the mass spectrum of the blood-based sample; c) applying the classifier to the noisy feature value realizations and collating the results of the applying step; d) generating statistical data on the results collated in step c) and e) using the statistical data generated in step d) in conjunction with the class label generated for the sample to determine the class label for the sample.

In another aspect, a system for processing a blood-based sample of a non-small-cell lung cancer NSCLC patient to determine whether the patient is a member of a class of cancer patients likely to obtain greater benefit from a treatment for the NSCLC in the form of administration of an epidermal growth factor receptor inhibitor (EGFR-I) as compared to chemotherapy in treatment for the NSCLC. The system includes:
(a) a mass spectrometer generating a mass spectrum of the blood-based sample; and
(b) a programmed computer including a processing unit and a memory storing mass spectral data from the mass spectrometer. The memory further stores:
1) non-transient data in the form of a training set comprising class-labeled mass spectral data obtained from a multitude of cancer patients who are members of a class of patients that are predicted to obtain overall survival benefit from an EGFR-I in treatment of the cancer (e.g., those patients classified as 'Good" in the VS 1.0 test), such class of patients further divided into two sub-classes:

1. those patients which exhibited early progression of disease after administration of the EGFR-I in treatment of cancer, mass spectral data of such patients having a class label of "early" or the equivalent; and
2. those patients which exhibited late progression of disease after administration of an EGFR-I in treatment of cancer (class label "late" or the equivalent);

2) program code for implementing a classifier in the form of a combination of filtered mini-classifiers after dropout regularization and logistical training (CMC/D classifier) on the training set;

3) program code for conducting pre-defined pre-processing steps on the mass spectrum stored in 1), obtaining integrated intensity feature values of selected features in said mass spectrum at a plurality of predefined m/z ranges after the pre-processing steps on the mass spectrum have been performed; and 4) program code applying the CMC/D classifier to the integrated intensity values obtained in 3) and the training set and responsively generating a class label for the blood-based sample, wherein if the class label generated by program code 4) is "late" or the equivalent for the blood based sample the patient is identified as being likely to obtain greater benefit from the EGFR-I as compared to chemotherapy in treatment of the cancer.

In another aspect, an apparatus for use in classifying a sample is described comprising a computer memory storing non-transient data in the form of a training set comprising class-labeled mass spectral data obtained from a multitude of cancer patients who are members of a class of patients that are predicted to obtain overall survival benefit from an EGFR-I in treatment of the cancer, such class of patients further divided into two sub-classes:

1. those patients which exhibited early progression of disease after administration of the EGFR-I in treatment of cancer, mass spectral data of such patients having a class label of "early" or the equivalent; and
2. those patients which exhibited late progression of disease after administration of an EGFR-I in treatment of cancer, such patients having a class label of "late" or the equivalent.

In yet another aspect, a method of treating a NSCLC patient is disclosed, comprising the steps of: administering an EGFR-I to the NSCLC patient, wherein the patient is predicted to benefit more from the EGFR-I as compared to chemotherapy by executing in a programmed computer a classifier comparing mass spectral data produced by a mass spectrometer from a blood-based sample of the NSCLC patient to a training set comprising class-labeled mass spectral data obtained from a multitude of cancer patients who are determined by mass spectrometry of a blood-based sample to be members of a class of patients that are predicted to obtain overall survival benefit from an EGFR-I in treatment of the cancer, such class of patients further divided into two sub-classes:

1. those patients which exhibited early progression of disease after administration of the EGFR-I in treatment of cancer, mass spectral data of such patients having a class label of "early" or the equivalent; and
2. those patients which exhibited late progression of disease after administration of an EGFR-I in treatment of cancer, mass spectral data of such patients having a class label of "late" or the equivalent.

BRIEF DESCRIPTION OF THE DRAWINGS

FIG. 1 is a flow chart showing a method for generating a CMC/D classifier.

FIG. 2 is a flow chart showing a test methodology for testing a biological sample using a CMC/D classifier generated in accordance with FIG. 1.

FIG. 3 is an illustration of the initial assignment of class labels and split into training and test sets in the NSCLC/EGFR-I CMC/D classifier.

FIGS. 4A-4B are for PFS and OS for the initial class labels, whereas FIGS. 4C-4F are for PFS and OS after one or two flips of class labels for test samples frequently misclassified.

FIG. 6A shows OS for gefitinib-treated patients; FIG. 6B shows PFS for gefitinib-treated patients, FIG. 6C shows OS for chemotherapy-treated patients and FIG. 6D shows PFS for chemotherapy-treated patients

FIG. 16 is an illustration of a test sample processing system including a computer storing a classifier and training set and a mass spectrometer obtaining a mass spectrum of blood-based samples.

DETAILED DESCRIPTION

Figure 4A:
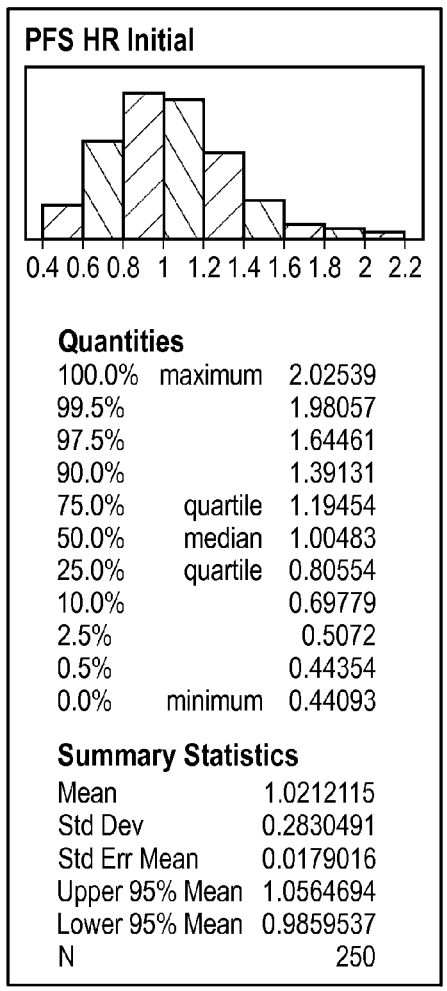
FIGS. 4A-4F are plots of the distribution of Hazard Ratios (HR) between Early and Late classification of the test sets for PFS and OS generated in the CMC/D classifier generation method (step 1134 in FIG. 1).

The following description is in four general sections:

Section I: describing our new approach to development of a classifier referred to herein as a CMC/D classifier (Combination of Mini-Classifiers with Dropout). This new approach was used in the creation of a classifier useful for conducting the testing method of this document.

Section II: describing the specific CMC/D classifier developed in accordance with Section 1, which is used in the predictive test described in this document and results demonstrating its ability to predict NSCLC patient benefit from EGFRI-Is as compared to chemotherapy.

Section III: describing a presently preferred testing method for conducting a test on a patient sample using the CMC/D classifier described in Section II.

Section IV: describing practical computing environments for generating the classifiers and conducting the tests described in Sections 1-III.

Section I CMC/D Classifier Development Generally

CMC/D classifiers, their generation or development, and advantages, are described in this section. In general, CMC/D classifiers are particularly suitable when one is limited by the number of samples that are available for generation of a classifier. Furthermore, CMC/D classifiers are truly multivariate in character and have the advantage in that they avoid overfitting to an available sample set.

In contrast to standard applications of machine learning focusing on developing classifiers when large training data sets are available, the big data challenge, in bio-life-sciences the problem setting is different. Here we have the problem that the number of available samples is limited arising typically from clinical studies, and the number of attributes usually exceeds the number of samples. Rather than obtaining information from many instances, in these deep data problems one attempts to gain information from a deep description of individual instances.

CMC/D classifier development includes a first step a) of obtaining data for classification from a multitude of samples, i.e., measurement data reflecting some physical property or characteristic of the samples. The data for each of the samples consists of a multitude of feature values, and a class label. This set is referred to herein later as a "development set" or "development sample set", see FIG. 1 at 1100. For example, the data could be mass spectrometry data obtained from subjecting the sample to some form of mass spectrometry, e.g., MALDI-TOF, in the form of feature values (peak intensity at a multitude of m/Z ranges/peaks/features) as well as a label indicating some attribute of the sample. This label could have diagnostic or therapeutic attributes, such as a diagnostic label (cancer/non-cancer), whether the sample came from a patient that benefitted from some particular drug or combination of drugs (benefit/non-benefit), or a label indicating some other property or characteristic of the sample, such as whether the patient had an early or late recurrence of disease, had a good or poor overall survival, etc. The class label can be assigned previously in some automated fashion, or could be assigned by a human operator prior to or at the time of development of the classifier. The class label can also be newly defined over many iterations of the classifier development process, in other words the class labels are defined in conjunction with the development of the classifier itself.

The method continues with a step b) of constructing a multitude of individual mini-classifiers using sets of feature values from the samples up to a pre-selected feature set size s ($s$=integer 1 . . . n). For example a multiple of individual mini- or atomic classifiers could be constructed using a single feature ($s$=1), or a pair of features ($s$=2), or three of the features ($s$=3), or even higher order combinations containing more than 3 features. The selection of a value of s will normally be small enough to allow the code implementing the method to run in a reasonable amount of time, but could be larger in some circumstances or where longer code run-times are acceptable.

The method continues with a filtering step c), namely testing the performance, for example the accuracy, of each of the individual mini-classifiers to classify at least some of the multitude of samples, or measuring the individual mini-classifier performance by some other metric (e.g. the difference between the Hazard Ratios (HRs) obtained between groups defined by the classifications of the individual mini-classifier for the training set samples in the experimental and control arms of a clinical trial) and retaining only those mini-classifiers whose classification accuracy, or other performance metric, exceeds a pre-defined threshold to arrive at a filtered (pruned) set of mini-classifiers. In this step, each of the mini-classifiers compares the feature value(s) of the features (e.g., integrated intensity values in predefined m/Z ranges) forming the mini-classifiers in the sample set with the same feature values of the samples in a training set of class-labeled measurement data. In this step, the mini-classifiers execute a classification algorithm on the data for a sample from a chosen sample set based on the feature value(s) of the features selected for the mini-classifier, such as a K-nearest neighbor classification algorithm (KNN), relative to the same feature(s) in the training set, and output a class label for the sample. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained. Alternative supervised classification algorithms could be used, such as linear discriminants, decision trees, probabilistic classification methods, margin-based classifiers like support vector machines and any other classification method that trains a classifier from a set of labeled training data.

To overcome the problem of being biased by some univariate feature selection method depending on subset bias, we take a large proportion of all possible features as candidates for mini-classifiers in this step. We then construct all possible KNN classifiers using feature sets up to a pre-selected size (parameter s). This gives us many "mini-classifiers": e.g. if we start with 100 features for each sample, we would get 4950 (100×99/2) "mini-classifiers" from all different possible combinations of pairs of these features ($s$=2), 161,700 mini-classifiers using all possible combination of three features ($s$=3), and so forth. Other methods of exploring the space of possible mini-classifiers and features defining them are of course possible and could be used in place of this hierarchical approach. Of course, many of these "mini-classifiers" will have poor performance, and hence in the filtering step c) we only use those "mini-classifiers" that pass predefined performance criteria. These criteria are chosen dependent on the particular problem: If one has a two-class classification problem, one would select only those mini-classifiers whose classification accuracy exceeds a pre-defined threshold. We select those classifiers that would be predictive to some degree, i.e. where the hazard ratio (HR) between Late and Early recurrence groups is smaller in the treatment arm than in the control arm by some pre-specified value. Even with this filtering of "mini-classifiers" we end up with many thousands of "mini-classifier" candidates with performance spanning the whole range from borderline to decent to excellent performance. (In a typical example there are several thousand of such mini-classifiers which passed the filtering test and were used for logistic training with drop-out).

The method continues with a step d) of combining the filtered mini-classifiers using a regularized or regularization combination method. In one possible example of this, this step involves repeatedly conducting a logistic training of the filtered set of mini-classifiers generated at step c) to the classification labels for the samples. This is achieved by randomly selecting a small fraction of the filtered mini-classifiers as a result of carrying out an extreme dropout from the filtered set of mini-classifiers, and conducting logistical training on such selected mini-classifiers. While similar in spirit to standard classifier combination methods (see e.g. S. Tulyakov et al, *Review of Classifier Combination Methods, Studies in Computational Intelligence*, Volume 90, 2008, pp. 361-386), we have the particular problem that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. This is a regularization of the problem in the spirit of dropout as used in deep learning theory. In this case, where we have many mini-classifiers and a small training set we use extreme dropout, where in excess of 99% of pre-filtered mini-classifiers are dropped out in each iteration.

Other methods for performing the regularized combination method in step (d) that could be used include:

Logistic regression with a penalty function like ridge regression (based on Tikhonov regularization, Tikhonov, Andrey Nikolayevich (1943). "Об устойчивости обратных задач " [On the stability of inverse problems]. Doklady Akademii Nauk SSSR 39 (5): 195-198.)

The Lasso method (Tibshirani, R. (1996). Regression shrinkage and selection via the lasso. J. Royal. Statist. Soc B., Vol. 58, No. 1, pages 267-288).

Neural networks regularized by drop-out (Nitish Shrivastava, "Improving Neural Networks with Dropout", Master's Thesis, Graduate Department of Computer Science, University of Toronto; available on-line at the computer science department website of the University of Toronto (see application as filed for link).

General regularized neural networks (Girosi F. et al, Neural computation, (7), 219 (1995). The above-cited publications are incorporated by reference herein.

The method continues with step e) generating a master classifier from the combination of the filtered set of mini-classifiers after the regularized combination method step d) is performed, e.g., after the logistic training and dropout iterations. In one embodiment, this master classifier is an average over all the logistic regression training of those sets of filtered mini-classifiers selected during the dropout recited in step d). The final classifier can be evaluated against a test set split or subset of the development set, the evaluation also carried out over multiple different splits of the development set into training and test sets, and the final classifier can be generated by selecting one of the master classifiers resulting from a particular training and test set split having "typical" performance, or alternatively by retaining all of the master classifiers from each training and test set split and using a majority vote from each of the master classifiers to assign a label to a sample under test. This approach is similar in spirit to "drop-out" regularization, a method used in the deep learning community to add noise to neural network training to avoid being trapped in local minima of the objective function. See Nitish Shrivastava, "Improving Neural Networks with Dropout", Master's Thesis, Graduate Department of Computer Science, University of Toronto. Our method can also be viewed from an ensemble learning approach (see e.g. "Ensemble Methods", Zhi-Hua Zhou, CRC Press, 2012 Boca Raton). Such approaches have shown promise in avoiding over-fitting, and increasing the likelihood of generating generalizable tests, i.e., tests that can be validated in independent sample sets.

The CMC/D classifier generation method and resulting classifier recited above has many practical advantages and uses. Often, in classification development, particularly in the health sciences are such as cancer research or drug development, the researcher is faced with the problem of having only a small sample set available, which results in very small training and test sets if one were to follow a standard approach to classifier development. For example, in a sample set for a drug efficacy study, a training set could consist of perhaps 20 samples from the treatment arm and a training set of similar size if one also splits the control arm into training and test sets. This would result in only about 10 samples in the early and late recurrence groups (see below), defined by some training label assignment, such as Early or Late. Standard approaches would start by investigating features (e.g., peaks in mass spectrometry data) and select those features that show some promise of containing information relevant to the training classes. These would then be combined using a k-nearest neighbor method to generate a multivariate test. For small sample sizes, as in this example, the selection of features included in the construction of a multivariate test can easily be dominated by some features that show discriminating power primarily due to a particular split of the samples into training and test sets. In other words, using univariate p-values to select features becomes less informative for smaller sample sizes, as the p-values themselves become less informative. One could attempt to overcome this issue by trying out many training/test set split scenarios, but there does not seem to be a practical way to avoid picking specialized features for each of these scenarios, which makes an estimation of the generalization performance of developed tests difficult. In previous work we developed sophisticated cross-validation techniques, which showed substantial promise that a given sample set allows for the development of a predictive test. However, this work resulted in many classifier candidates, and the selection of a particular classifier for further validation remained difficult.

We developed the methodology described herein that addresses both issues: (a) it does not depend on a particular selection of features for inclusion in a multivariate test, and (b) by combining many, even thousands, of possible classifier candidates, it provides a means of automatically generating one single well performing classifier (test).

We coined the term "combination of mini-classifiers with dropout", CMC/D, to refer to the classifier generation method described in this document. The application of CMC/D to the mass spectrometry data set used in creation of the VS 1.0 test, is explained below in Sections II and III. CMC/D enables us to work with smaller training sets and so allows a splitting of a sample set into a training set and a test set. This alleviates a concern one can have in some classifier development problems, namely the lack of an independent test set. CMC/D also allows the investigation of the dependence of classifier performance on a particular test/training split, which could lead to bias for small sample sets. Lastly, CMC/D results in one master classifier/test for each training/test set split. While this test may not be the most optimal that could be constructed given the data, such a test will be, by construction, less prone to the dangers of overfitting to some artifact in the training set data.

The classifiers generated by CMC/D are probabilistic in nature as a result of using a logistic regression in the combination of "mini-classifiers" in step d) of the method. The result of applying a CMC/D classifier to a particular sample measurement data (e.g., mass spectrum) gives the probability of a particular class (group) label, in this case Early or Late, given the sample data.

FIG. 1 is a flow chart illustrating the classifier development process described in this section in more detail. The classifier development process would be typically implemented in a computing system taking the form of general purpose computer storing a classifier development set of data, e.g., in the form of mass spectrometry data and executable code implementing the modules shown in the Figure.

As shown in FIG. 1, the process begins with a classifier development set of data 1100, for example a set of mass spectrometry data obtained from a mass spectrometer (not shown) from blood-based samples of human patients. The process shown in the flow chart of FIG. 1 is not limited to any particular form of data, as mentioned earlier. However, the example of mass spectrometry of blood-based samples is suitable for the present discussion and not meant in any way to be limiting. In the present example the blood-based samples were obtained from patients who were members of a class of patients that are predicted to obtain overall survival benefit from an EGFR-I in treatment of NSCLC cancer, e.g., patients with VS 1.0 status of "Good". The class labels for these samples were further divided into two sub-classes, early and late as explained below.

At step 1102, the groupings (class labels) in the classifier development set 1100 are defined, such as for example "early" and "late" groups 1104 and 1106, respectively. In this example, the "early" group 1104 consists of the set of spectra in the development set 1100 which are associated with patients that had relatively early progression or recurrence of disease after administration of an anti-cancer drug. Conversely, the "late" group 1106 consisted of the set of spectra in the development set 1100 which was associated with relatively late recurrence or progression of disease after administration of the anti-cancer drug. Further considerations in defining the Early and Late groups are described in detail below. The split of the development set 1100 into early and late groups may or may not be into groups with even numbers of samples.

At step 1108, both the early and late sample groups are split into training and test sets. This split at step 1108 is not necessarily into equal groups. We could split in a 2:1 or other ratio. If we had a very large set, we might not want to use a really large training set. If we had very limited numbers of samples, we could use more samples in training set than in the test set. This splitting at 1108 results in two groups: training set 1112 and test set 1110 (each training and test set including both "early" and "late" samples/data from the development set 1100).

As shown in FIG. 1, the training set 1112 is then subject to classifier development steps 1120, 1126 and 1130. In step 1120, a multitude of KNN based mini-classifiers are created, as explained above in detail previously. These mini-classifiers may use only 1 (s=1) or perhaps 2 features (s=2) in the mass spectra data set for classification. As shown in the balloon 1122, the KNN mini-classifiers use subsets of compare the features (integrated intensity values of m/Z features, as shown in box 1124) drawn from the entire feature space. As show in the box 1124, these classification features are m/Z ranges in the spectra. The mass spectra could take the form of the "Deep MALDI" spectra as described in our earlier patent application serial no. U.S. Ser. No. 13/836,436 filed Mar. 15, 2013, also incorporated by reference herein. Alternatively, the mass spectra could take the form of typical "dilute and shoot" spectra from say 2,000 laser shots, or an sum average of several (e.g., three) 2,000 shot spectra with implementation of spectral filtering at the time of spectra acquisition. The features used for classification in the mini-classifiers are integrated intensity values, namely the area under predefined peak positions within a specified m/Z range. The generation of integrated intensity values for classification in the KNN mini-classifiers is preferably performed after pre-processing steps, such background subtraction, normalization and alignment of the spectra have been performed. These steps, and the implementation of the KNN mini-classifiers, is performed by computer code within a general purpose computer.

At step 1126, a filtering of the KNN mini-classifiers generated at step 1120 is performed, to only save those mini-classifiers that had an acceptable level of performance. This is explained intuitively in FIG. 1. There can be overlapping sets of features that are both good, poor and one of each. The feature sets can overlap and some will pass filtering and some will not. Each mini-classifier is assessed relative to a defined performance metric. In this step, only those mini-classifiers that had good classification performance are retained, as indicated by the plus sign at 1128.

At step 1130, a master classifier is generated from the mini-classifiers that passed the filtering step after performing a regularized combination method, such as many logistic regression and drop-out regularization iterations, as explained above. In more detail, the result of each mini-classifier is one of two values, either "Early" or "Late". We can then use logistic regression to combine the results of the mini-classifiers in the spirit of a logistic regression by defining the probability of obtaining an "Early" via standard logistic regression (see e.g. http://en.wikipedia.org/wiki/Logistic_regression)

$$P(\text{``early''} | \text{feature for a spectrum}) = \frac{\exp\left(\sum_{\text{Mini classifiers}} w_{mc} I(mc(\text{feature values}))\right)}{\text{Normalization}} \quad \text{Eq. (1)}$$

where I(mc(feature values))=1, if the mini-classifier mc applied to the feature values of a sample returns "Early", and −1 if the mini-classifier returns "Late". The weights $w_{mc}$ are unknown and need to be determined from a regression fit of the above formula for all samples in the training set using +1 for the left hand side of the formula for the Early-labeled samples in the training set, and −1 for the Late-labeled samples, respectively. As we have many more mini-classifiers, and therefore weights, than samples, typically thousands of mini-classifiers and only tens of samples, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same, we use only a few of the mini-classifiers for a regression, but repeat this process many times. For example we randomly pick three of the mini-classifiers, perform a regression for their three weights, pick another set of three mini-classifiers, and determine their weights, and repeat this process many times, generating many random picks, i.e. realizations of three mini-classifiers. The final weights defining the CMC/D classifier are then the averages of the weights over all such realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function. This master classifier could be implemented as an average of the combination of the filtered classifiers after logistic regression and drop-out regularization. The data set forming this master classifier (MC) is indicated at 1132 and is stored in the memory of the computer executing the method shown in FIG. 1.

At step 1134, the performance of the master classifier generated at step 1130 is then tested by subjecting the test set split of the development set data (1110) to classification by the master classifier. (Again, the test set may be subject to pre-processing steps prior to execution of classification algorithm in the master classifier.) The results of the performance of the master classifier are stored and can be represented for example as a histogram of Hazard Ratio distributions, as shown in FIG. 1 at 1138 or in the previous description.

The steps 1108, 1110, 11128, 1120, 1126, 1130, 1132 and 1134 are repeated as indicated by the loop 1136 with a different split of the early and late sample sets into different training and test set realizations. The purpose of loop 1136 is to avoid training set/test set split bias. The result of each iteration of the loop 1136 is a different master classifier. The performance of the master classifier is evaluated for each sample the test set (1110) for each realization of the training and test set split.

At step 1136, the classifier performance data (e.g., HR histograms) from each training/test set split is analyzed. For example, as shown in FIG. 1 at 1138, each realization of the training/test set split produced a master classifier and a histogram of the hazard ratios of the classifications (early/late) produced by the many master classifiers can be created. The distribution of the hazard ratios can be used to assess classifier performance, as explained previously. It will be noted that overfitting of the final master classifier to the training data is minimized by the regularization step (1132) and selection of either a master classifier from one of the master classifiers having a typical performance, or by averaging over all the master classifiers, e.g., using a majority vote algorithm from all the master classifiers, or applying a weighting to all of the master classifiers. Confidence in the final classifier performance estimates in the analysis step 1136 is enhanced by the observation of many master classifiers with similarly good performance.

There may be instances where particular samples (typically a small number) in the training set are often misclassified by a master or final classifier. In this situation, it may be useful to redefine the training labels for such samples, e.g., change the label from "Early" to "Late". This is particularly relevant for classification problems where the training labels are hard to define, e.g. in tests for treatment benefit or relative treatment benefit. This is done at step 1142 and the process loops back to step 1102 and the splitting of the development set into "early" and "late" groups according to the corrected training labels proceeds. The process of splitting these groups into training and test set splits at step 1108 and the subsequent steps in the flow chart proceeds, resulting in a new evaluation of the master classifier performance at step 1136 and 1138. Step 1140 is not always necessary, e.g., where there are few or no instances of misclassification, in which case after the analysis step 1136 the processing proceeds directly to step 1144.

At step 1144, the procedure for defining a final test label for a sample to be tested is defined. The final test table label for a sample can be specified in several ways, for example it can be defined as the result of a majority vote on the classification label of all the final master classifiers from all the training/test set splits. Alternatively, it can be defined as the label produced by a selected master classifier for a given training/test set split that provides typical performance, or alternatively by the use of a statistical analysis of the classification results produced by the master classifier e.g., using the procedures described in the following section.

Section II Generation of CMC/D Classifier from Mass Spectrometry of Patient Blood-Based Samples for NSCLC Patient Selection for EGFR-I Drugs (VS 2.0)

An example of the generation of a CMC/D classifier useful to guide treatment of NSCLC patients will be described in this section. The generation of the classifier largely follows the method described above Section 1 and in the discussion of FIG. 1 above. However, the processing of a test sample to make a prediction using the CMC/D classifier in this example makes use of reference spectra, as well as additional adjustments to the processing of the spectra to take into account restrictions on machine qualification and spectral reproducibility which were present. The generation of the final classification label for a sample under test also makes use of feature-dependent noise characteristics and other techniques which will be described in greater detail below in conjunction with FIG. 2. Nevertheless, this section will demonstrate a further example of the generation of a CMC/D classifier from mass spectral data and the use thereof to make predictions in advance of treatment on whether a NSCLC patient is likely to benefit from administration of an EGFR-I drug.

The classification problem is unusual in the sense that at the outset of the problem (generation of the classifier) we do not know what the 'correct' class labels are. In some sense this problem is more like an unsupervised learning problem. We address this issue by starting with an initial guess of the class labels, training a test for these guesses, and iterate this procedure to refine the class labels. The output of this procedure are the final class labels and the algorithm to detect these classes from a patient's sample.

As was explained earlier in this document, the VeriStrat test described in prior U.S. Pat. No. 7,736,905 (referred to herein occasionally as "VS 1.0"), among other things, makes a prediction in advance of treatment whether a NSCLC patient is a member of a class, referred to as VeriStrat "Poor", which is not likely to benefit from EGFR-Is such as erlotinib and gefitinib in treatment of NSCLC. The prediction is based on a mass spectrum of a blood-based sample from the patient and the use of a classifier implemented in a computer. The results from recent EGFR-I trials in treatment of NSCLC, known as the TAILOR and DELTA trials, indicate that erlotinib may be the inferior treatment in an EGFR wild type population. Consequently, the use of Tarceva (erlotinib) has fallen outside of front-line treatment for patients whose tumor shows EGFR sensitizing mutations, and as salvage treatment in higher lines.

The test described in the '905 patent does not describe how to make a prediction of whether an EGFR-I such as erlotinib would be a superior treatment over chemotherapy, even in those patients testing VeriStrat "Good" in the VS 1.0 test. Subsequent studies, such as the PROSE study[1] were not designed to show superiority of one treatment over another. Furthermore, while the small number of the VeriStrat "Good" patients in the PROSE study was by far too small to argue for equivalence of erlotinib and chemotherapy treatments, there is also no evidence from the PROSE study that one treatment is superior to the other.

[1] See V. Gregorc et al., Randomized Proteomic Stratified Phase III Study of Second-Line Erlotinib Versus Chemotherapy in Patients with Inoperable Non-Small Cell Lung Cancer, presentation presented at ASCO annual meeting June 2013.

The present inventors have been developing and applying our new CMC/D classifier development methodology to this problem. During the development of our approach to probe deeper into the serum proteome, using what we have called "Deep MALDI", we have also developed tools and algorithms to increase our ability to enhance the peak content of standard mass spectral acquisition techniques by combining the spectra from multiple technical replicates of a standard acquisition, such as a standard "dilute and shoot" mass spectral data acquisition used in the VS 1.0 test and described in U.S. Pat. No. 7,736,905. An example of this combination of spectra from multiple technical replicates of standard "dilute and shoot" mass spectral acquisitions is described in this section.

A goal of the recent classification effort was to develop a new test (referred to herein as VeriStrat 2.0 or VS 2.0) that identifies a group of NSCLC patients having more benefit from erlotinib than chemotherapy. This new test, and the method of generating the classifier used in the test, is described in this document. In one possible implementation of the test, the test is based on standard MALDI-ToF mass spectral acquisition, e.g., 2000 shot "dilute and shoot" spectra. As a classifier development set (FIG. 1, 1100), we had available to us a subset of samples from the original development set and initial validation sets used in generating the VS 1.0 test of the '905 patent. We chose for those samples forming the development set those patients who tested VS Good under the VS 1.0 test, i.e., those patients who were predicted to obtain an overall survival benefit from EGFR-Is. The resulting test as described in this document shows superiority of erlotinib over chemotherapy in a selected subset, while retaining the predictive character of the VS 1.0 test. The test described in this document explains how to identify if a NSCLC patient is a member of this subset of patients that are likely to obtain more benefit from an EGFR-I such as erlotinib than chemotherapy. This subset is associated with the class label "Late" in this following discussion The class label could be given some other equivalent name in order to identify such patients, such as "EGFR Benefit", "Positive", "+", or the like. Thus, the particular moniker for a class label is not important. Hence, in this disclosure and in the claims when we say "late or the equivalent", or "early or the equivalent" we mean that the choice of the moniker for the class label is not important.

The test described in this document could optionally feature a classification algorithm in which patients identified as Poor or the like are predicted to not benefit from EGFR-Is in treatment of NSCLC cancer. A third class label can be assigned to the patient sample under test, referred to here as "Intermediate", which is associated with patients that are predicted to perform in clinically meaningful terms similarly on either chemotherapy (docetaxel, pemexetred) or an EGFR-I such as gefitinib or erlotinib.

Patient Population and Available Samples

The following cohorts of patients had samples available for this project: sample sets known as "Italian A", "Italian B", "Italian C." Italian A and B were cohorts of patients with advanced NSCLC treated with gefitinib used in the development and validation of the original VeriStrat test. See generally, U.S. Pat. No. 7,736,905; Taguchi et al., JNCI 99: 838-846 (2007). Italian C was a cohort of patients treated in advanced line with a variety of chemotherapy regimens.

The initial plan was to directly create a predictive classifier to identify patients having better outcomes on gefitinib compared with chemotherapy by using all three cohorts of patients. However, as overall the outcomes in the Italian C cohort within the subset of patients for whom progression-free survival (PFS) data were available were generally inferior to those of the Italian A and B cohorts, this method did not work well.

Initial efforts to use all samples to create a classifier identifying patients who had good outcomes on gefitinib therapy produced many classifiers that produced classifications having extremely strong overlap with original VeriStrat classifications, i.e. we were able to produce many classifiers having similar performance and producing very similar sample classification compared to original VeriStrat using CMC/D methodology and different features. This was true even when features in regions of the spectra overlapping with mass spectral features from VeriStrat were excluded from the process.

Therefore, it was decided to restrict the classifier construction process to a classifier development sample set consisting of samples that yielded an original "VeriStrat Good" classification in the VS 1.0 test, i.e. to design a classifier that splits the VeriStrat Good samples into patients with better or worse outcomes on EGFR-Is. Finally, as there are reasons to believe that patients with performance status (PS) 2 and patients in fourth line of therapy are generally likely to receive very little benefit from gefitinib therapy, samples from these patients were also not included in classifier training Other samples from the three cohorts, including VeriStrat Poor samples from the original development set, samples from the Italian C cohort, and samples from patients with PS 2 and in fourth line therapy, were still used in classifier evaluation during the development process. Moreover, in a clinical application of the CMC/D classifier described later on in this section, the training set used for classification included feature values from spectra from patients having a class label VeriStrat Poor.

The list of samples used during classifier development is given in Appendix A.

The development of the new CMC/D classifier is depicted in the diagram shown in FIG. 1. The diagram is discussed at length above. Basically, and as a first approximation, the development sample set (Appendix A) was divided into two groups ("Early" and "Late") depending on whether the patient associated with the sample experienced early or late progression of disease after commencement of treatment with an EGFR-I. See FIG. 3, discussed below. Those patients that experienced late progression can be considered for the initial assignment of class labels as those patients that benefitted more from EGFR-I treatment than an alternative such as chemotherapy, and had assigned to their specimen the class label "Late". Those patients that experienced early progression can be considered, as an initial estimation, as those patients that did not benefit more from EGFR-I treatment than chemotherapy, and had assigned to their specimen the class label "Early".

From these two groups of samples, the groups were separated into training and test sets of approximately equal size (FIG. 1, step 1108). The training sets were subject to the CMC/D classifier generation steps 1120, 1126, 1130, 1134 shown in the right hand side of FIG. 1, using features in the MALDI-ToF spectrum of their serum samples. The test samples were classified by the resulting master classifier (MC) and the MC performance was evaluated at step 1134 over the test set of samples (1110). The process looped over many training/test set split realizations (250 in this example). Samples subject to misclassification were given redefined training labels, and the CMC/D classification and evaluation steps were repeated (steps 1140, 1142). This label re-definition process was repeated twice in the development of this test. A final classifier was then selected from the MCs, in this instance a majority vote of all 250 classifiers resulting in each of the training/test splits. Alternative constructions for the final classifier are also possible, such as selection of one MC that provides "typical" performance, an average of the 250 MCs, or otherwise.

Spectral Acquisition and Pre-Processing

The mass spectra used in classifier generation in FIG. 1 are acquired by a Bruker mass spectrometer from a blood-based sample. The mass spectra are subject to pre-processing steps prior to classification. The steps are described in this section.

a. Generation of Mass Spectra Used During Development

Spectral acquisition of blood-based samples was performed using qualified mass spectrometry machines used for VeriStrat testing (for details see Appendix H). Machine qualification can be performed using the methods of the patent of J. Röder et al., U.S. Pat. No. 8,467,988, the content of which is incorporated by reference herein.

The spectra were acquired in triplicates of 2,000 acquired shot spectra. In this particular instance, the spectra were filtered at the time of acquisition using Bruker Flexcontrol settings to only acquire spectra with desired qualities. The number of actual shots the sample was subjected to is higher than 2000, and varies from sample to sample and from MALDI spot to MALDI spot. The triplicates of spectra acquired for each sample were aligned and averaged to produce one 6,000 shot spectrum per sample.

b. Background Estimation and Subtraction

The first step in pre-processing the averaged spectra was background estimation and subtraction. The background component of the averaged spectra was estimated using the single window method and a multiplier of 100. The estimated backgrounds were then subtracted from the averaged spectra.

c. Spectral Alignment

In any mass spectra there are slight discrepancies with respect to the translation of time-of-flight numbers to m/Z values. We identified a set of peaks that are present in the vast majority of the mass spectra and rescaled each spectrum's m/Z values such that the sum of the squared deviations of the common peaks in each individual spectrum to the reference set is as small as possible. This process leads to better resolution of close (in m/Z) features.

d. Normalization

In order to obtain features that differentiate between clinical groups, we need to measure the intensity of peaks from different samples and compare their values. The overall amount of ionized protein is not controllable within the MALDI process, and so we can only measure relative peak intensities. To do this we need to normalize the spectra. In order to avoid propagating the variability of peak intensities from peaks that are either intrinsically variable or which correlate to the clinical status of the patient to stable peaks during normalization, care needs to be taken in determining which regions of the spectrum can be used for normalization. The m/Z regions used for normalization were selected using a partial ion current normalization tool. Partial ion current normalization in known in the art and the interested reader is directed to the discussion of normalization procedures in U.S. Pat. No. 7,736,905.

e. Feature Definitions and Feature Tables

In order to define possible candidates for peaks that can differentiate between clinical groups (i.e., m/Z features used in KNN classification) we located peaks in the pre-processed spectra and defined a range in m/Z around each peak's maximum. These ranges in m/Z define features that are used for all further analysis. We selected 76 features as possible candidates for differentiating between groups and calculated the integrated intensity of each of these features for each spectrum. In this way we obtain a feature value for each feature for each spectrum. The tabular listing, rows are spectra, columns are features, of these integrated intensities (feature values) is referred to as the feature table, which is stored in memory of a general purpose computer implementing the method of FIG. 1. Two of the features defined, at m/Z=7616 and 14392 were not used during the CMC/D classifier development process, due to lack of sufficient feature quality (noise) on re-inspection. We observed that some of the samples showed substantial levels of oxidization leading to double peak structures or shift of similar peaks. In order to avoid missing the oxidized version of underlying polypeptides we used very wide feature definitions. The definitions of the 74 m/Z features used in the CMC/D classifier generation process are provided in Appendix B.

CMC/D Classifier Development Method

Selection of Early/Late Progression Groups and Training and Test Sets (steps 1102 and 1108, FIG. 1)

From clinical data it is not possible to determine, with certainty, which patients benefit more or less from a given therapy. As a first approximation to defining class labels for the development set, we decided to define the class labels as whether those patients benefitted more or less from treatment with an EGFR-I, in step 1102 (FIG. 11) patients with PFS less than 80 days were defined as "Early" (Early Progression indicative of possible little benefit from therapy) and patients with PFS in excess of 200 days were defined as "Late" (Late Progression indicative of possible greater benefit from therapy). See FIG. 3. This resulted in 23 patients in the "Early" group and 23 patients in the "Late" group. These are listed in Appendix C with their assigned class label. These were then split into training (11 "Early" and 11 "Late") and test sets (12 "Early" and 12 "Late"), step 1108 in FIG. 1, stratified by line of therapy and performance status (PS). It is possible that some training/test splits can produce training sets that are particularly good or poor for creation of a classifier and test sets that are particularly easy or difficult to classify. Hence, the stratified training/test split was done randomly 250 times (indicated by the loop 1136 in FIG. 1). Each split provides a training set 1112 leading to generation of a CMC/D master classifier (MC), step 1130 in FIG. 1, the performance of which can be assessed on the corresponding test set. (Step 1134) To provide test sets that are representative of the population in terms of distribution of PFS times, half of the patients with PFS between 80 and 200 days with PS 0 or 1 and in first to third lines of therapy were randomly selected for inclusion in the test set 1110. The initial assignment of class labels and split into training and test set are shown in FIG. 3.

Figure 11:
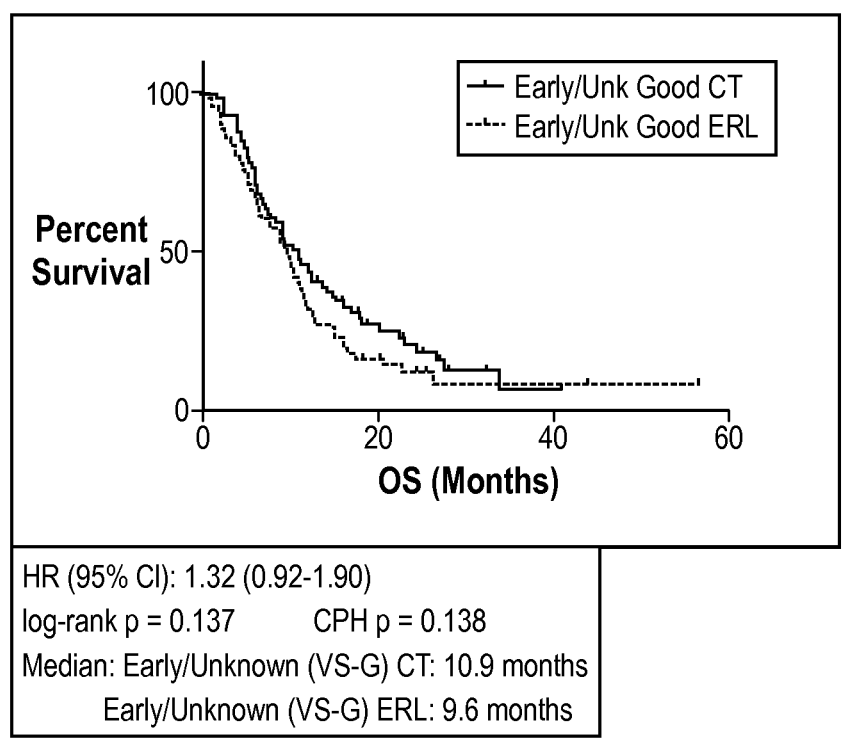
FIG. 11 is a Kaplan-Meier plot of OS within the VeriStrat Good Early/Unknown group by treatment.

Creation of Mini-Classifiers (Step 1120, FIG. 11)

For a given training set it is possible to create many individual K-nearest neighbor (KNN) classifiers using subsets of the 74 features. These individual KNN classifiers, defined by the samples in the training set and the particular subset of features define a "mini-classifier" (mC). For this project K=5 in the KNN algorithm was fixed throughout.

All mCs were considered that used one of the 74 features (s=1) or a pair of the 74 features (s=2). This gave a total of 2775 mCs for each training set.

Filtering of Mini-Classifiers (Step 1126, FIG. 11)

The mini-classifiers generated in step 1120 are pruned based on filtering by performance of the mCs on the training set. This was done using the ERRORS method of the CMC/D process with Jmin=0.7 and Jmax=0.9. This means that each mC was applied to its training set. The accuracy with which it assigned "Early" and "Late" labels was calculated. If this accuracy was between 0.7 and 0.9, the mC passed filtering and could be used to make the master classifier (MC). If the accuracy lay outside of this range, the mC failed filtering and dropped from the CMC/D process. The number of mCs passing filtering depends on the training set, i.e., the particular training/test set split realization, but typically was of the order of 1000-1500.

In essence, the ERRORS method assesses the accuracy of the classification given by the mC. In the filtering process each mC is applied to each member of the training set and this gives us a classification for each member of the training set. We know the definition (class label) we have assigned to each member of the training set, so we just calculate the proportion of correct classifications for each mini-classifier. We picked that this accuracy (proportion of correct classifications) had to lie between 0.7 and 0.9.

We intentionally did not push the upper limit up (Jmax) to the perfect classification of 1.0. Firstly, there are not many mini-classifiers that achieve this accuracy, but secondly, and more importantly, we are trying to avoid over-fitting at each stage of the process when generating a classifier. Mini-classifiers that achieve exceptionally high accuracy are likely to be 'special' and not 'typical', resulting from some peculiarities of the training set and features, and not likely to generalize well. So, we choose not to include mini-classifiers that are 'too good' into the master classifier. It is quite interesting to note that when filtering criteria are set too extreme and mini-classifiers that have exceptionally good performance are combined, the overall classifier produced turns out to have poorer performance.

Creation of Master CMC/D Classifier Using Logistic Regression with Drop Out (Step 1130)

The mCs that passed filtering were combined into one master classifier (MC) by training a logistic regression using the Late and Early training set labels with extreme drop out as a regularizer. Ten thousand drop-out iterations were carried out, in each of which 5 mCs were randomly selected and combined using logistic regression. The logistic regression weights for each mC (see equation 1, supra) from each drop-out iteration were averaged to produce the final weights for the logistic combination into a final MC.

CMC/D Classifier Performance Assessment (Step 1134, 1136, FIG. 11)

Figure 4B:
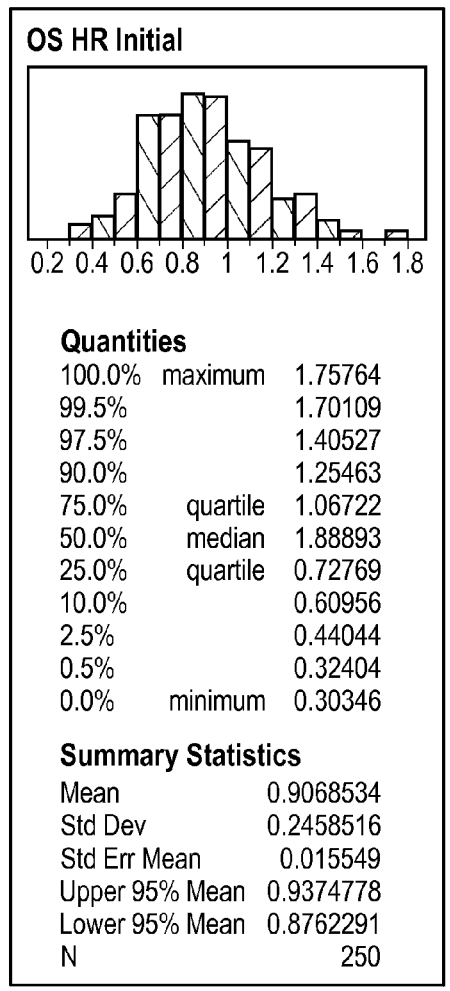

Once the master classifier was created for a given training/test set realization, it was evaluated by running the classifier on the test set (1110) and on spectra obtained from samples from the Italian C cohort in step 1134. This process was performed for each of the 250 training and test splits. Quantities evaluated included hazard ratio (HR) between "Early" and "Late" classifications of the test set and for the Italian C cohort for overall survival (OS) and PFS and medians for "Early" and "Late" classifications for the test set and Italian C cohort. The HR distributions for PFS and OS generated are shown in the FIGS. 4A-B. In addition, individual classifications of class labeled samples were examined when they were in the test set. Many samples repeatedly were assigned classifications that did not match their PFS-defined labels. These samples were identified and are listed in Table 3.

TABLE 1

| Samples persistently misclassifying Sample ID |
|---|
| ICA_11 |
| ICA_12 |
| ICA_18 |
| ICA_20 |
| ICA_21 |
| ICA_22 |
| ICA_36 |
| ICA_38 |
| ICA_39 |
| ICA_45 |
| ICA_51 |
| ICA_68 |
| ICB_22 |
| ICB_3 |
| ICB_38 |
| ICB_49 |
| ICB_61 |

Refinement of Initial Class Label Assignment (Step 1140, FIG. 1)

The class labels of the samples that persistently misclassified over many training/test splits, listed in Table 1, were flipped ("Early" to "Late" and "Late" to "Early"). This produced a new set of training labels for the CMC/D classifier generation process to be carried out again.

Figure 4C:
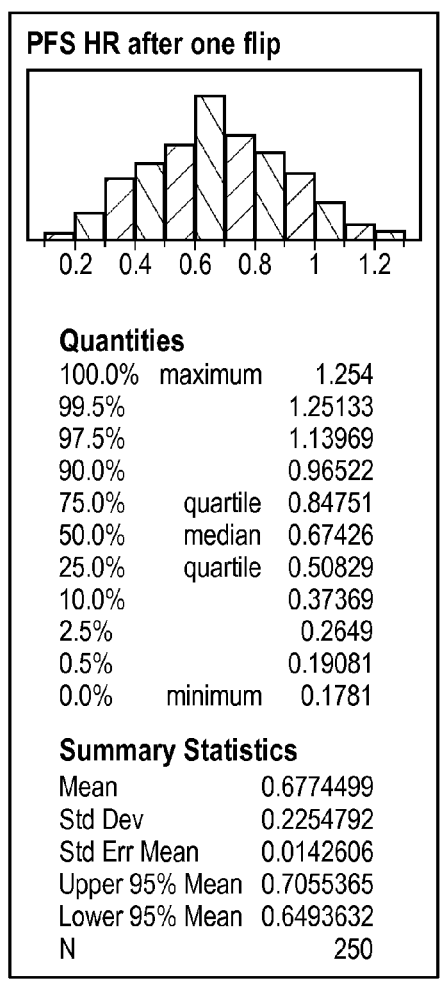
Figure 4D:
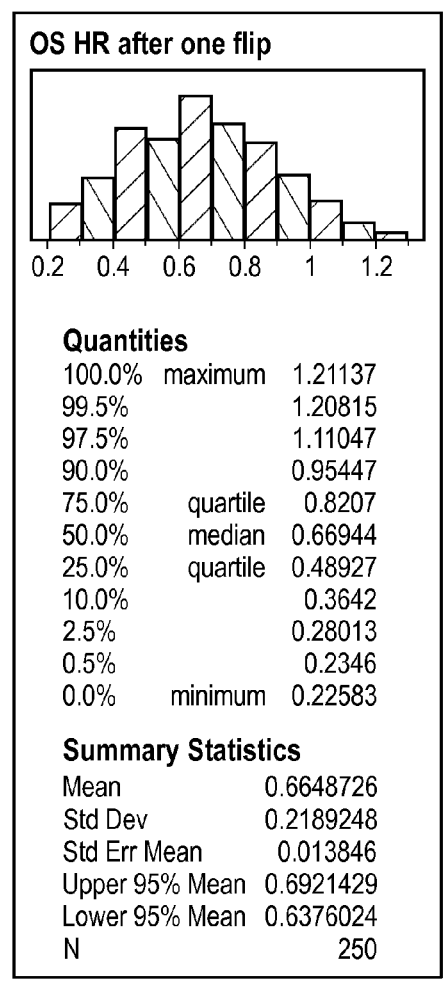
Figure 4E:
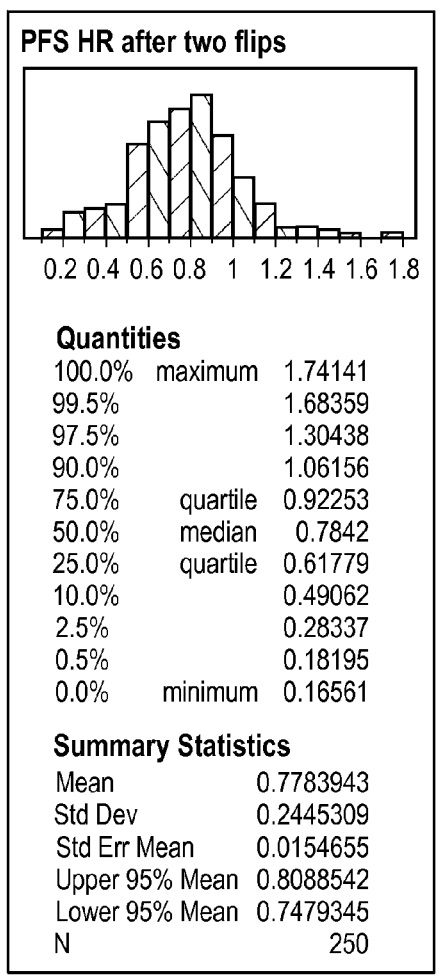

Using the new labels, the "Early" and "Late" samples were again randomized into training and test sets 250 times, as before stratified on line of therapy and PS. Mini-classifiers were created as before and filtered using identical criteria. These filtered mCs were combined using logistic regression with drop-out to create MCs and the performance of the MCs was assessed on the new test sets. The distributions of HRs for PFS and OS generated are shown in the FIGS. 4C and 4D. The distributions of HR for PFS and OS generated after two flips are shown in FIGS. 4D and 4E.

Several samples were identified that persistently misclassified when part of the test set. These are listed in Table 2.

TABLE 2

| Samples persistently misclassifying after first set of class label flips Sample ID |
|---|
| ICA_20 |
| ICA_21 |
| ICA_38 |
| ICA_39 |
| ICA_45 |
| ICB_12 |
| ICB_40 |

The class labels of the samples that persistently misclassified after the second running of the CMC/D process, listed in Table 4, were flipped ("Early" to "Late" and "Late" to "Early"). This resulted in a new set of class labels, which were again randomized to training and test groups 250 times, stratified by line of therapy and PS. The whole procedure of creating mCs, filtering, combining to MCs, and assessing performance was repeated a third time. After the third repetition of the process, only two samples classified poorly when in the training set and it was decided that no further processing was required.

Figure 4F:
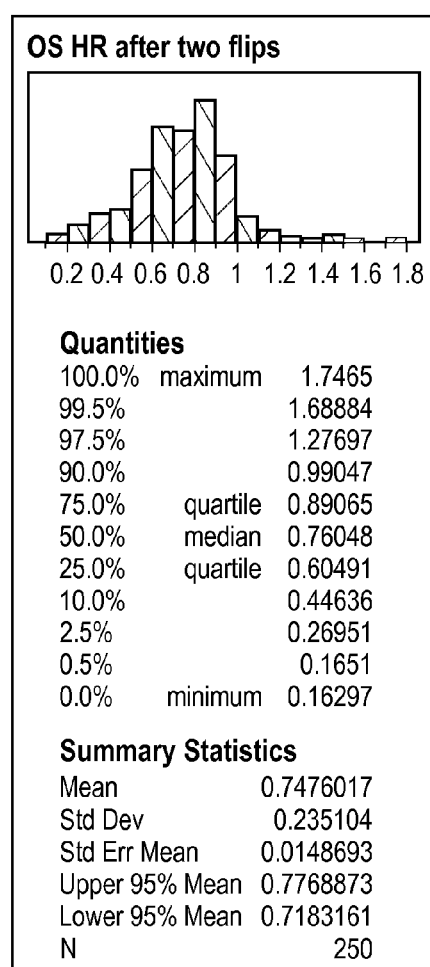

The distribution of MC performance for the 250 training/test splits of the third iteration of the CMC/D process is shown in FIGS. 4E-4F. More than 90% of the training/test split realizations yielded HRs between Early and Late classifications of the test sets that were less than 1, and more than half of the realizations had HRs less than 0.76 for PFS and less than 0.78 for OS. Instead of selecting one of these individual training/test splits for a final test/CMC/D classifier, the final classifier was defined as the majority vote of all 250 MCs for the third CMC/D iteration. This has the advantage of not requiring selection of a master classifier from a particular training/test set spit with the possibility of a particularly beneficial test or training set, and also removing any element of human subjectivity in making a choice and potentially providing a more robust final classifier.

Adjustments to Take Account of Restrictions on Machine Qualification and Spectral Reproducibility The implementation of the final classifier described above to generate a class label for a sample under test implements certain adjustments in the mass spectral data processing to take into account some restrictions on machine qualification and spectral reproducibility that were present when the test was being developed. These adjustments are described in this section. This procedure is also described later on in conjunction with FIG. 2. It will be apparent to persons skilled in that art that these adjustments may not be necessary to generate a CMC/D classifier or implement a predictive test using a CMC/D classifier. The adjustments described in this section arose out of certain limitations of the mass spectrometer we used to generate mass spectra, and also out of the desire to increase the stability of the test.

A. Correction of Variations in m/Z Sensitivity of Mass Spectrometer

Spectra were acquired using Bruker mass spectrometer machines qualified previously to perform the original VeriStrat testing, using procedures described in J. Roder et al., U.S. Pat. No. 8,467,988. While the original VeriStrat 1.0 test only uses features between 5 kDa and 13 kDa, the test described in this section uses features with higher and lower m/Z positions, in addition to features in this range. Spectrometers qualified for the original VeriStrat test must have adequate reproducibility of the mass spectral features used for the original test, but there are no requirements on m/Z sensitivity outside of this range.

Comparison of reference spectra generated from a reference sample at the same time as the spectra used in the present test development were generated with spectra generated from the same reference sample at a later time, both on previously qualified machines, indicated that, while m/Z sensitivity was similar for features within the 5 kDa to 13 kDa feature range, outside of this range the m/Z sensitivity showed some systematic differences.

To be able to compare spectra generated at different times or on different machines in a qualified setting at a level useful for testing in accordance with this new test, the feature values need to be corrected for these differences in m/Z sensitivity. This can be done using the reference spectra generated from a single reference sample that have been generated in the same batch as spectra used for present test development and subsequent batches of spectra from patient samples to be classified using the new VS 2.0 test. In this example (as shown in FIG. 2 at 1202A and 1202B), the reference samples were serum samples from a healthy human.

Two preparations of a reference sample were run in triplicate with the spectra used for VS 2.0 development. These triplicates were averaged using the averaging workflow and pre-processed using the pre-processing workflow (see discussion of FIG. 2, infra). Feature values were generated and the feature values compared between the two preparations. In order to avoid using outlier feature values from one or the other preparation, features were pared down to those for which the feature vales were within 10% of each other for the two preparations. If FV1 is the feature value for a particular feature for preparation 1 of the reference sample (1202A, FIG. 12) and FV2 is the feature value for the same feature for preparation 2 of the reference sample (1202B, FIG. 12), the feature was considered suitable for analysis of relative m/Z sensitivity if:

$$|1-(FV1/FV2)|<0.1 \text{ or } |1-(FV2/FV1)|<0.1. \qquad \text{Eq. 2}$$

The feature values for these features are to be compared with the feature values for the same features generated from preparations of the reference sample in a subsequent batch of samples for VS2.0 testing. If two preparations are available in the subsequent batch, ideally run before and after the samples to be VS2.0 tested, the threshold of Eq. 2 should be met also for the features that can be used for m/Z sensitivity comparison within the second batch. If more than 2 preparations of reference sample are available, Eq.2 can be generalized to use the information available from the increased number of spectra so that the standard deviation of the feature values can be compared with the average feature value for each feature and features can be used for which the ratio of the standard deviation to the average are below a set threshold, such as 0.1.

Once a subset of the features are identified of suitable reproducibility, the variation in the m/Z sensitivity from the VS2.0 development batch of samples to any subsequent batch of samples can be examined in a plot of the ratio of the average feature values of the reference spectra in the development batch (AVO) to the average feature values of the reference spectra in the subsequent batch (AVN) as a function of m/Z. Such a plot is illustrated in FIG. 5.

Figure 5:
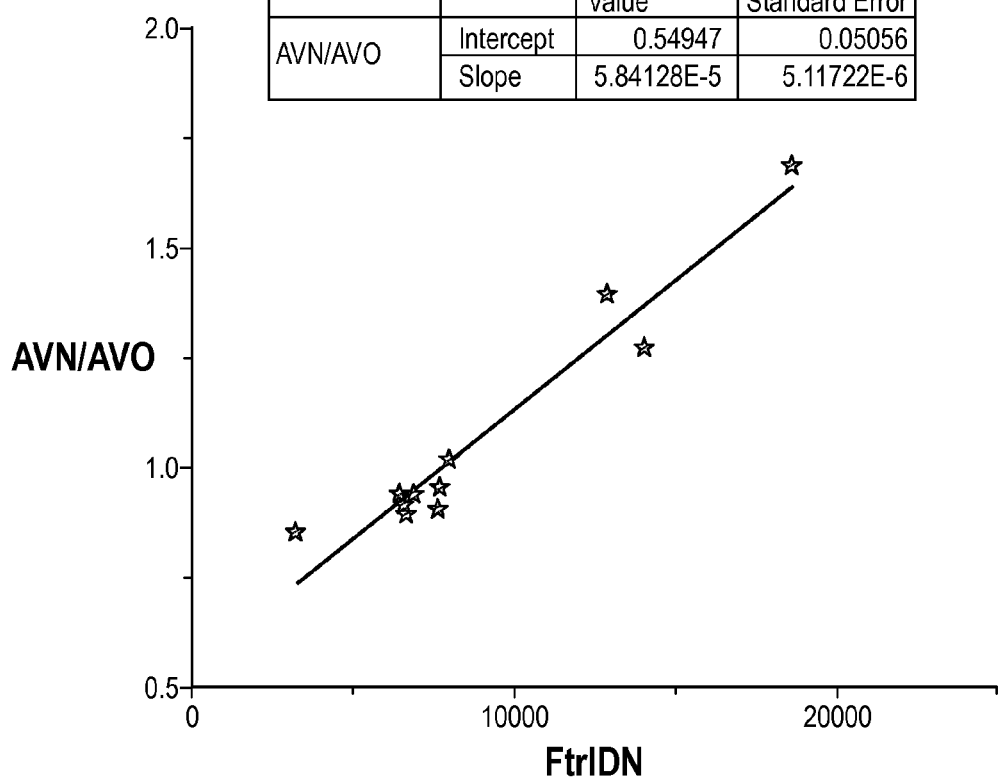
FIG. 5 is a plot of feature value ratio between the development set and a subsequent back of spectra for features passing the concordance criterion of Equation 2 obtained from the same reference sample.

A systematic variation in m/Z sensitivity can be seen in FIG. 5, with the development batch having lower sensitivity at higher m/Z and higher sensitivity at lower m/Z than the subsequent batch. To allow for a correction for this systematic difference in m/Z sensitivity, a straight line was fitted to the data in FIG. 5 and the slope and intercept determined. This gives a function with which each feature value obtained for any sample in the subsequent batch can be corrected to make it comparable with the feature values obtained for samples in the VS2.0 development batch.

B. Analysis of Stability of VS2.0 Classifications to Noise Inherent in the Acquisition of Mass Spectral from Serum Samples Via the VS1.0 Sample Handling and Spectral Acquisition Process VS1.0 is a highly reproducible test, with reproducibility of classifications in excess of 95%. One method of gaining reproducibility within the test is the use of the triplicate spotting of the sample for spectral generation and comparison of the triplicate labels before generation of the VS1.0 classification. As the triplicate spectra from a sample are averaged for the VS2.0 test, the redundancy of VS1.0 is lost and this approach cannot be extended to VS2.0. However, a method of in-silico generation of multiple replicates for a given test sample has been developed which allows for a simulation of the effect of the sample- and MALDI-spot-dependent, non-systematic irreproducibility (noise) inherent in the process of VS1.0 sample preparation, spotting and spectral generation.

To characterize the noise for each feature two runs of the Italian A, B, and C sample sets performed on mass spectrometers newly qualified for VS1.0 were compared. For each VS2.0 feature the feature values for each sample were compared across the two runs. This produced a concordance plot for each VS2.0 feature. For each concordance plot, a linear regression was used to fit a straight line to the feature value data. To characterize the noise around this fit, the residuals of the linear regression were examined. The noise was assigned to be predominantly additive or predominantly multiplicative. For additive noise, the noise strength was defined to be the standard deviation of the residuals. For multiplicative noise, each residual was divided by the corresponding feature value and the standard deviation of this quantity was defined to be the noise strength. The noise types and noise strengths for the VS2.0 features estimated in this way are given in Appendix D.

Having characterized the noise for each feature by its type and strength, $\sigma$, noisy realizations of each feature for each sample, with measured feature value, F, could be generated via:

$$\text{additive noise: } F_{noisy} = F + \sigma\epsilon \quad \text{Eq. (3)}$$

$$\text{multiplicative noise: } F_{noisy} = F(1 + \sigma\epsilon) \quad \text{Eq. (4)}$$

where $\epsilon$ is a Gaussian random number with zero mean and unit standard deviation.

To investigate the stability of the VS2.0 classification under noise for a particular test sample, 160 noisy realizations of the feature table for each sample were generated using Eq. (3), Eq. (4) and the noise parameters for each filter given in Appendix D. Each noisy realization was classified using the 250 MCs generated during the final iteration of the CMC/D process outlined above. This produced 250 classifications of "Early" or "Late" for each noisy realization of the sample, i.e. 40,000 "Early" or "Late" classifications per sample. Let the total number of "Early" classifications across the 250 master classifiers be $N_{Early}^i$ and the total number of "Late" classifications across the 250 master classifiers be $N_{Late}^i$, where $1 \leq i \leq 160$. By definition, $0 \leq N_{Early}^i \leq 250$, $0 \leq N_{Late}^i \leq 250$, and $N_{Early}^i + N_{Late}^i = 250$, for all i.

A noise effect estimator was defined as:

$$\text{Noise Effect Estimator} = \text{standard deviation of } N_{Early}^i / (|\Sigma_i N_{Early}^i - \Sigma_i N_{Late}^i|/320) = \text{sqrt}(\Sigma_i (N_{Early}^i)^2 - (\Sigma_i N_{Early}^i)^2)/(|\Sigma_i N_{Early}^i - \Sigma_i N_{Late}^i|/320) = \text{sqrt}(\Sigma_i (N_{Early}^i)^2 - (\Sigma_i N_{Early}^i)^2)/(|\Sigma_i N_{Early}^i - 20000|/160) \quad \text{Eq(5)}$$

This "noise effect estimator" compares the variability in the number of "Early" master classifier classifications with the difference in the total numbers of "Early" and "Late" master classifier classifications. If the noise realizations produce a low variability in the number of "Early" classifications compared with the typical difference between the number of "Early" and "Late" master classifications for a realization, the noise effect estimator will be small. If the noise realizations produce a variability in the number of "Early" classifications large compared with the typical difference between the number of "Early" and "Late" master classifications for a realization, the noise effect estimator will be large.

Samples for which the difference in number of "Early" and "Late" master classifier classifications is large can tolerate substantial variability before producing a change in returned VS2.0 classification, whereas samples for which this difference is small are subject to changes in returned overall classification with only small variability. Hence, the noise effect estimator defined in Eq. 5 provides a measure of how susceptible a sample is to classification label change.

Applying this procedure to two runs of the Italian A, B, and C sample sets to calculate the noise effect estimator for each sample revealed reliable classifications could be returned for samples by returning the VS2.0 classifier classification only for samples with a noise effect estimator below a threshold of 0.5. Above this threshold there is substantial uncertainty in returning a classification label for a sample under test and an Intermediate/Unknown classification label should be reported.

Application of the Final Classifier to Samples in the Development Set

Figure 6A:
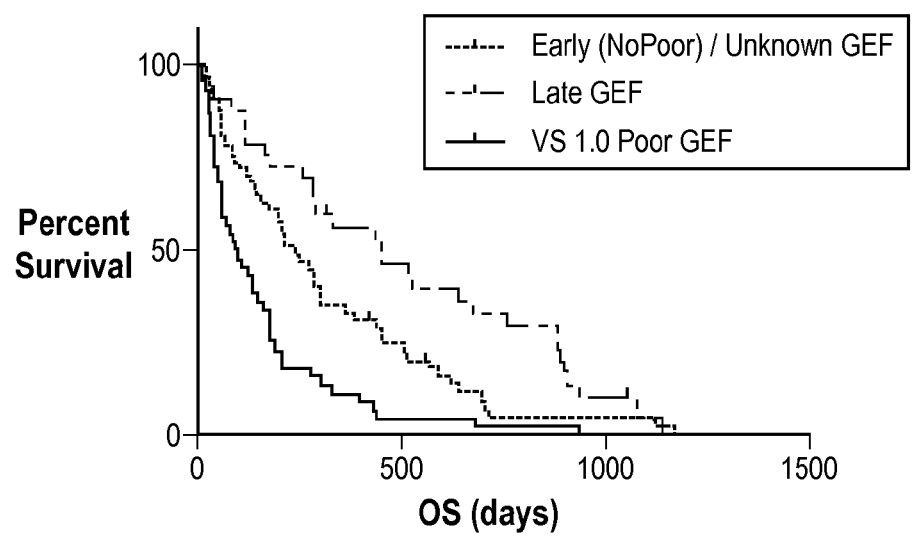
FIGS. 6A-6D are Kaplan-Meier curves showing the time-to-event outcomes of patients in the NSCLC/EGFR-I CMC/D classifier development set with labels assigned from development set spectra.
Figure 6B:
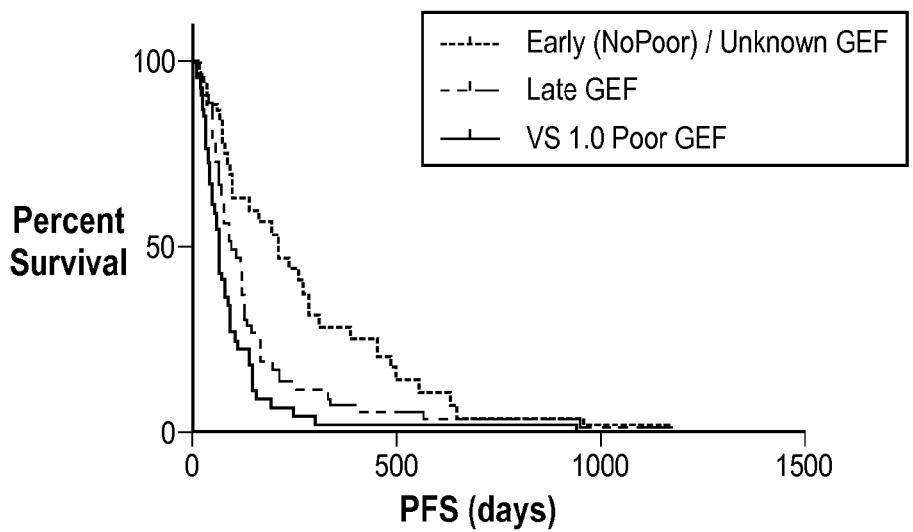
Figure 6C:
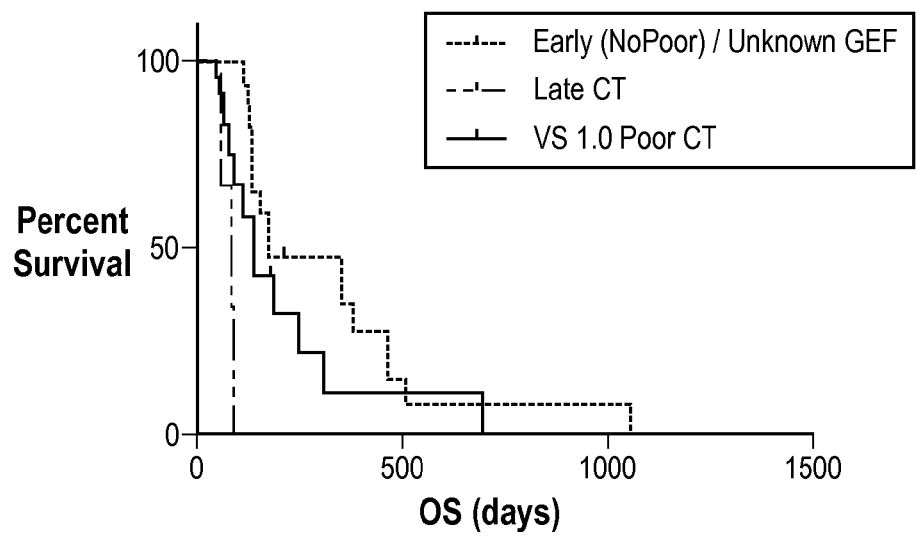
Figure 6D:
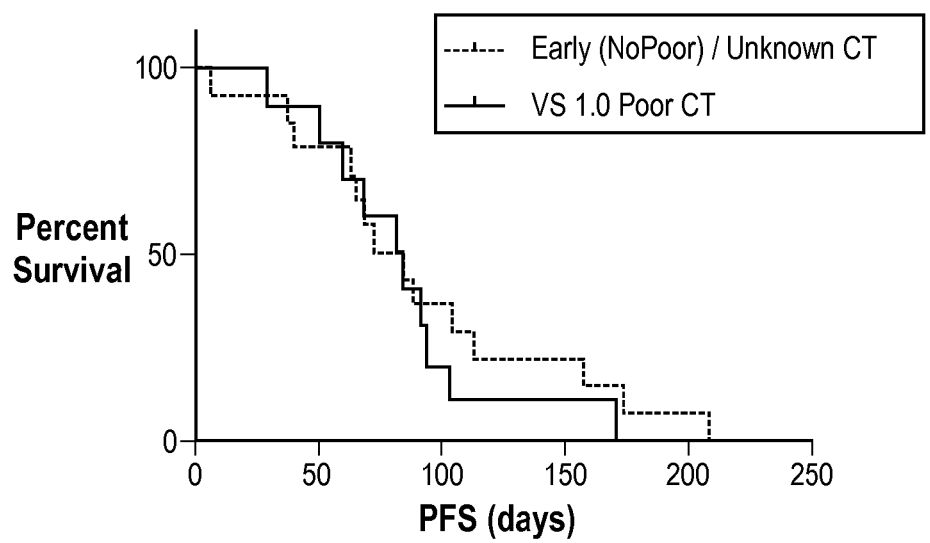

The VS2.0 final classifier was applied to all samples in the development set. Note that this includes samples included in training of the classifier. The VS2.0 classifications of the development set samples are given in Appendix E. Notice that all samples with a VS1.0 classification of Poor were assigned a label of Early. OS and PFS are plotted for patients in the development set grouped according to: Late, Unknown and Early (excluding VS1.0 Poor) and VS 1.0 Poor in FIG. 6. Note that several patients in the Italian C cohort had OS data, but no PFS data. FIG. 6 is a plot of time-to-event outcomes of patients in the development set with labels assigned from development set spectra; FIG. 6A: OS for gefitinib-treated patients, FIG. 6B: PFS for gefitinib-treated patients, FIG. 6C: OS for chemotherapy-treated patients and FIG. 6D PFS for chemotherapy-treated patients. By comparing FIGS. 6A and 6C, it is noted that those patients whose sample tested Late obtained greater benefit from gefitinib than chemotherapy, as indicated by the overall survival curves for these patients.

Survival statistics related to the plots in FIG. 6 are presented in Tables 3 and 4

TABLE 3

Medians associated with FIG. 6

| Endpoint | Group | n | Median (days) | 95% CI (days) |
|---|---|---|---|---|
| OS | Late GEF | 32 | 457 | 259-680 |
| OS | Early/Unknown GEF | 53 | 243 | 144-304 |
| OS | VS1.0 Poor GEF | 44 | 96.5 | 60-162 |
| PFS | Late GEF | 32 | 208 | 90-287 |
| PFS | Early/Unknown GEF | 53 | 92 | 69-122 |
| PFS | VS1.0 Poor GEF | 44 | 61.5 | 43-83 |
| OS | Late CT | 3 | 80 | 55-92 |
| OS | Early/Unknown CT | 17 | 172 | 132-383 |
| OS | VS1.0 Poor CT | 12 | 141 | 60-250 |
| PFS | Early/Unknown CT | 14 | 78.5 | 40-113 |
| PFS | VS1.0 Poor CT | 10 | 82.5 | 29-93 |

TABLE 4

Hazard Ratios and p values associated with FIG. 6

| Endpoint | Comparison | log-rank p | Cox HR (95% CI) | CPH p value |
|---|---|---|---|---|
| OS | GEF: Early/Unk vs Late | 0.025 | 0.59 (0.37-0.94) | 0.027 |
| OS | GEF: Poor vs Late | <0.001 | 0.30 (0.18-0.49) | <0.001 |
| OS | GEF: Poor vs Early/Unk | <0.001 | 0.49 (0.33-0.75) | <0.001 |
| PFS | GEF: Early/Unk vs Late | 0.018 | 0.58 (0.37-0.91) | 0.018 |
| PFS | GEF: Poor vs Late | <0.001 | 0.36 (0.22-0.60) | <0.001 |
| PFS | GEF: Poor vs Early/Unk | 0.025 | 0.64 (0.42-0.95) | 0.029 |
| OS | CT: Poor vs Early/Unk | 0.217 | 0.61 (0.28-1.35) | 0.221 |
| PFS | CT: Poor vs Early/Unk | 0.477 | 0.74 (0.31-1.72) | 0.479 |

Samples from Italian A, B and C were rerun twice. (In the last run only the VS1.0 Good samples were rerun and a few samples were omitted due to lack of remaining sample volume.) The results across the three runs are summarized in Appendix F.

The sensitivity corrections together with the in-silico noise analysis led to good reproducibility of actionable labels. Of the 93 samples run in the last run 16 were labeled Late, 35 were labeled Early, and 42 were labeled Unknown. The samples labeled as Late in the third run they were either labeled as Late or Unknown in the previous runs. The samples labeled as Early in the third run were either labeled as Early or as Unknown in the previous runs. 24 of the 35 samples labeled as Early in the third run were labeled as Early in all three runs. 14 of the 16 samples labeled as Late in the third run were labeled as Late in all three runs. 20 of the 42 samples labeled as Unknown in the third run were labeled as unknown in all three runs. While the large proportion of Unknowns is undesirable, it does appear that if we call a label of Early (Late) from a VS2.0 analysis, this sample would be characterized as Early (Late) in another run, or be called Unknown.

Application of the Final CMC/D Classifier to Samples from the PROSE Study

Testing Procedure: Blinding

The final CMC/D classifier described above was subject to a test on mass spectra obtained from available samples from the PROSE study under a validation protocol. The final CMC/D classifier was deemed fixed prior to this validation protocol. Mass spectra were provided to analysts blinded to their clinical data. The spectra were analyzed as described above and the resulting classifications (Appendix G) were generated. An un-blinding key was then provided and a statistical analysis was carried out.

Testing Procedure: m/Z Sensitivity Correction Calculation

Figure 7:
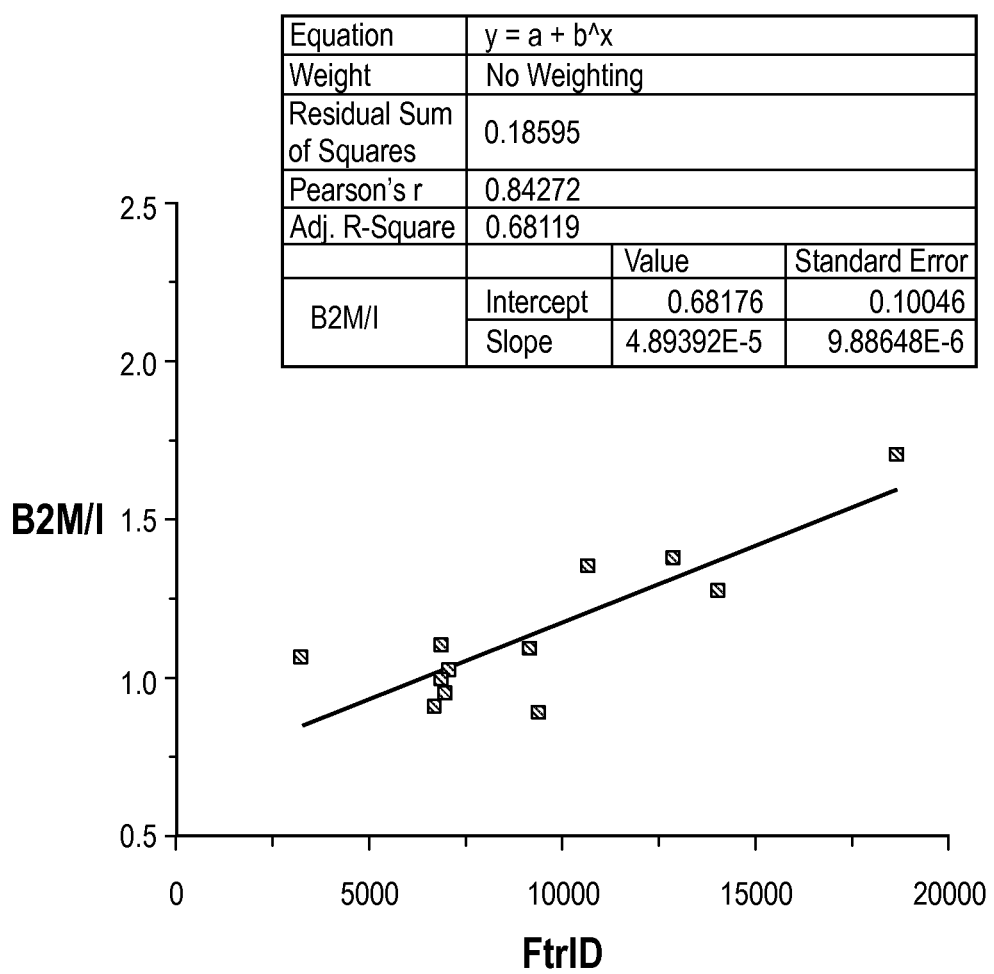
FIG. 7 is a plot of the regression curve for sensitivity correction for the NSCLC/EGFR-I CMC/D classifier applied to the PROSE sample set.

The serum P2 (reference) spectra generated together with the PROSE spectra were analyzed to provide the necessary m/z sensitivity correction. As the PROSE samples spanned 5 batches, one preparation of serum P2 was collected with each batch. With 5 separate preparations, the CV calculation approach (outlined above) was used. The regression curve for PROSE data is shown in FIG. 7. From this curve, Y axis intercept and slope values were obtained as indicated in the inset to FIG. 7.

Statistical Analysis of Results

The VS2.0 classifications obtained for the samples from the PROSE trial are listed in Appendix G. Only samples from patients in the PROSE primary analysis population were considered for statistical analysis. For patient 01_044 and patient 01_080, two samples were available. The results for the sample with the standard labeling, rather than the sample labeled as 'second sample', were used for the statistical analysis. Two samples were also available for patient 06_010, but both had VS2.0 classification of Early. No samples were available for patient 01_050, patient 03_006, patient 06_004, patient 06_021, patient 11_043, patient 11_048, and patient 12_014.

Hence samples were available from 256 of the 263 patients in the PROSE per-protocol population: 148 were classified as Early, 39 as Late, and 69 as Unknown. All of the samples classified as Late were associated with patients with VS1.0 Good classification. Only two of the patients classified in the PROSE primary analysis as VS1.0 Poor were classified as Unknown; all others were classified as Early. Of the 148 patients classified as Early, 73 had VS1.0 classification of VS Good and 75 had VS1.0 classification of VS Poor.

Patient characteristics by VS2.0 classification are shown in Table 5.

TABLE 5

Patient characteristics by VS2.0 classification within VS1.0 Good population

| | | Late (N = 39) | Early/Unknown (N = 140) | p value |
|---|---|---|---|---|
| Histology | Adeno | 27 (69%) | 93 (67%) | 0.100 |
| | Squamous | 2 (5%) | 24 (17%) | |
| | BAC | 2 (5%) | 1 (1%) | |

TABLE 5-continued

Patient characteristics by VS2.0 classification within VS1.0 Good population

| | | Late (N = 39) | Early/Unknown (N = 140) | p value |
|---|---|---|---|---|
| | Large | 2 (5%) | 8 (6%) | |
| | NOS | 2 (5%) | 4 (3%) | |
| | Other/Missing | 4 (10%) | 10 (7%) | |
| Gender | Male | 26 (67%) | 94 (67%) | >0.99 |
| | Female | 13 (33%) | 46 (33%) | |
| Smoking Status | Never | 7 (18%) | 23 (16%) | 0.968 |
| | Former | 23 (59%) | 82 (58%) | |
| | Current | 9 (23%) | 35 (25%) | |
| PS | 0 | 24 (62%) | 81 (58%) | 0.491 |
| | 1 | 15 (38%) | 52 (37%) | |
| | 2 | 0 (0%) | 7 (5%) | |
| EGFR mutation | Mutation | 5 (16%) | 7 (7%) | 0.159 |
| | WT | 24 (75%) | 84 (86%) | |

Figure 8A:
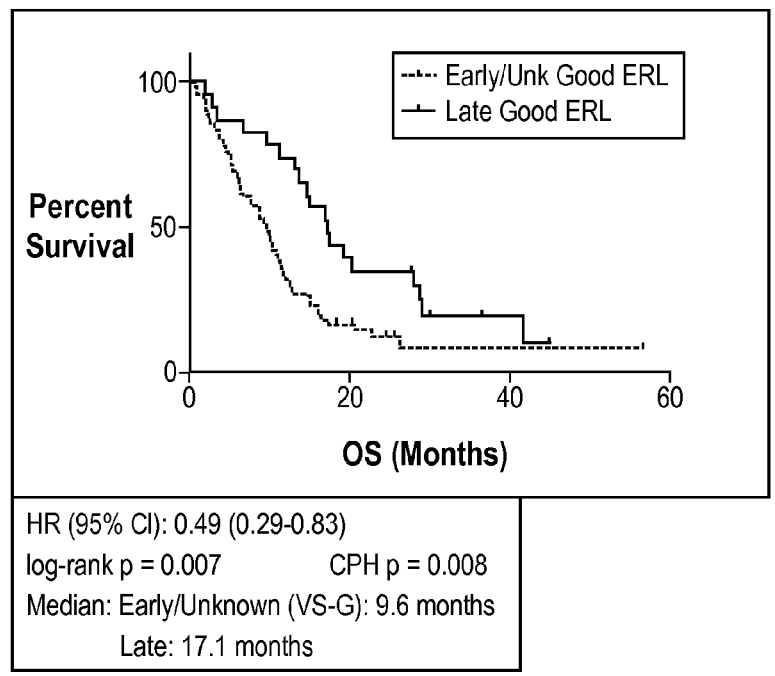
FIGS. 8A and 8B are Kaplan-Meier plots of overall survival for the groups Late and Early/Unknown (those patients testing VeriStrat Good in the original VeriStrat test) for patients treated with erlotinib (FIG. 8A) and chemotherapy (FIG. 8B).
Figure 8B:
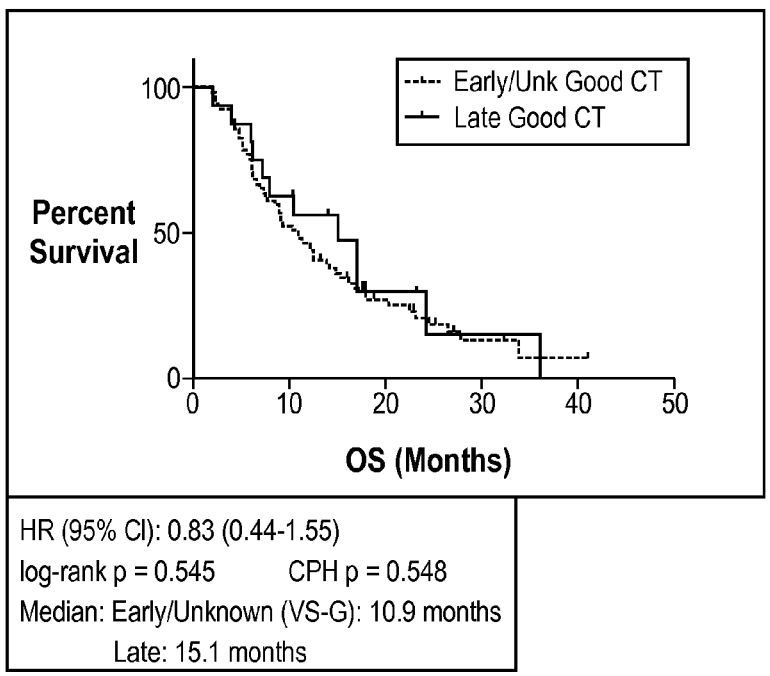
Figure 9A:
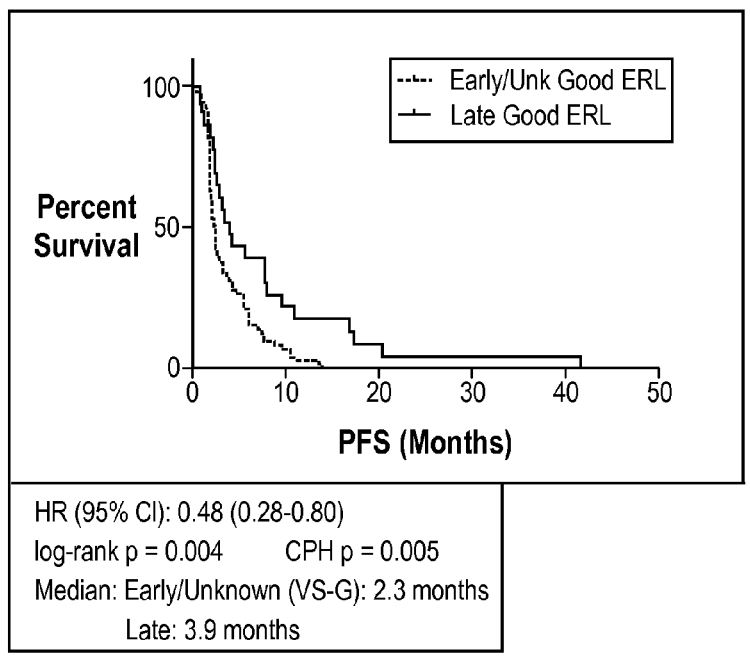
FIGS. 9A and 9B are Kaplan-Meier plots of progression-free survival for the groups Late and Early/Unknown (those patients testing VeriStrat Good in the original VeriStrat test) for patients treated with erlotinib (FIG. 9A) and chemotherapy (FIG. 9B).
Figure 9B:
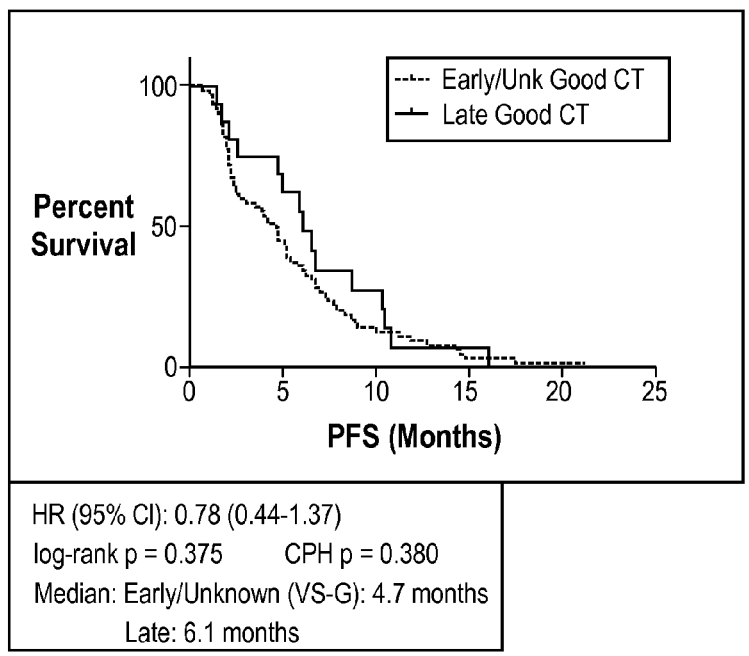

FIG. 8 shows the OS results for the classification groupings Late and Early/Unknown (VS1.0 Good) by treatment, with FIG. 8A showing the data for the erlotinib treatment group and FIG. 8B showing the data for the chemotherapy treatment group. FIG. 9 shows the PFS results for the classification groupings Late and Early/Unknown (VS1.0 Good) by treatment, with FIG. 9A showing the data for the erlotinib treatment group and FIG. 9B showing the data for chemotherapy treatment group.

The results of a multivariate analysis of the VS1.0 Good population are shown in Table 6. VS2.0 result of Late or Early/Unknown remains significant when adjusted for possible confounding factors.

TABLE 6

Multivariate analysis of VS1.0 Good population

| Endpoint | Covariate | HR (95% CI) | p value |
|---|---|---|---|
| OS | Treatment: CT vs ERL | 1.12 (0.85-1.65) | 0.320 |
| | VS2.0: Early/Unknown vs Late | 0.59 (0.39-0.89) | 0.012 |
| | Gender: Male vs Female | 0.83 (0.57-1.20) | 0.316 |
| | PS: 0-1 vs 2 | 1.87 (0.86-4.08) | 0.114 |
| | Smoking Status: Never vs Ever | 1.23 (0.75-2.00) | 0.411 |
| PFS | Treatment: CT vs ERL | 1.43 (1.05-1.93) | 0.023 |
| | VS2.0: Early/Unknown vs Late | 0.57 (0.39-0.83) | 0.004 |
| | Gender: Male vs Female | 1.06 (0.75-1.48) | 0.759 |
| | PS: 0-1 vs 2 | 1.30 (0.60-2.81) | 0.500 |
| | Smoking Status: Never vs Ever | 1.31 (0.85-2.02) | 0.230 |

Figure 10:
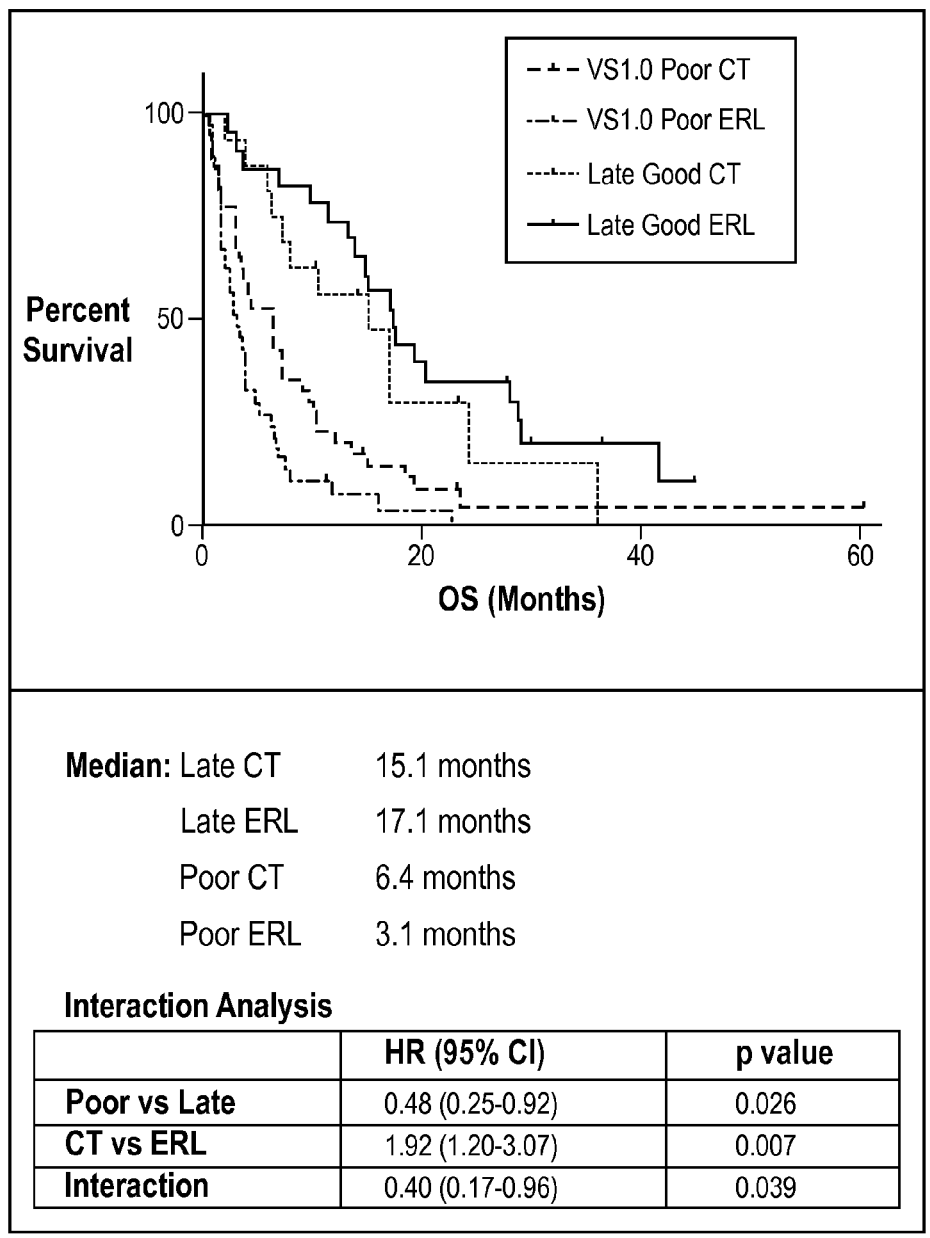
FIG. 10 is a Kaplan-Meier plot of overall survival for patients classified as VeriStrat Poor and Late by treatment.

FIG. 10 shows the Kaplan-Meier plots of OS for the groups VS1.0 Poor and Late by treatment along with the results of the analysis of interaction between classification, VS1.0 Poor and Late, and treatment.

FIG. 11 compares outcomes between chemotherapy and erlotinib within the VS1.0 Good Early/Unknown group.

Figure 12A:
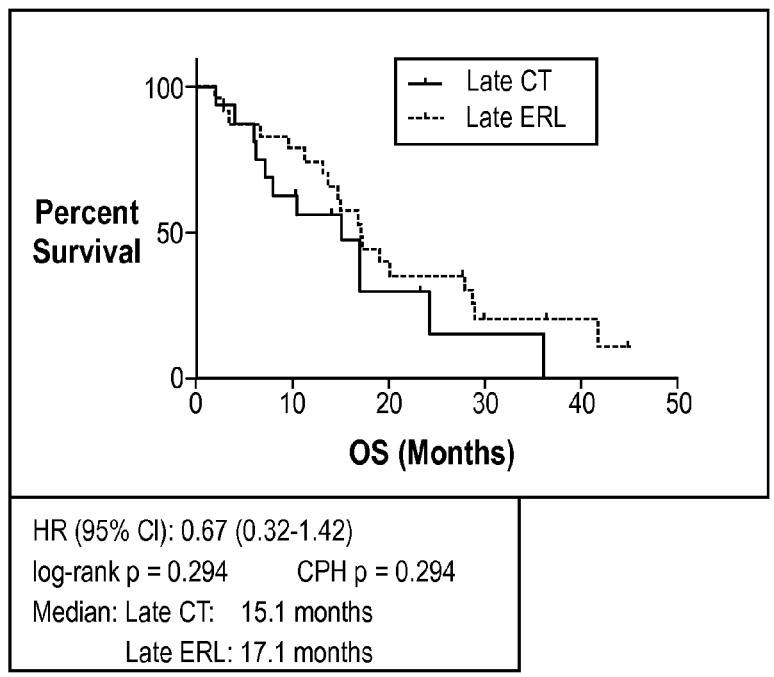
FIG. 12A is a Kaplan-Meier plot of OS within the late group by treatment.
Figure 12B:
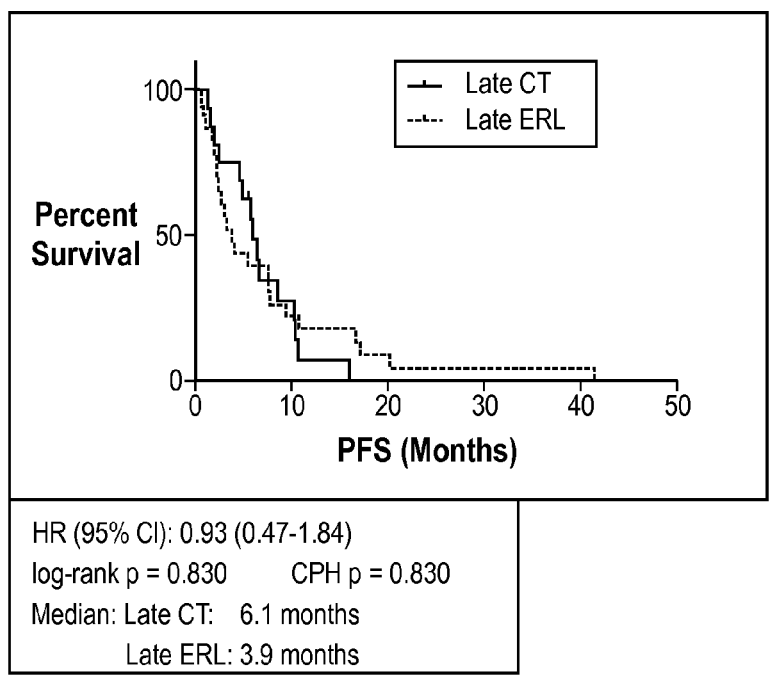
FIG. 12B is a Kaplan-Meier plot of PFS within the late group by treatment.

A comparison of outcomes within the Late group by treatment is shown in FIG. 12. Note that in FIG. 12A, those patients classified as Late and receiving erlotinib had a median overall survival time of 17.1 months, two months greater than those patients receiving chemotherapy.

The medians for OS and PFS for each group are summarized for each treatment arm, along with their 95% confidence interval and the number of patients in each group in Table 6.

Table 6 Medians for OS and PFS by group and treatment arm

| Endpoint | Group | n | Median (months) | 95% CI (months) |
|---|---|---|---|---|
| OS | Late CT | 16 | 15.1 | 6.2-24.2 |
| OS | VS1.0 Poor CT | 40 | 6.4 | 3.3-7.4 |
| OS | Early/Unknown (VS1.0 Good) CT | 69 | 10.9 | 7.4-14.1 |
| OS | Late ERL | 23 | 17.1 | 13.1-27.9 |
| OS | VS1.0 Poor ERL | 37 | 3.1 | 2.0-4.0 |
| OS | Early/Unknown (VS1.0 Good) ERL | 71 | 9.6 | 6.3-11.0 |
| PFS | Late CT | 16 | 6.1 | 2.6-10.4 |
| PFS | VS1.0 Poor CT | 40 | 2.8 | 1.9-4.5 |
| PFS | Early/Unknown (VS1.0 Good) CT | 69 | 4.7 | 2.5-5.4 |
| PFS | Late ERL | 23 | 3.9 | 2.4-7.8 |
| PFS | VS1.0 Poor ERL | 37 | 1.7 | 1.5-2.2 |
| PFS | Early/Unknown (VS1.0 Good) ERL | 71 | 2.3 | 2.0-2.8 |

Section II Conclusions

The test described in this section (VS 2.0) is a truly multivariate test utilizing 74 features derived from a mass spectrum of a blood-based sample to identify a group of 2nd line NSCLC patients having superior performance on erlotinib over chemotherapy. The development of this test has validated the CMC/D classifier development methodology. VS2.0 separates the group we previously identified as "Good" in the original VeriStrat test group into two subgroups, "VS2.0 Early" or "Early" and "VS2.0 Late" or "Late", albeit with a substantial group of unidentifiable patients, described here as "VS2.0 Unknowns", due to limitations of spectral acquisition.

In its current implementation, this test (VS2.0) relies on spectral acquisitions on machines qualified for our original VeriStrat test. As VS2.0 requires feature values from m/z ranges outside of the VS1.0 validation regime, special care needs to be taken to correct for differences in m/z dependent sensitivity by utilizing reference samples. Label stability is assessed using in-silico sensitivity analysis, which leads to a substantial number of VS2.0 Unknowns. The reproducibility of assigned VS2.0 labels in terms of assigning only sure labels has been assessed by three runs of the development set, and is very high. For clinical use of VS2.0 we analyzed three groups: VS2.0 Late, VS2.0 Early and Unknowns in the VS1.0 good population, and VS1.0 Poors which classify almost uniformly as VS2.0 Early.

VS2.0 was qualified (clinically validated) in a blinded analysis of the PROSE samples. The available number of samples in the VS2.0 Late group limited the significance of this qualification in some aspects. Comparing overall survival in VS2.0 Lates to VS2.0 Early/unknowns in the VS1.0 Good group shows that VS2.0 splits the VS1.0 good group into a well and poor performing group under erlotinib treatment, while there is little evidence for such a split in the chemotherapy arm. Unfortunately the sample size was too small to achieve statistical significance for a superiority of erlotinib over chemotherapy. VS2.0 retains the predictive power of VS1.0 (VS2.0 Late vs. VS1.0 Poor by treatment) even though the sample size was halved. The results on PFS are similar than in OS.

The successful development of VS2.0 validates the correlational approach to test development, and the CMC/D methodology in general. The parallel iterative development of training labels and a test to identify such patients has worked surprisingly well. The measures inherent in CMC/D to avoid overfitting have been proven valid, and been extended to include majority votes over training/test split MCs further reducing ambiguity in test/final classifier selection. VS2.0 utilizes around 60% of observable peaks in the summed spectra we used (3 replicates of a 2,000 shot spectrum) with no clear favorite features. Hence, while the present example makes use of the particular features noted in Appendix B, these specific features are not believed to be essential or critical and well performing tests could be based on a subset of these features or possibly additional features, e.g., discovered by spectra obtained from a greater number of shots.

In terms of commercial use VS2.0 provides a tool to identify a group of patients for which one can be reasonably certain that erlotinib is at least equivalent to chemotherapy, and likely to be superior. Medians of 17 months overall survival in a second line setting are spectacular, and might lead to changes in treatment regime in 2nd line NSCLC. Again, we were able to define the class labels "Early" and "Late" (or the equivalent) that enable this prediction as a part of this process.

Section III Use of VS 2.0 CMC/D Classifier in a Testing Environment (FIG. 2)

The application of the CMC/D classifier as described in Section II to classify a blood-based sample from a NSCLC patient will be described in this section in conjunction with FIG. 2. As explained above, if the class label assigned to the test sample is "Late" or the equivalent, the class label predicts that the NSCLC patient providing the sample is more likely to benefit from an EGFR-I such as erlotinib or gefitinib as compared to chemotherapy. The patient whose test sample has the "Intermediate" label associated with it is predicted to obtain a similar clinically meaningful benefit from chemotherapy and EGFR-Is.

In one possible implementation of the method, the mass spectrum from the sample is first subject to the VS 1.0 test described in U.S. Pat. No. 7,736,905, and if the Poor label is assigned to the sample, that test label is reported. The patient with this label is predicted to not obtain benefit from an EGFR-I in treatment of the patient. If the label is VS Good or the equivalent, the sample spectrum is then subject to the testing process of VS 2.0 shown in FIG. 2, in order to determine whether the patient has the "Late" label, in which the patient is predicted to obtain greater benefit from an EGFR-I such as erlotinib or gefitinib as compared to chemotherapy, or conversely have has "Intermediate" class label, in which the patient is predicted to obtain a similar clinically meaningful benefit from chemotherapy and EGFR-Is. A third class label is contemplated, namely "unknown" or "indeterminate" in which it cannot be predicted whether the patient is likely to obtain benefit from EGFR-I as compared to chemotherapy, The workflow showing use of the CMC/D classifier generated in accordance with FIG. 1 on a mass spectrum of a test sample is shown in FIG. 2. The process begins with providing three blood-based samples to a mass spectrometer: a test sample 1200 from a patient for whom the test is being performed, and two reference sample aliquots shown as Reference Sample 1 and Reference Sample 2, items 1202A and 1202B, respectively. These two reference samples are two aliquots from the reference blood-based sample from a healthy human patient. The reference samples 1202A and 1202B are used in this embodiment in order to correct for m/z sensitivity variations over m/z ranges that are outside of previously qualified m/z ranges for the particular mass spectrometer that was used in the VS 1.0 test. It is possible that with appropriately qualified machines the use of reference samples 1 and 2 would not be necessary.

At step 1204, mass spectrometry on the three samples 1200, 1202A and 1202B is performed using a MALDI-ToF mass spectrometer. Each sample is subject to 2000 shot "dilute and shoot" MALDI-ToF mass spectrometry in the instrument three times with spectral acquisition filtering (see previous discussion). The resulting three 2000 shot spectra for each of the three samples are transferred from the mass spectrometer to machine-readable memory of a general purpose computer implementing the workflow of FIG. 2.

Figure 13:
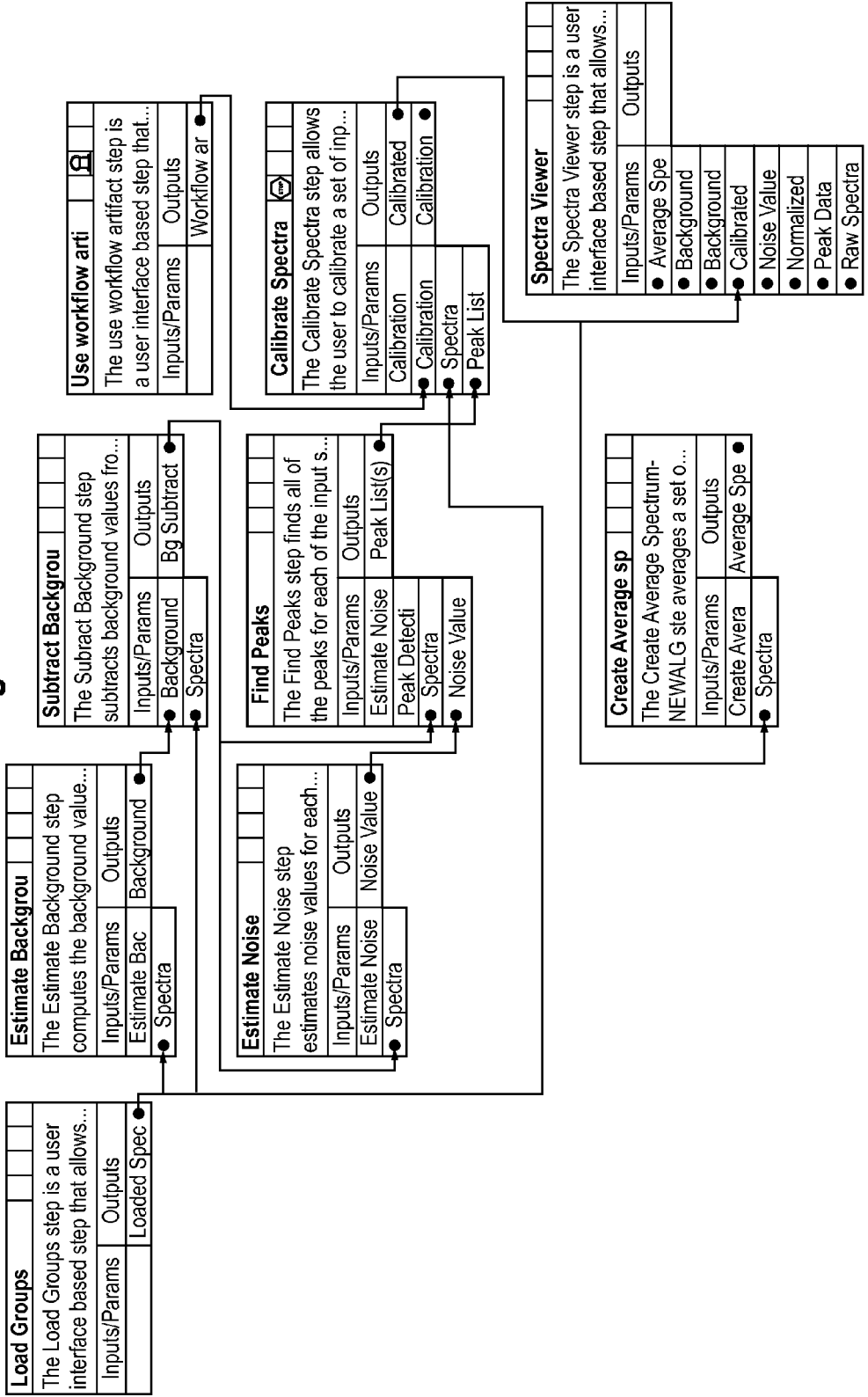
FIG. 13 is an illustration of the averaging workflow module 1206 of FIG. 2.

A software module Averaging Workflow 1206 is then invoked to perform an averaging of the triplicate spectra obtained at step 1204, indicated at step 1208. The averaging workflow is shown in FIG. 13. Basically, this module estimates peaks in the spectra that are used for alignment, performs an alignment of the raw spectra, and then computes the average values of the aligned spectra from the three replicates from each of the three samples.

Figure 14:
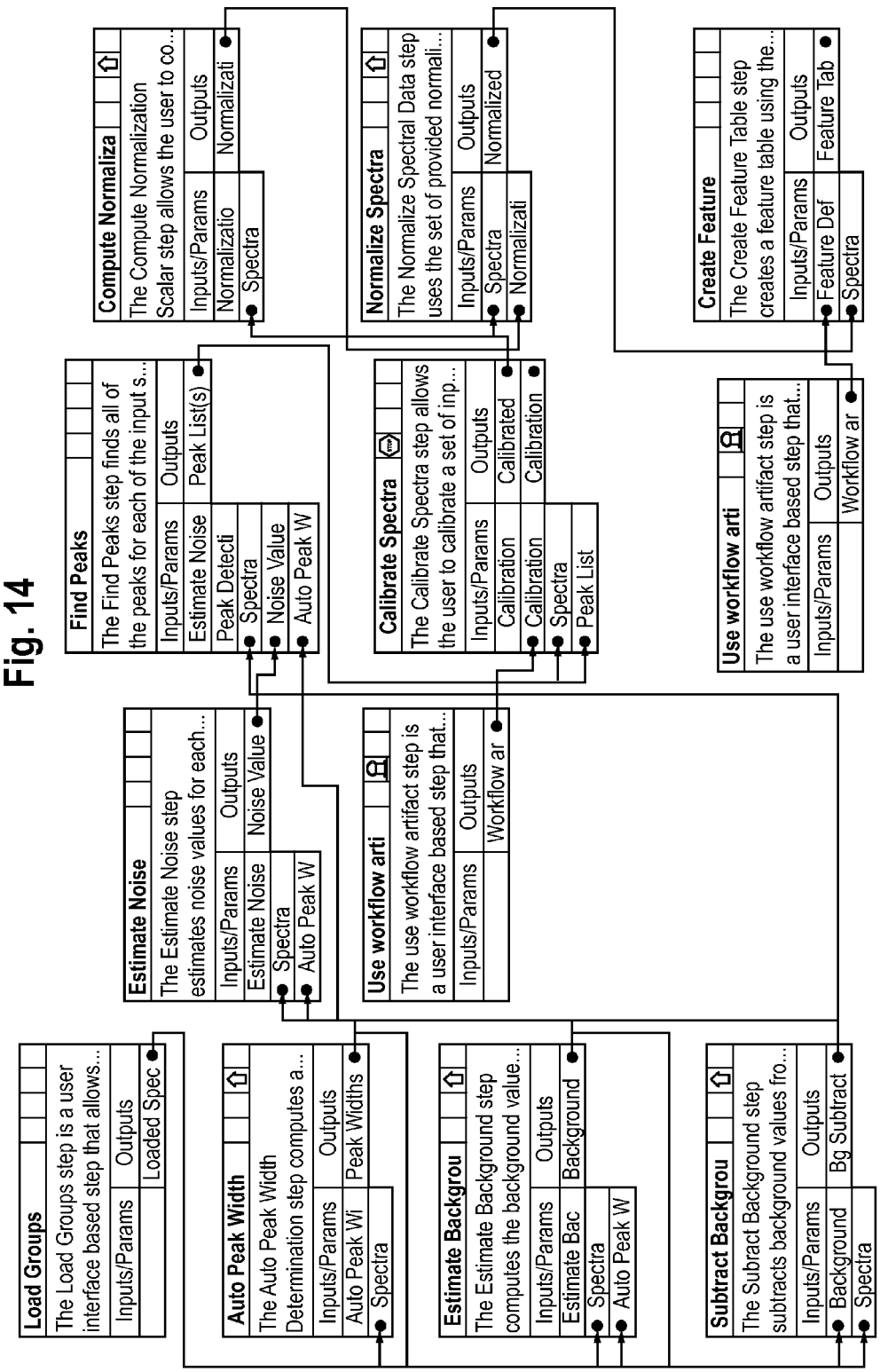
FIG. 14 is an illustration of the pre-processing workflow module 1212 of FIG. 2.

A Pre-processing Workflow module 1212 (FIG. 14) is then invoked to perform pre-processing of the averaged spectra and to generate feature values (a feature table) for use in classification as indicated at step 1214. The step includes background subtraction and estimation, peak detection and alignment, partial ion current normalization, and calculation of feature values (integrated intensity values) over pre-defined m/Z ranges. The ranges are listed in Appendix B.

As indicated at 1216, the feature values for the two reference samples (1202A and 1202B) generated at step 1214 are provided to a module 1218 which checks to see if the reference values are concordant. Basically, in module 1218, a comparison of the reference feature values are performed. This involves the following:

1. Calculate parameter $\delta_F$=min (|1−(FVpre/FVpost)|, |1−(FVpre/FVpost)|) for all feature values F obtained at step 1214. The idea here is to run one reference sample (1202A) before the test sample 1200 (or at the beginning of a batch of test samples), and obtain the set of feature values from the reference sample i.e. $FV_{pre}$, and then run another preparation of the reference sample 1202B after the test sample 1202 (or at the end of the batch of test samples), and obtain the set of feature values from the reference sample again i.e. $FV_{post}$.
2. Select those features where $\delta_F$ is <0.1, Add those feature values to a list of feature values (list L).
3. Compare the list of features L selected at 2 with the list of feature values, L', obtained from the same steps 1-2 from the reference samples run with the development set of samples used to generate the CMC/D classifier (i.e., the list of features in Appendix B.)
4. If list L contains the feature at m/Z positions 3219 and 18634, these feature values are considered concordant.

If the concordance test (4.) fails, the process goes back to the beginning and the spectra acquisition of the test sample and the two reference samples is redone. If the concordance test (4.) succeeds, the processing proceeds to the define feature correction function step 1222 using the standard set of feature values 1220. These are the feature values for the two preparations of the reference sample (1201A and 1202B) that were run with the development set samples when the original spectra were generated (i.e., at time of generation of the CMC/D classifier). It can be a list of all the feature values, but some do not pass the concordance criteria that we have set up between the two preparations, and so these features would never be used in practice and would be excluded from the list. We look for features that are consistent (concordant) between the two preparations of the reference sample run with the development set spectra and also concordant for the pre- and post-reference spectra. Then, we calculate the averages of the original samples and the averages of the pre- and post-samples for these features. We work out the ratio of these two and plot it as a function of m/Z. A linear regression of the graph of ratios is generated and the Y axis intercept and slope are returned. See the discussion of FIG. 5, supra.

At step 1224, the Y axis intercept and slope from step 1222 are feature value correction function parameters a and b, respectively, from the linear regression plot. These values are applied to the test sample feature values generated at step 1214. This correction can be expressed as follows:

$$FV_{corrected} = FV_{estimated}/(a+bm_Z)$$

At step 1224, these corrected feature values are stored in memory. The corrected feature values are used in two separate processing branches: steps 1228 and in step 1232.

In step 1228, the data set representing the final CMC/D classifier 1226 generated in accordance with the procedure of FIG. 1 is applied to the corrected test sample feature values. In this example, the final CMC/D classifiers is the set of 250 master classifiers generated in each of the test and training sample splits realizations from the classifier generation sample set 1100 (FIG. 1) and created at step 1134 of FIG. 1. The result of this application of the master classifier to the corrected feature values is a test sample classification label, as indicated at 1229.

As indicated in FIG. 2 at 1232, the corrected feature values generated at step 1224 are also sent to a module 1232 which generates new feature value realizations ("noise realizations") making use of pre-defined feature-dependent noise characteristics 1230. Basically, this module 1232 uses noise parameters a, obtained from the development sample set (FIG. 1, 1100) to generate 160 noise realizations:

Additive Noise Realizations:

$$FVN_i = FV_{corrected,i} + \epsilon_i$$

Multiplicative Noise Realizations:

$$FVN_i = FV_{corrected,i} * (1+\epsilon_i)$$

where $\epsilon_i$ is a Gaussian random number (N) with zero mean and unit standard deviation characterized by the expression N (0, $\sigma_i$) where $\sigma_i$ are noise parameters determined from the development set as described previously.

The resulting "noise" feature values generated in step 1232 are in the form of a feature table. All the feature values are provided as workflow artifacts. The results of this process are stored in convenient form, such as Excel spreadsheets.

Figure 15:
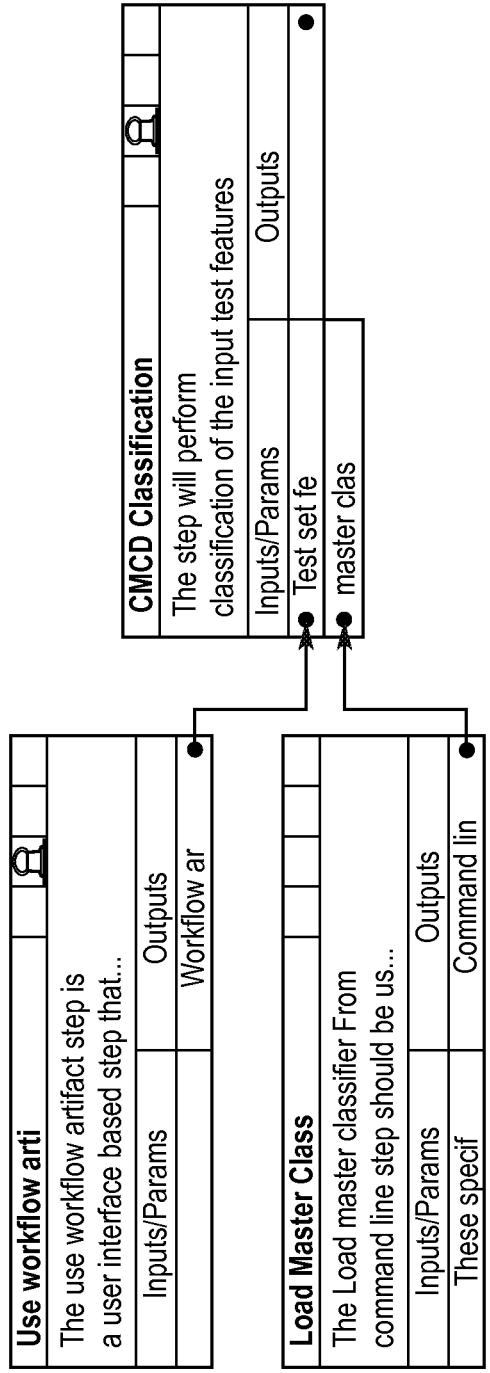
FIG. 15 is an illustration of the modules 1228 and 1234 of FIG. 2 that apply the master classifier to the corrected test sample feature values and the noisy feature value realizations.

At step 1234, the data set representing the master classifier (1226, described above) is applied to the noisy feature values generated in step 1232. See FIG. 15. This results in a table of master classifier results (# of class labels of each type). In this particular example, where the master classifier takes the form of 250 master classifiers resulting from 250 training/test set splits (as explained above), there are 250 class labels generated for each noise realization. The master classifier results for the noise realizations are collated as indicated at step 1236 so that statistical data on the classification results can be obtained as indicated as 1238. In this step 1236 we generate the ratio R (referred to as the "noise effect estimator") which is related to the standard deviation of the difference between the number of Late and Early classifications. This is done over all the noisy realizations of the feature table. The particulars of this statistical analysis and computation of ratio R is as follows:

let $N_{Early}^i$ = # of Early classifications across the 250 master classifiers (MCs) calculated for each noise realization, i, for the test sample (1≤i≤160 in this example since there are 160 different noise realization). Compute sum over all i, $\Sigma_i N_{Early}^i$.

let $N_{Late}^i$ = # of Late classifications across the 250 master classifiers (MCs) calculated for noise realization, i, for the test sample (1≤i≤160). Compute sum over all i, $\Sigma_i N_{Late}^i$.

So, $0 \leq N_{Early}^i \leq 250$ and $0 \leq N_{Late}^i \leq 250$ for all i.

And $N_{Early}^i + N_{Late}^i = 250$, for all noise realizations i.

Noise Effect Estimator=R=standard deviation of $N_{Early}^i/(|\Sigma_i N_{Early}^i - \Sigma_i N_{Late}^i|/320)$=sqrt($\Sigma_i(N_{Early}^i)^2 - (\Sigma_i N_{Early}^i)^2)/(|\Sigma_i N_{Early}^i - \Sigma_i N_{Late}^i|/320)$=sqrt($\Sigma_i (N_{Early}^i)^2 - (\Sigma_i N_{Early}^i)^2)/(|\Sigma_i N_{Early}^i - 20000|/160)$ The denominator in R, $(|\Sigma_i N_{Early}^i - \Sigma_i N_{Late}^i|/320)$, gives a measure of the average difference between the numbers of Earlys and Lates that we get across the 160 noise realizations. If this number is small then the majority vote classification was close, and if it is big, it was a one-sided vote. In essence, the ratio R compares the variability in the MC labels with how one-sided it is, which is important because we want to know whether the variability we measure in noise parameter $\epsilon$ is likely to lead to an unreliable majority vote classification. That is, we do not mind a variability of say 10, if we average 220 Earlys and 30 Lates over all the 250 MCs, but we do mind a variability of 10 if we average 130 Earlys and 120 Lates over all the 250 MCs.

The final classification label for the test sample (1200, FIG. 2) is generated at step 1240. In the illustrated embodiment, this classification will only be performed on samples with a VS1.0 classification of Good; i.e., a preliminary test is done using VS 1.0 and if the patient tests VS Poor, that label is reported. The final classification label which is reported is as follows:

1. If the ratio R determined in step 1236 is >0.5, return the label Intermediate (or the equivalent). The patient whose sample has the Intermediate label associated with it is predicted to obtain a similar clinically meaningful benefit from chemotherapy and EGFR-Is. Note that this is regardless of the class label produced by the master classifier on the corrected feature values (1129).

2. If the ratio R determined in step 1236 is <0.5,

A. return the Late label if the test sample label generated at 1229 is Late.

B. return the Early label if the test sample label generated at 1229 is Early.

The patient, whose test sample has the Late label in 2.A, is predicted to obtain greater benefit from EGFR-Is as compared to chemotherapy for treatment of NSCLC cancer.

In one possible embodiment the Intermediate label is deemed to comprise those patients in which the noise effect estimator >0.5 (1. above) plus the Earlys (<=0.5 noise effect estimator and Early label). They are combined because this is clinically useful (they consists essentially of those patients leftover if you decide to give the Lates EGFR-Is and those testing as VS1.0 Poor chemotherapy. The result that the outcomes may be similar on chemotherapy and TKIs was concluded for this combined group (noise effect estimator >0.5 (1. above) plus the Earlys (<=0.5 noise effect estimator and Early label), not either group separately.

Section IV Practical Examples of Tangible Systems for Generating CMC/D Classifiers and Conducting Predictive Tests Classifier Generation System and Sample Testing System The CMC/D classifier development methodology described in Sections I and II can be implemented as a tangible classifier development system in the form of a mass spectrometer (or other measuring instrument) which is used to obtain mass spectral (or other) data from a plurality of samples (e.g., a development set of samples) and a general purpose computer having a processing unit which executes code implementing the CMC/D classification method. In particular, the computer includes a machine-readable memory (e.g., hard disk) storing the measurement data. The computer also stores executable code which performs pre-processing of the measurement data, e.g., background subtraction, spectral alignment and normalization, as described above, and stores integrated intensity values at particular features used for classification, such as for example the integrated intensity values for the features listed in Appendix B.

The computer also stores executable code for constructing a multitude of individual mini-classifiers using sets of features from the samples up to a pre-selected feature set size (s, integer). In one embodiment, the code includes a KNN classification algorithm (known in the art) which is applied to a feature or features in the mass spectrometry data and compares the feature values to a subset of the development set of samples (e.g., a training set of class-labeled mass spectral data). The KNN algorithm generates a class label based on nearest neighbors in the feature space.

The code then tests the classification accuracy, or some alternative performance metric, of each of the individual mini-classifiers to classify the biological samples in a given set of samples (e.g., the training set) and retains those mini-classifiers whose performance exceeds a pre-defined threshold or is within pre-defined limits to arrive at a filtered set of mini-classifiers.

The code then repeatedly conducts a logistic training of the filtered set of mini-classifiers to the classification labels (using equation 1) for the samples using extreme dropout, by randomly selecting a small fraction of the filtered mini-classifiers and conducting logistical training on such selected mini-classifiers.

The code then proceeds to generate a final classifier, e.g., as an average over all the logistic regression trainings of the dropout iterations. In one example, the final classifier is represented in the computer memory as a weighted combination of the mini-classifiers using a single feature for classification (s=1) and the mini-classifiers using two features for classification (s=2) which passed the filtering criteria.

The final classifier can be evaluated against a test set split or subset of the development set, the evaluation also carried out over multiple different splits of the development set into training and test sets, and the final classifier can be generated by selecting one of the master classifiers resulting from a particular training and test set split, or alternatively by retaining all of the master classifiers from each training and test set split and using a majority vote from each of the master classifiers to assign a label to a sample under test.

This final classifier is then used for classification of a test sample, e.g., a blood-based sample of a NSCLC cancer patient, to predict in advance of treatment whether the NSCLC patient is likely to benefit from an EGFR-I. If the class label assigned to the mass spectrum of the sample is Late, that means the patient is likely to benefit.

The classification system described above can be implemented at a laboratory test center testing samples commercially and providing a service for clinics, hospitals, oncologists and other health care providers with test results as to patient benefit from cancer-targeting drugs. Of course, the classifier development methodology can be used for other purposes, such as diagnostic purposes.

Testing System

FIG. 16 is an another example of a tangible system for processing a test sample using a classifier generated in accordance with FIG. 1, including a mass spectrometer 2606 and a general purpose computer 2610 implementing a CMC/D classifier 2620 coded as machine-readable instructions and a feature table 2622 forming a training set of class-labeled mass spectrometry data 2622 stored in memory 2614. It will be appreciated that the measurement instrument 2606 and computer 2610 of FIG. 16 could be used to generate the CMC/D classifier in accordance with FIG. 1.

In the specific embodiment of Section III, the mass spectrometer and computer 2610 implement the workflow shown in FIG. 2 and described at length above.

An alternative embodiment will now be described. The system of FIG. 16 obtains a multitude of samples 2600, e.g., blood-based samples (serum or plasma) from cancer patients. The samples 2600 are used to make predictions as to whether the patient is likely to benefit or not benefit from a particular drug or combination of drugs. The samples may be obtained as serum cards or the like in which the blood-based sample is blotted onto a cellulose or other type card. Three aliquots of the sample are obtained. In one possible embodiment (as described in Section III), a reference sample 2604 may also be used.

The three aliquots of the sample are spotted onto a MALDI-ToF sample "plate" 2602 and the plate inserted into a measuring instrument, in this instance a MALDI-ToF mass spectrometer 2606. The mass spectrometer 2606 acquires a mass spectrum 2608 from each of the three aliquots of the sample. The mass spectra are represented in digital form and supplied to a programmed general purpose compute 2610. The computer 2610 includes a central processing unit 2612 executing programmed instructions. The memory 2614 stores the data representing the mass spectra 2608.

The memory 2614 also stores a master or final CMC/D classifier 2620, which includes a) a training set 2622 in the form of a feature table of N class-labeled spectra, where N is some integer number, in this example class-labeled spectra from patients enrolled in a clinical trial as described earlier, and each sample assigned a class label such as "early", "late", "+", "−", "good", "poor", etc., b) code representing a KNN classification algorithm, c) program code for executing the final classifier generated in accordance with FIG. 1 on the mass spectra of patients, and d) a data structure 2628 for storing classification results, and a final class label for the test sample. The memory 2614 also stores program code 2630 for implementing the processing shown at 2650, including code (not shown) for acquiring the mass spectral data from the mass spectrometer in step 2652; a pre-processing routine 2632 for implementing the background subtraction, normalization and alignment step 2654, a module (not shown) for obtaining integrated intensity values at predefined m/Z positions in the background subtracted, normalized and aligned spectrum (step 2656), and a code routine 2638 for implementing the classifier 2620 using the training set 2622 on the values obtained at step 2656. The process 2658 produces a class label at step 2660. Program code 2642 includes code that makes a check (step 2662) to determine if all three aliquots of the sample produced the same class label. If no, the class label "undefined" or the equivalent is reported. If all three aliquots to the patient sample 2600 produce the same class label, the module 2640 reports the class label as indicated at 2666 (i.e., "early", "late", "+", "−", "good", "poor" or the equivalent).

The program code 2630 can include additional and optional modules, for example a feature correction function code 2632 (described in FIG. 2), a set of routines for processing the spectrum from a reference sample 2604 to define a feature correction function, a module storing feature dependent noise characteristics and generated noisy feature value realizations (see FIG. 2) and classifying such noisy feature value realizations, and modules storing statistical algorithms for obtaining statistical data on the performance of the classifier on the noisy feature value realizations. Still other optional software modules could be included as will be apparent to persons skilled in the art.

The system of FIG. 16 can be implemented as laboratory test processing center obtaining a multitude of patient samples from oncologists, patients, clinics, etc., and generating a class label for the patient samples as a fee-for-service. The mass spectrometer 2606 need not be physically located at the laboratory test center but rather the computer 2610 could obtain the data representing the mass spectra of the test sample over a computer network.

Method of Treatment of NSCLC Patient

It will be further understood that we have described a method of treating a NSCLC patient. The treatment takes the form of administering an EGFR-I to the NSCLC patient, wherein the patient is predicted to benefit more from the EGFR-I as compared to chemotherapy by executing in a programmed computer a classifier comparing mass spectral data produced by a mass spectrometer from a blood-based sample of the NSCLC patient to a training set comprising class-labeled mass spectral data obtained from a multitude of cancer patients who are determined by mass spectrometry of a blood-based sample to be members of a class of patients that are predicted to obtain overall survival benefit from an EGFR-I in treatment of the cancer. Such class of patients further divided into two sub-classes:

1. those patients which exhibited early progression of disease after administration of the EGFR-I in treatment of cancer, mass spectral data of such patients having a class label of "early" or the equivalent; and 2. those patients which exhibited late progression of disease after administration of an EGFR-I in treatment of cancer, mass spectral data of such patients having a class label of "late" or the equivalent. Furthermore, the programmed computer can take the form of a classifier implementing a classification algorithm as described in detail in previous sections of this document. For example, the programmed computer implements a classifier in the form of a combination of filtered mini-classifiers after dropout regularization and logistical training (CMC/D classifier). The EGFR-I could take the form of gefitinib, erlotinib, a second generation EGFR-I such as dacominitib, affatinib, or the equivalent, with dosing according to established protocols.

The appended claims are offered as further descriptions of the disclosed inventions.

Appendices

APPENDIX A

| Samples Used in Classifier Development |
|---|
| Sample ID |
| ICA_1 |
| ICA_10 |
| ICA_11 |
| ICA_12 |
| ICA_13 |
| ICA_14 |
| ICA_15 |
| ICA_17 |
| ICA_18 |
| ICA_19 |
| ICA_2 |
| ICA_20 |
| ICA_21 |
| ICA_22 |
| ICA_23 |
| ICA_24 |
| ICA_25 |
| ICA_26 |
| ICA_27 |
| ICA_28 |
| ICA_29 |

APPENDIX A-continued

Samples Used in Classifier Development

Sample ID

ICA_3
ICA_30
ICA_31
ICA_32
ICA_34
ICA_35
ICA_36
ICA_38
ICA_39
ICA_4
ICA_40
ICA_41
ICA_42
ICA_43
ICA_44
ICA_45
ICA_46
ICA_47
ICA_48
ICA_49
ICA_5
ICA_50
ICA_51
ICA_52
ICA_54
ICA_55
ICA_56
ICA_57
ICA_58
ICA_59
ICA_6
ICA_60
ICA_61
ICA_63
ICA_64
ICA_65
ICA_67
ICA_68
ICA_69
ICA_7
ICA_70
ICA_8
ICB_1
ICB_10
ICB_11
ICB_12
ICB_13
ICB_14
ICB_15
ICB_16
ICB_17
ICB_18
ICB_19
ICB_2
ICB_20
ICB_21
ICB_22
ICB_23
ICB_24
ICB_25
ICB_26
ICB_27
ICB_28
ICB_29
ICB_3
ICB_30
ICB_31
ICB_32
ICB_33
ICB_34
ICB_35
ICB_36
ICB_37
ICB_38

APPENDIX A-continued

Samples Used in Classifier Development

Sample ID

ICB_39
ICB_4
ICB_40
ICB_41
ICB_42
ICB_43
ICB_44
ICB_45
ICB_46
ICB_47
ICB_48
ICB_49
ICB_5
ICB_50
ICB_51
ICB_52
ICB_53
ICB_54
ICB_55
ICB_56
ICB_57
ICB_58
ICB_59
ICB_6
ICB_60
ICB_61
ICB_62
ICB_63
ICB_64
ICB_65
ICB_66
ICB_67
ICB_8
ICB_9
ICC_1
ICC_10
ICC_11
ICC_12
ICC_13
ICC_14
ICC_15
ICC_16
ICC_17
ICC_18
ICC_19
ICC_2
ICC_20
ICC_21
ICC_22
ICC_23
ICC_24
ICC_25
ICC_26
ICC_27
ICC_28
ICC_29
ICC_3
ICC_30
ICC_31
ICC_32
ICC_4
ICC_5
ICC_6
ICC_7
ICC_8
ICC_9

APPENDIX B

Features Used in CMC/D Classifiers

| Center | Left | Right |
|---|---|---|
| 3218.7386 | 3206.9871 | 3230.49 |
| 3315.4528 | 3302.6206 | 3328.285 |
| 4409.1599 | 4400.38 | 4417.94 |
| 4466.5671 | 4453.3297 | 4479.805 |
| 4715.9166 | 4700.9233 | 4730.91 |
| 4790.6135 | 4764.6789 | 4816.548 |
| 4862.7438 | 4846.8049 | 4878.683 |
| 5740.33 | 5689.9468 | 5790.713 |
| 5851.6323 | 5796.3864 | 5906.878 |
| 5945.9151 | 5914.4425 | 5977.388 |
| 6291.0333 | 6276.175 | 6305.892 |
| 6436.5097 | 6410.7103 | 6462.309 |
| 6531.4679 | 6517.0148 | 6545.921 |
| 6647.2276 | 6606.9751 | 6687.48 |
| 6835.523 | 6823.2312 | 6847.815 |
| 6859.0262 | 6849.9761 | 6868.076 |
| 6887.3988 | 6871.2103 | 6903.587 |
| 6942.638 | 6907.3833 | 6977.893 |
| 7044.8902 | 7019.7662 | 7070.014 |
| 7195.2294 | 7176.9942 | 7213.465 |
| 7388.9278 | 7374.8799 | 7402.976 |
| 7567.903 | 7548.4521 | 7587.354 |
| 7663.6716 | 7641.9244 | 7685.419 |
| 7765.1134 | 7750.9304 | 7779.296 |
| 7940.7116 | 7914.2368 | 7967.187 |
| 8019.8659 | 7975.8313 | 8063.901 |
| 8222.2092 | 8194.6538 | 8249.765 |
| 8582.8611 | 8556.6564 | 8609.066 |
| 8633.3793 | 8615.0091 | 8651.75 |
| 8696.8649 | 8673.0916 | 8720.638 |
| 8771.1565 | 8751.5705 | 8790.742 |
| 8819.6486 | 8800.1977 | 8839.1 |
| 8874.8945 | 8858.5504 | 8891.239 |
| 8934.0576 | 8900.4238 | 8967.692 |
| 9023.3426 | 9004.2969 | 9042.388 |
| 9147.2069 | 9108.5753 | 9185.839 |
| 9296.8707 | 9269.4504 | 9324.291 |
| 9359.8159 | 9331.8553 | 9387.777 |
| 9440.8613 | 9401.8245 | 9479.898 |
| 9584.3116 | 9553.2442 | 9615.379 |
| 9654.0106 | 9619.7014 | 9688.32 |
| 9731.9492 | 9696.4243 | 9767.474 |
| 9939.5604 | 9899.9833 | 9979.138 |
| 10641.5484 | 10617.64 | 10665.46 |
| 10828.7631 | 10808.2317 | 10849.29 |
| 11395.5404 | 11375.4141 | 11415.67 |
| 11440.1153 | 11427.013 | 11453.22 |
| 11512.9211 | 11464.564 | 11561.28 |
| 11699.0553 | 11597.2083 | 11800.9 |
| 11884.9193 | 11831.2943 | 11938.54 |
| 12112.5217 | 12062.4086 | 12162.63 |
| 12449.5353 | 12424.2762 | 12474.79 |
| 12577.8361 | 12557.5686 | 12598.1 |
| 12615.0568 | 12600.6529 | 12629.46 |
| 12727.1157 | 12712.9328 | 12741.3 |
| 12864.8928 | 12838.1478 | 12891.64 |
| 13125.0484 | 13107.6237 | 13142.47 |
| 13312.3983 | 13293.3526 | 13331.44 |
| 13577.2816 | 13556.615 | 13597.95 |
| 13749.638 | 13693.4466 | 13805.83 |
| 13883.9032 | 13816.0952 | 13951.71 |
| 13982.3733 | 13959.5455 | 14005.2 |
| 14048.2902 | 14021.0049 | 14075.58 |
| 14096.9174 | 14079.0874 | 14114.75 |
| 14156.3507 | 14130.146 | 14182.56 |
| 14484.7195 | 14462.432 | 14507.01 |
| 14777.5634 | 14759.4632 | 14795.66 |
| 17268.0853 | 17235.6355 | 17300.54 |
| 17401.8418 | 17364.907 | 17438.78 |
| 17607.8848 | 17577.5456 | 17638.22 |
| 18634.4067 | 18591.1403 | 18677.67 |
| 21071.3078 | 21030.6796 | 21111.94 |
| 22316.6349 | 22129.9002 | 22503.37 |
| 23220.6291 | 22951.4507 | 23489.81 |

APPENDIX C

Initial Class Labels for First Stage of Classifier Development

| Sample ID | Class Label |
|---|---|
| 36HSR | Early |
| 38HSR | Early |
| 39HSR | Early |
| 40HSR | Early |
| 45HSR | Early |
| 51HSR | Early |
| 56HSR | Early |
| 63HSR | Early |
| 68HSR | Early |
| ICB_03 | Early |
| ICB_06 | Early |
| ICB_10 | Early |
| ICB_12 | Early |
| ICB_13 | Early |
| ICB_22 | Early |
| ICB_26 | Early |
| ICB_34 | Early |
| ICB_38 | Early |
| ICB_40 | Early |
| ICB_43 | Early |
| ICB_45 | Early |
| ICB_60 | Early |
| ICB_63 | Early |
| 10HSR | Late |
| 11HSR | Late |
| 12HSR | Late |
| 13HSR | Late |
| 14HSR | Late |
| 17HSR | Late |
| 18HSR | Late |
| 19HSR | Late |
| 1HSR | Late |
| 20HSR | Late |
| 21HSR | Late |
| 22HSR | Late |
| 2HSR | Late |
| 4HSR | Late |
| 7HSR | Late |
| 8HSR | Late |
| ICB_05 | Late |
| ICB_28 | Late |
| ICB_31 | Late |
| ICB_41 | Late |
| ICB_57 | Late |
| ICB_61 | Late |
| ICB_64 | Late |

APPENDIX D

Noise type and noise strength for VS2.0 features

| m/Z Center of Feature | Noise Type | Noise Strength |
|---|---|---|
| 3218.7386 | additive | 0.449589 |
| 3315.4528 | additive | 0.705299 |
| 4409.1599 | additive | 0.372679 |
| 4466.5671 | additive | 0.558918 |
| 4715.9166 | multiplicative | 0.215793 |
| 4790.6135 | additive | 0.871467 |
| 4862.7438 | multiplicative | 0.224417 |
| 5740.33 | multiplicative | 0.219152 |
| 5851.6323 | multiplicative | 0.250464 |
| 5945.9151 | multiplicative | 0.671156 |
| 6291.0333 | additive | 0.204162 |
| 6436.5097 | additive | 1.674129 |
| 6531.4679 | additive | 0.19534 |
| 6647.2276 | additive | 3.511696 |
| 6835.523 | additive | 0.369546 |
| 6859.0262 | additive | 0.216011 |
| 6887.3988 | additive | 0.449448 |
| 6942.638 | additive | 1.17939 |
| 7044.8902 | additive | 0.435487 |
| 7195.2294 | additive | 0.222608 |

APPENDIX D-continued

Noise type and noise strength for VS2.0 features

| m/Z Center of Feature | Noise Type | Noise Strength |
|---|---|---|
| 7388.9278 | additive | 0.163982 |
| 7567.903 | multiplicative | 0.156163 |
| 7663.6716 | multiplicative | 0.195681 |
| 7765.1134 | additive | 0.319943 |
| 7940.7116 | additive | 0.419978 |
| 8019.8659 | additive | 0.356489 |
| 8222.2092 | additive | 0.431253 |
| 8582.8611 | additive | 0.347085 |
| 8633.3793 | additive | 0.268113 |
| 8696.8649 | multiplicative | 0.274013 |
| 8771.1565 | additive | 0.692564 |
| 8819.6486 | multiplicative | 0.38203 |
| 8874.8945 | additive | 0.514021 |
| 8934.0576 | multiplicative | 0.29018 |
| 9023.3426 | additive | 0.416469 |
| 9147.2069 | multiplicative | 0.233822 |
| 9296.8707 | multiplicative | 2.007367 |
| 9359.8159 | multiplicative | 0.15884 |
| 9440.8613 | multiplicative | 0.155807 |
| 9584.3116 | multiplicative | 0.280165 |
| 9654.0106 | multiplicative | 0.200748 |
| 9731.9492 | multiplicative | 0.200652 |
| 9939.5604 | multiplicative | 0.240092 |
| 10641.5484 | additive | 0.246795 |
| 10828.7631 | additive | 0.374312 |
| 11395.5404 | additive | 0.511211 |
| 11440.1153 | multiplicative | 0.240577 |
| 11512.9211 | multiplicative | 0.316491 |
| 11699.0553 | multiplicative | 0.402835 |
| 11884.9193 | multiplicative | 0.190473 |
| 12112.5217 | multiplicative | 1.367853 |
| 12449.5353 | multiplicative | 2.019671 |
| 12577.8361 | multiplicative | 0.163202 |
| 12615.0568 | multiplicative | 0.50929 |
| 12727.1157 | multiplicative | 0.212812 |
| 12864.8928 | multiplicative | 0.116047 |
| 13125.0484 | additive | 0.143445 |
| 13312.3983 | additive | 0.144914 |
| 13577.2816 | additive | 0.136992 |
| 13749.638 | additive | 1.208693 |
| 13883.9032 | additive | 2.503822 |
| 13982.3733 | additive | 0.517253 |
| 14048.2902 | additive | 1.393395 |
| 14096.9174 | additive | 0.595363 |
| 14156.3507 | additive | 0.837603 |
| 14484.7195 | additive | 0.22863 |
| 14777.5634 | additive | 0.091024 |
| 17268.0853 | additive | 0.353217 |
| 17401.8418 | additive | 0.574893 |
| 17607.8848 | additive | 0.142937 |
| 18634.4067 | additive | 0.133441 |
| 21071.3078 | additive | 0.133543 |
| 22316.6349 | additive | 1.392056 |
| 23220.6291 | additive | 0.776561 |

APPENDIX E

VS2.0 Classifications of Development Set Samples

| Sample ID | Overall Classification | VS1.0 Classification |
|---|---|---|
| ICA_1 | Late | Good |
| ICA_10 | Late | Good |
| ICA_11 | Early | Good |
| ICA_12 | Early | Good |
| ICA_13 | Late | Good |
| ICA_14 | Late | Good |
| ICA_15 | Late | Good |
| ICA_17 | Late | Good |
| ICA_18 | Early | Good |
| ICA_19 | Late | Good |
| ICA_2 | Late | Good |
| ICA_20 | Late | Good |
| ICA_21 | Late | Good |
| ICA_22 | Early | Good |
| ICA_23 | Early | Good |
| ICA_24 | Early | Poor |
| ICA_25 | Early | Good |
| ICA_26 | Early | Good |
| ICA_27 | Late | Good |
| ICA_28 | Early | Good |
| ICA_29 | Early | Good |
| ICA_3 | Early | Poor |
| ICA_30 | Early | Poor |
| ICA_31 | Early | Good |
| ICA_32 | Early | Good |
| ICA_34 | Late | Good |
| ICA_35 | Early | Good |
| ICA_36 | Late | Good |
| ICA_38 | Early | Good |
| ICA_39 | Early | Good |
| ICA_4 | Late | Good |
| ICA_40 | Early | Good |
| ICA_41 | Late | Good |
| ICA_42 | Early | Good |
| ICA_43 | Early | Poor |
| ICA_44 | Late | Good |
| ICA_45 | Early | Good |
| ICA_46 | Early | Good |
| ICA_47 | Early | Poor |
| ICA_48 | Late | Good |
| ICA_49 | Early | Poor |
| ICA_5 | Late | Good |
| ICA_50 | Late | Good |
| ICA_51 | Late | Good |
| ICA_52 | Early | Poor |
| ICA_54 | Early | Poor |
| ICA_55 | Late | Good |
| ICA_56 | Early | Good |
| ICA_57 | Early | Poor |
| ICA_58 | Early | Poor |
| ICA_59 | Early | Poor |
| ICA_6 | Early | Poor |
| ICA_60 | Early | Poor |
| ICA_61 | Early | Poor |
| ICA_63 | Early | Good |
| ICA_64 | Early | Poor |
| ICA_65 | Early | Poor |
| ICA_67 | Early | Good |
| ICA_68 | Late | Good |
| ICA_69 | Early | Poor |
| ICA_7 | Late | Good |
| ICA_70 | Early | Good |
| ICA_8 | Late | Good |
| ICB_1 | Early | Poor |
| ICB_10 | Early | Good |
| ICB_11 | Early | Poor |
| ICB_12 | Late | Good |
| ICB_13 | Early | Good |
| ICB_14 | Early | Good |
| ICB_15 | Early | Good |
| ICB_16 | Late | Good |
| ICB_17 | Late | Good |
| ICB_18 | Early | Poor |
| ICB_19 | Early | Poor |
| ICB_2 | Late | Good |
| ICB_20 | Early | Poor |
| ICB_21 | Early | Good |
| ICB_22 | Late | Good |
| ICB_23 | Early | Poor |
| ICB_24 | Early | Poor |
| ICB_25 | Early | Poor |
| ICB_26 | Early | Good |
| ICB_27 | Early | Poor |
| ICB_28 | Late | Good |
| ICB_29 | Early | Poor |
| ICB_3 | Late | Good |
| ICB_30 | Early | Poor |
| ICB_31 | Late | Good |

APPENDIX E-continued

VS2.0 Classifications of Development Set Samples

| Sample ID | Overall Classification | VS1.0 Classification |
|---|---|---|
| ICB_32 | Early | Poor |
| ICB_33 | Early | Poor |
| ICB_34 | Early | Good |
| ICB_35 | Early | Poor |
| ICB_36 | Late | Good |
| ICB_37 | Early | Poor |
| ICB_38 | Late | Good |
| ICB_39 | Early | Good |
| ICB_4 | Early | Poor |
| ICB_40 | Late | Good |
| ICB_41 | Late | Good |
| ICB_42 | Early | Poor |
| ICB_43 | Early | Good |
| ICB_44 | Early | Poor |
| ICB_45 | Early | Good |
| ICB_46 | Early | Poor |
| ICB_47 | Late | Good |
| ICB_48 | Early | Good |
| ICB_49 | Late | Good |
| ICB_5 | Late | Good |
| ICB_50 | Late | Good |
| ICB_51 | Early | Poor |
| ICB_52 | Late | Good |
| ICB_53 | Early | Poor |
| ICB_54 | Early | Good |
| ICB_55 | Early | Poor |
| ICB_56 | Early | Poor |
| ICB_57 | Late | Good |
| ICB_58 | Early | Poor |
| ICB_59 | Early | Poor |
| ICB_6 | Early | Good |
| ICB_60 | Early | Good |
| ICB_61 | Early | Good |
| ICB_62 | Early | Good |
| ICB_63 | Early | Good |
| ICB_64 | Late | Good |
| ICB_65 | Early | Good |
| ICB_66 | Early | Poor |
| ICB_67 | Late | Good |
| ICB_8 | Early | Poor |
| ICB_9 | Late | Good |
| ICC_1 | Early | Poor |
| ICC_10 | Early | Good |
| ICC_11 | Late | Good |
| ICC_12 | Early | Poor |
| ICC_13 | Early | Poor |
| ICC_14 | Early | Good |
| ICC_15 | Early | Poor |
| ICC_16 | Early | Poor |
| ICC_17 | Late | Good |
| ICC_18 | Early | Poor |
| ICC_19 | Early | Good |
| ICC_2 | Early | Poor |
| ICC_20 | Early | Poor |
| ICC_21 | Late | Good |
| ICC_22 | Early | Good |
| ICC_23 | Late | Good |
| ICC_24 | Late | Good |
| ICC_25 | Early | Good |
| ICC_26 | Early | Good |
| ICC_27 | Late | Good |
| ICC_28 | Late | Good |
| ICC_29 | Late | Good |
| ICC_3 | Early | Poor |
| ICC_30 | Early | Good |
| ICC_31 | Early | Good |
| ICC_32 | Early | Poor |
| ICC_4 | Early | Good |
| ICC_5 | Early | Good |
| ICC_6 | Early | Poor |
| ICC_7 | Early | Good |
| ICC_8 | Early | Poor |
| ICC_9 | Early | Good |

APPENDIX F

VS2.0 Classifications of Development Set Samples Across Three Runs

| Sample ID | Development Run Classification | Development Run Noise Effect Estimator | Feb_3 Classification | Feb_3 Noise Effect Estimator | Feb_25 Classification | Feb_25 Noise quantifier |
|---|---|---|---|---|---|---|
| ICA_1 | Late | 0.2508903 | Late | 0.466734822 | Unknown | 1.25354 |
| ICA_10 | Late | 0.3138037 | Unknown | 1.964538835 | Unknown | 3.23176 |
| ICA_11 | Early | 0.080601 | Early | 0.31109509 | Early | 0.18127 |
| ICA_12 | Early | 0.0355124 | Early | 0.00909397 | Early | 0.1501 |
| ICA_13 | Late | 0.0047174 | Late | 0.030926878 | Late | 0.08849 |
| ICA_14 | Unknown | 2.7555361 | Unknown | 6.009376135 | Unknown | 0.57061 |
| ICA_15 | Late | 0.0149085 | Late | 0.187318654 | Late | 0.08098 |
| ICA_17 | Late | 0.0451973 | Late | 0.130183945 | Late | 0.10486 |
| ICA_18 | Early | 0.3983651 | Early | 0.134071541 | Early | 0.2023 |
| ICA_19 | Late | 0.0826776 | Late | 0.027922277 | Late | 0.03699 |
| ICA_2 | Late | 0.0115269 | Late | 0.014803894 | Late | 0.01478 |
| ICA_20 | Late | 0.2883118 | Late | 0.468349356 | Unknown | 1.55056 |
| ICA_21 | Late | 0.3249368 | Late | 0.197541409 | Late | 0.42881 |
| ICA_22 | Early | 0.4547106 | Unknown | 408.6471898 | Unknown | 10.2749 |
| ICA_23 | Early | 0.0748141 | Unknown | 1.064878786 | | |
| ICA_24 | Unknown | 0.5213397 | Early | 0.273862348 | | |
| ICA_25 | Unknown | 0.5367448 | Unknown | 0.576202188 | Unknown | 2.14736 |
| ICA_26 | Unknown | 1.4825573 | Unknown | 1.176456598 | Unknown | 1.14433 |
| ICA_27 | Late | 0.4851147 | Unknown | 0.823851604 | Unknown | 0.54047 |
| ICA_28 | Early | 0.024537 | Early | 0.041470212 | Early | 0.04415 |
| ICA_29 | Early | 0.0684268 | Early | 0.199645029 | Early | 0.23878 |
| ICA_3 | Early | 0.0449748 | Early | 0 | | |
| ICA_30 | Early | 0.1134967 | Early | 0 | | |
| ICA_31 | Unknown | 1.1973862 | Unknown | 2.017268589 | Unknown | 7.40837 |
| ICA_32 | Unknown | 0.9744799 | Unknown | 3.705512439 | Unknown | 1.88644 |
| ICA_34 | Late | 0.0513075 | Late | 0.075731492 | Late | 0.15651 |
| ICA_35 | Early | 0.2933299 | Early | 0.191894212 | Early | 0.0942 |

APPENDIX F-continued

VS2.0 Classifications of Development Set Samples Across Three Runs

| Sample ID | Development Run Classification | Development Run Noise Effect Estimator | Feb_3 Classification | Feb_3 Noise Effect Estimator | Feb_25 Classification | Feb_25 Noise quantifier |
|---|---|---|---|---|---|---|
| ICA_36 | Late | 0.0405301 | Late | 0.207008265 | | |
| ICA_38 | Unknown | 0.6299707 | Early | 0.286152473 | Unknown | 1.39855 |
| ICA_39 | Unknown | 0.6493858 | Unknown | 2.07717748 | Unknown | 1.02573 |
| ICA_4 | Late | 0 | Late | 0.038223058 | Late | 0.06442 |
| ICA_40 | Early | 0.1460363 | Unknown | 2.460497465 | Early | 0.11424 |
| ICA_41 | Late | 0.359934 | Late | 0.401264716 | Unknown | 0.757 |
| ICA_42 | Unknown | 2.2944611 | Early | 0.123948659 | Early | 0.27961 |
| ICA_43 | Early | 0.0967663 | Early | 0.000632487 | | |
| ICA_44 | Unknown | 1.6734598 | Early | 0.169833656 | Early | 0.40807 |
| ICA_45 | Unknown | 1.0538265 | Unknown | 0.584840142 | Early | 0.21289 |
| ICA_46 | Early | 0.4287061 | Unknown | 2.926113519 | Unknown | 0.6906 |
| ICA_47 | Early | 0.0535227 | Early | 0 | | |
| ICA_48 | Late | 0.4357615 | Unknown | 2.0349327 | Unknown | 2.07714 |
| ICA_49 | Early | 0 | Early | 0 | | |
| ICA_5 | Unknown | 0.9192309 | Unknown | 0.653490123 | Late | 0.21708 |
| ICA_50 | Unknown | 2.6894001 | Early | 0.158682214 | Unknown | 0.51338 |
| ICA_51 | Late | 0.1653643 | Late | 0.31185332 | Unknown | 0.9165 |
| ICA_52 | Early | 0.0045497 | Early | 0 | | |
| ICA_54 | Early | 0.0918534 | Early | 0 | | |
| ICA_55 | Late | 0.009786 | Unknown | 0.556007152 | Unknown | 1.96082 |
| ICA_56 | Early | 0.0022435 | Early | 0.050034194 | Early | 0.0091 |
| ICA_57 | Early | 0.0050177 | Early | 0.000632487 | | |
| ICA_58 | Early | 0 | Early | 0 | | |
| ICA_59 | Early | 0.0020317 | Early | 0.001887201 | | |
| ICA_6 | Early | 0.0010887 | Early | 0 | | |
| ICA_60 | Early | 0 | Early | 0 | | |
| ICA_61 | Early | 0 | Early | 0 | | |
| ICA_63 | Early | 0.0304895 | Early | 0.046816893 | Early | 0.14536 |
| ICA_64 | Early | 0 | Early | 0 | | |
| ICA_65 | Early | 0 | Early | 0 | | |
| ICA_67 | Unknown | 0.7938756 | Unknown | 0.826523764 | Unknown | 0.60441 |
| ICA_68 | Late | 0.2370179 | Unknown | 2.282512088 | Unknown | 2.00963 |
| ICA_69 | Early | 0.0061302 | Early | 0.014126042 | | |
| ICA_7 | Late | 0.2874263 | Late | 0.092535875 | Late | 0.17229 |
| ICA_70 | Unknown | 0.8459228 | Unknown | 0.592744714 | Early | 0.19042 |
| ICA_8 | Late | 0.3185725 | Unknown | 0.524389074 | Unknown | 1.06012 |
| ICB_1 | Early | 0.001642 | Early | 0 | | |
| ICB_10 | Early | 0.1244703 | Early | 0.071776831 | Early | 0.04976 |
| ICB_11 | Early | 0 | Early | 0 | | |
| ICB_12 | Late | 0.4010251 | Unknown | 3.819985778 | Unknown | 2.46467 |
| ICB_13 | Early | 0.0335419 | Early | 0.239284331 | Early | 0.20115 |
| ICB_14 | Unknown | 0.7794731 | Unknown | 1.064463653 | Early | 0.20933 |
| ICB_15 | Unknown | 1.402295 | Early | 0.005996916 | Early | 0.05784 |
| ICB_16 | Late | 0.49193 | Unknown | 3.18288305 | | |
| ICB_17 | Unknown | 15.495518 | Unknown | 2.770598757 | Unknown | 0.75083 |
| ICB_18 | Early | 0.0104891 | Early | 0 | | |
| ICB_19 | Early | 0.0044287 | Early | 0 | | |
| ICB_2 | Unknown | 1.8319861 | Unknown | 0.574145865 | Unknown | 1.11314 |
| ICB_20 | Early | 0.1010281 | Early | 0.001265038 | | |
| ICB_21 | Early | 0.3837118 | Early | 0.047678494 | Early | 0.42108 |
| ICB_22 | Late | 0.24719 | Unknown | 1.296687602 | Unknown | 2.0375 |
| ICB_23 | Early | 0.0080037 | Early | 0 | | |
| ICB_24 | Early | 0 | Early | 0 | | |
| ICB_25 | Early | 0.4691525 | Early | 0.374906318 | | |
| ICB_26 | Early | 0.2842823 | Unknown | 18.84274386 | Unknown | 1.65263 |
| ICB_27 | Early | 0.1090687 | Early | 0.026120232 | | |
| ICB_28 | Late | 0.0106621 | Late | 0.174473568 | Late | 0.11698 |
| ICB_29 | Early | 0.0235619 | Early | 0.009862237 | | |
| ICB_3_rerun | Late | 0.0304724 | Late | 0.067773006 | | |
| ICB_30 | Early | 0.0210381 | Early | 0.007672574 | | |
| ICB_31 | Late | 0.1671391 | Unknown | 1.269484668 | Unknown | 2.60353 |
| ICB_32 | Early | 0.0504194 | Early | 0.006513994 | | |
| ICB_33 | Early | 0.0022743 | Early | 0 | | |
| ICB_34 | Unknown | 0.7717411 | Early | 0.235015835 | Early | 0.23868 |
| ICB_35 | Early | 0.1187116 | Unknown | 0.684071314 | | |
| ICB_36 | Unknown | 0.6113689 | Early | 0.495122448 | | |
| ICB_37 | Early | 0 | Early | 0.000632487 | | |
| ICB_38 | Unknown | 0.7252647 | Late | 0.327507909 | Unknown | 7.41886 |
| ICB_39 | Early | 0.0873692 | Unknown | 0.538723703 | Unknown | 0.69525 |
| ICB_4 | Early | 0.0583902 | Early | 0 | | |
| ICB_40 | Unknown | 1.5221366 | Unknown | 1.376172237 | Unknown | 4.11934 |
| ICB_41 | Late | 0.2281209 | Unknown | 2.942393151 | | |
| ICB_42 | Early | 0.016582 | Early | 0.001265038 | | |

APPENDIX F-continued

VS2.0 Classifications of Development Set Samples Across Three Runs

| Sample ID | Development Run Classification | Development Run Noise Effect Estimator | Feb_3 Classification | Feb_3 Noise Effect Estimator | Feb_25 Classification | Feb_25 Noise quantifier |
|---|---|---|---|---|---|---|
| ICB_43 | Early | 0.008667 | Early | 0.014663441 | Early | 0.00617 |
| ICB_44 | Early | 0.026458 | Early | 0.001253172 | | |
| ICB_45 | Early | 0.3637465 | Early | 0.19639466 | Early | 0.17223 |
| ICB_46 | Early | 0 | Early | 0 | | |
| ICB_47 | Late | 0.3112708 | Late | 0.37180672 | Unknown | 0.53511 |
| ICB_48 | Unknown | 0.6104345 | Unknown | 0.695956133 | Unknown | 1.19754 |
| ICB_49 | Unknown | 0.8091827 | Unknown | 1.921287211 | | |
| ICB_5 | Unknown | 0.5610236 | Unknown | 1.791500069 | Unknown | 19.3159 |
| ICB_50 | Unknown | 1.5210721 | Early | 0.322646083 | | |
| ICB_51 | Early | 0.2798399 | Early | 0.411311501 | | |
| ICB_52 | Late | 0.0913128 | Unknown | 0.995984435 | Late | 0.0946 |
| ICB_53 | Early | 0.0177726 | Early | 0 | | |
| ICB_54 | Unknown | 3.9796933 | Unknown | 0.729611954 | | |
| ICB_55 | Early | 0.2673627 | Early | 0.016808751 | | |
| ICB_56 | Early | 0.016083 | Early | 0.001660149 | | |
| ICB_57 | Late | 0.0495004 | Late | 0.454621578 | Unknown | 5.38489 |
| ICB_58 | Early | 0 | Early | 0 | | |
| ICB_59 | Early | 0.099419 | Early | 0 | | |
| ICB_6 | Early | 0.0926929 | Early | 0.010137147 | Early | 0.01514 |
| ICB_60 | Early | 0.024118 | Early | 0.045176626 | Early | 0.22779 |
| ICB_61 | Early | 0.0207761 | Early | 0.098978496 | Early | 0.05717 |
| ICB_62 | Early | 0.1123475 | Early | 0.038795663 | | |
| ICB_63 | Early | 0.3143604 | Unknown | 0.5577347 | Early | 0.17666 |
| ICB_64 | Late | 0.2135021 | Unknown | 0.981560369 | | |
| ICB_65 | Early | 0.4912493 | Unknown | 0.975042177 | Early | 0.48021 |
| ICB_66 | Early | 0.0471047 | Early | 0.046567508 | | |
| ICB_67 | Unknown | 0.5234719 | Early | 0.322026183 | | |
| ICB_8 | Early | 0.0052102 | Early | 0 | | |
| ICB_9 | Late | 0.1080207 | Late | 0.042361028 | Late | 0.04029 |
| ICC_1 | Early | 0.2070783 | Early | 0.085396794 | | |
| ICC_10 | Early | 0.1236901 | Early | 0.004740175 | Early | 0.01399 |
| ICC_11 | Unknown | 1.1814412 | Unknown | 2.209011682 | Unknown | 1.34544 |
| ICC_12 | Early | 0.0054516 | Early | 0 | | |
| ICC_13 | Early | 0 | Early | 0 | | |
| ICC_14 | Unknown | 0.9532531 | Early | 0.208090801 | Early | 0.40234 |
| ICC_15 | Early | 0.0046228 | Early | 0.000632487 | | |
| ICC_16 | Early | 0.0006325 | Early | 0 | | |
| ICC_17 | Unknown | 1.060111 | Unknown | 0.503778812 | Late | 0.33919 |
| ICC_18 | Early | 0.001265 | Early | 0.010079649 | | |
| ICC_19 | Early | 0.0946116 | Early | 0.034253636 | Early | 0.21303 |
| ICC_2 | Early | 0 | Early | 0 | | |
| ICC_20 | Early | 0.0392832 | Early | 0.101833857 | | |
| ICC_21 | Late | 0.1985239 | Late | 0.269895491 | Unknown | 1.26594 |
| ICC_22 | Early | 0.1766128 | Unknown | 1.01724785 | Unknown | 2.29042 |
| ICC_23 | Unknown | 2.3518283 | Unknown | 4.747822355 | Unknown | 36.0979 |
| ICC_24 | Late | 0.4498147 | Unknown | 1.641647487 | Late | 0.23851 |
| ICC_25 | Early | 0.2547183 | Early | 0.026712614 | Early | 0.20825 |
| ICC_26 | Early | 0.0183961 | Early | 0.177587583 | Early | 0.06516 |
| ICC_27 | Unknown | 2.6560691 | Unknown | 0.894522603 | Unknown | 4.03214 |
| ICC_28 | Unknown | 5.162227 | Unknown | 1.585391499 | Unknown | 1.17993 |
| ICC_29 | Late | 0.0907799 | Late | 0.134559673 | Late | 0.30603 |
| ICC_3 | Early | 0.0006325 | Early | 0 | | |
| ICC_30 | Early | 0.0374486 | Early | 0.025356686 | Early | 0.03447 |
| ICC_31 | Early | 0.2820449 | Early | 0.145453279 | Early | 0.23148 |
| ICC_32 | Early | 0.0045497 | Early | 0 | | |
| ICC_4 | Unknown | 2.6580968 | Unknown | 0.635164246 | Unknown | 5.92408 |
| ICC_5 | Early | 0.1713111 | Unknown | 0.519211365 | Unknown | 0.51357 |
| ICC_6 | Early | 0.0193609 | Early | 0 | | |
| ICC_7 | Early | 0.0008917 | Early | 0 | Early | 0.0272 |
| ICC_8 | Early | 0.0873546 | Early | 0 | | |
| ICC_9 | Early | 0.0085559 | Early | 0.002577784 | Early | 0.00956 |

APPENDIX G

VS2.0 Classifications returned for PROSE samples

| Blinded ID | VS2.0 CLASSIFICATION | PROSE Sample # |
|---|---|---|
| 3001 | Unknown | 01_024_1 |
| 3009 | Early | 11_046_1 |
| 3023 | Unknown | 01_055_1 |
| 3038 | Unknown | 16_005_1 |
| 3053 | Early | 04_001_1 |
| 3058 | Unknown | 10_002_1 |
| 3065 | Early | 16_013_1 |
| 3098 | Early | 11_055_1 possible repeat |
| 3099 | Unknown | 06_014_1 |
| 3116 | Early | 01_059_1 |
| 3170 | Unknown | 01_013_1 |
| 3194 | Late | 10_005_1 |
| 3200 | Late | 01_074_1 |
| 3204 | Early | 01_010_1 |
| 3214 | Sample not available for MS generation | 11_043_1 |
| 3246 | Early | 16_012_1 |
| 3262 | Early | 01_039_1 |
| 3306 | Early | 01_044_1 |
| 3336 | Late | 16_017_1 |
| 3344 | Late | 06_012_1 |
| 3382 | Early | 01_075_1 |
| 3402 | Early | 06_043_1 |
| 3410 | Early | 06_002_1 |
| 3412 | Unknown | 11_050_1 |
| 3413 | Early | 01_008_1 |
| 3421 | Early | 06_010_1 |
| 3423 | Early | 01_066_1 |
| 3435 | Unknown | 11_044_1 |
| 3437 | Early | 11_003_1 |
| 3438 | Unknown | 08_001_1 |
| 3444 | Early | 11_047_1 |
| 3470 | Late | 01_021_1 |
| 3481 | Unknown | 01_025_1 |
| 3508 | Early | 01_001_1 |
| 3521 | Early | 16_006_1 |
| 3526 | Early | 01_034_1 |
| 3535 | Early | 01_062_1 |
| 3553 | Unknown | 01_082_1 |
| 3563 | Early | 06_040_1 |
| 3592 | Early | 11_005_1 |
| 3600 | Unknown | 14_001_1 |
| 3609 | Early | 14_012_1 |
| 3646 | Early | 11_030_1 |
| 3655 | Early | 07_012_1 |
| 3670 | Unknown | 06_030_1 |
| 3678 | Early | 01_052_1 |
| 3686 | Unknown | 01_080_1 |
| 3698 | Early | 01_029_1 |
| 3701 | Early | 01_060_1 |
| 3704 | Unknown | 01_049_1 |
| 3727 | Early | 12_007_1 |
| 3739 | Early | 11_008_1 |
| 3763 | Unknown | 01_061_1 |
| 3764 | Early | 06_020_1 |
| 3767 | Unknown | 12_013_1 |
| 3780 | Early | 12_009_1 |
| 3792 | Early | 12_003_1 |
| 3798 | Unknown | 01_089_1 |
| 3801 | Early | 07_011_1 |
| 3806 | Unknown | 04_013_1 |
| 3821 | Early | 16_016_1 |
| 3850 | Early | 11_056_1 |
| 3854 | Early | 14_013_1 |
| 3874 | Early | 01_093_1 |
| 3882 | Unknown | 12_006_1 |
| 3903 | Early | 07_007_1 |
| 3920 | Early | 11_026_1 |
| 3943 | Early | 11_012_1 |
| 3945 | Early | 11_033_1 |
| 3953 | Early | 11_042_1 |
| 3955 | Unknown | 04_005_1 |
| 3962 | Unknown | 12_013_1 second sample |
| 3969 | Unknown | 14_006_1 |
| 3973 | Early | 13_005_1 |
| 3978 | Unknown | 03_001_1 |
| 3993 | Unknown | 02_005_1 |
| 4001 | Early | 06_016_1 |
| 4009 | Unknown | 16_009_1 |
| 4014 | Late | 04_003_1 |
| 4034 | Early | 12_008_1 |
| 4042 | Early | 06_013_1 |
| 4049 | Unknown | 06_009_1 |
| 4053 | Early | 01_007_1 |
| 4055 | Early | 11_039_1 |
| 4062 | Unknown | 12_001_1 |
| 4076 | Late | 01_035_1 |
| 4083 | Early | 11_015_1 |
| 4120 | Early | 11_053_1 |
| 4136 | Late | 07_008_1 |
| 4161 | Unknown | 16_011_1 |
| 4200 | Unknown | 06_022_1 |
| 4202 | Unknown | 07_006_1 |
| 4227 | Unknown | 01_030_1 |
| 4308 | Early | 01_067_1 |
| 4331 | Sample not available for MS generation | 01_040_1 repeat(original sample # not listed on pdf document) |
| 4345 | Late | 11_024_1 |
| 4349 | Unknown | 13_004_1 |
| 4353 | Late | 11_051_1 |
| 4364 | Early | 11_029_1 |
| 4381 | Early | 01_015_1 |
| 4385 | Early | 01_083_1 |
| 4419 | Unknown | 11_001_1 |
| 4426 | Early | 01_069_1 |
| 4431 | Unknown | 01_019_1 |
| 4445 | Early | 11_041_1 |
| 4446 | Unknown | 01_032_1 |
| 4455 | Early | 11_028_1 |
| 4462 | Early | 01_090_1 |
| 4499 | Early | 02_002_1 |
| 4504 | Early | 01_073_1 |
| 4505 | Unknown | 16_015_1 |
| 4509 | Early | 11_016_1 |
| 4510 | Late | 01_033_1 |
| 4515 | Early | 12_002_1 |
| 4540 | Early | 11_034_1 |
| 4562 | Early | 01_014_1 |
| 4564 | Early | 04_002_1 |
| 4607 | Unknown | 01_047_1 |
| 4618 | Early | 06_042_1 |
| 4634 | Early | 01_053_1 |
| 4667 | Unknown | 13_003_1 |
| 4683 | Early | 14_010_1 |
| 4694 | Late | 06_024_1 |
| 4697 | Early | 06_038_1 |
| 4699 | Early | 11_037_1 |
| 4713 | Late | 01_016_1 |
| 4730 | Early | 01_028_1 |
| 4753 | Early | 06_015_1 |
| 4770 | Early | 06_034_1 |
| 4780 | Late | 06_018_1 |
| 4783 | Late | 01_027_1 |
| 4786 | Unknown | 04_010_1 |
| 4803 | Early | 01_026_1 |
| 4826 | Early | 01_006_1 |
| 4851 | Early | 01_086_1 |
| 4873 | Unknown | 12_012_1 |
| 4876 | Early | 11_022_1 |
| 4880 | Early | 01_077_1 |
| 4900 | Early | 01_020_1 |
| 4910 | Early | 06_031_1 |
| 4936 | Early | 01_088_1 |
| 4961 | Late | 01_072_1 |
| 4976 | Early | 01_037_1 |
| 4986 | Late | 15_002_1 |
| 5007 | Unknown | 01_079_1 |
| 5072 | Unknown | 11_035_1 |
| 5079 | Early | 03_004_1 |
| 5090 | Early | 11_049_1 |

APPENDIX G-continued

VS2.0 Classifications returned for PROSE samples

| Blinded ID | VS2.0 CLASSIFICATION | PROSE Sample # |
|---|---|---|
| 5091 | Early | 01_087_1 |
| 5101 | Unknown | 01_063_1 |
| 5134 | Early | 12_010_1 |
| 5158 | Late | 07_014_1 |
| 5195 | Early | 01_080_1 second sample |
| 5196 | Early | 16_014_1 |
| 5214 | Unknown | 14_009_1 |
| 5228 | Unknown | 11_036_1 |
| 5239 | Early | 04_009_1 |
| 5250 | Late | 11_021_1 |
| 5254 | Early | 06_026_1 |
| 5292 | Early | 11_004_1 |
| 5295 | Early | 07_005_1 |
| 5307 | Early | 06_025_1 |
| 5330 | Late | 11_045_1 |
| 5336 | Unknown | 10_003_1 |
| 5351 | Early | 06_033_1 |
| 5352 | Late | 16_010_1 |
| 5358 | Unknown | 13_001_1 |
| 5362 | Late | 04_004_1 |
| 5374 | Unknown | 02_003_1 |
| 5391 | Early | 01_064_1 |
| 5395 | Early | 06_032_1 |
| 5401 | Late | 01_092_1 |
| 5411 | Early | 13_002_1 |
| 5424 | Late | 01_043_1 |
| 5431 | Unknown | 02_004_1 |
| 5440 | Early | 06_029_1 |
| 5443 | Unknown | 12_011_1 |
| 5444 | Early | 11_006_1 |
| 5447 | Unknown | 01_003_1 |
| 5448 | Unknown | 04_006_1 |
| 5456 | Early | 14_011_1 |
| 5466 | Early | 14_004_1 |
| 5497 | Unknown | 16_003_1 |
| 5505 | Early | 01_002_1 |
| 5507 | Early | 12_005_1 |
| 5512 | Late | 01_070_1 |
| 5567 | Unknown | 02_001_1 |
| 5573 | Early | 01_022_1 |
| 5583 | Early | 04_012_1 |
| 5587 | Early | 12_004_1 |
| 5594 | Early | 06_041_1 |
| 5638 | Early | 11_023_1 |
| 5658 | Early | 01_011_1 |
| 5663 | Early | 01_094_1 |
| 5671 | Early | 11_031_1 |
| 5672 | Early | 01_056_1 |
| 5673 | Early | 01_004_1 |
| 5680 | Late | 14_003_1 |
| 5713 | Early | 01_009_1 |
| 5714 | Late | 06_005_1 |
| 5721 | Unknown | 01_071_1 |
| 5724 | Early | 08_002_1 |
| 5725 | Unknown | 06_019_1 |
| 5747 | Early | 01_065_1 |
| 5755 | Early | 01_042_1 |
| 5767 | Unknown | 07_004_1 |
| 5791 | Early | 06_037_1 |
| 5801 | Late | 11_018_1 |
| 5813 | Early | 11_027_1 |
| 5820 | Late | 01_018_1 |
| 5842 | Late | 03_005_1 |
| 5847 | Unknown | 11_054_1 |
| 5869 | Early | 14_005_1 |
| 5874 | Early | 15_001_1 |
| 5910 | Unknown | 01_091_1 |
| 5911 | Early | 06_035_1 |
| 5913 | Early | 03_002_1 |
| 5935 | Early | 16_018_1 |
| 5963 | Early | 06_039_1 |
| 5970 | Late | 01_054_1 |
| 5975 | Early | 01_046_1 |
| 5976 | Early | 01_085_1 |
| 5997 | Unknown | 14_002_1 |
| 6048 | Early | 01_017_1 |
| 6056 | Unknown | 16_007_1 |
| 6082 | Early | 11_014_1 |
| 6093 | Early | 07_001_1 |
| 6098 | Late | 11_017_1 |
| 6105 | Unknown | 16_002_1 |
| 6122 | Early | 06_010_1 second sample |
| 6130 | Early | 14_007_1 |
| 6140 | Unknown | 07_003_1 |
| 6156 | Late | 11_011_1 |
| 6161 | Early | 01_068_1 |
| 6182 | Early | 11_020_1 |
| 6193 | Unknown | 16_008_1 |
| 6203 | Early | 11_013_1 |
| 6235 | Unknown | 11_010_1 |
| 6260 | Early | 01_045_1 |
| 6270 | Early | 11_052_1 |
| 6278 | Early | 06_008_1 |
| 6281 | Early | 04_008_1 |
| 6282 | Unknown | 06_022_1 |
| 6295 | Early | 11_009_1 |
| 6296 | Early | 01_041_1 |
| 6297 | Unknown | 01_081_1 |
| 6299 | Early | 14_014_1 |
| 6321 | Early | 11_057_1 |
| 6336 | Late | 01_023_1 |
| 6349 | Late | 10_001_1 |
| 6361 | Unknown | 03_003_1 |
| 6390 | Early | 01_078_1 |
| 6398 | Unknown | 06_001_1 |
| 6419 | Late | 01_044_1 second sample |
| 6424 | Early | 06_023_1 |
| 6438 | Unknown | 16_001_1 |
| 6439 | Early | 01_036_1 |
| 6442 | Early | 10_004_1 |
| 6476 | Early | 01_084_1 |
| 6487 | Sample not available for MS generation | 11_048_1 |
| 6492 | Late | 01_057_1 |
| 6572 | Unknown | 13_006_1 |
| 6585 | Early | 01_076_1 |
| 6604 | Early | 11_002_1 |
| 6622 | Early | 01_031_1 |
| 6625 | Early | 06_011_1 |
| 6626 | Early | 06_003_1 |
| 6667 | Unknown | 11_025_1 |
| 6712 | Early | 01_038_1 |
| 6718 | Early | 07_013_1 |
| 6729 | Early | 06_036_1 |
| 6737 | Early | 06_006_1 |
| 6741 | Early | 16_004_1 |
| 6752 | Early | 11_019_1 |
| 6761 | Late | 06_027_1 |
| 6770 | Early | 11_007_1 |
| 6795 | Unknown | 11_038_1 |
| 6797 | Early | 01_058_1 |
| 6824 | Unknown | 04_007_1 |
| 6827 | Early | 06_007_1 |
| 6847 | Early | 04_011_1 |
| 6854 | Early | 07_002_1 |
| 6886 | Unknown | 01_012_1 |
| 6887 | Late | 01_051_1 |
| 6932 | Early | 01_005_1 |
| 6939 | Late | 14_008_1 |
| 6947 | Early | 11_032_1 |
| 6977 | Early | 07_009_1 |
| 6981 | Unknown | 06_028_1 |
| 6982 | Early | 13_007_1 |
| 6992 | Late | 11_040_1 |
| 6998 | Unknown | 06_017_1 |

APPENDIX H

Details of instruments for spectral acquisition

| Run | Dates | Ser. No. | Qualification Date |
|---|---|---|---|
| 140131_ItalianABC | Feb. 3, 2014-Feb. 4, 2014 | 260 | Jan. 30, 2014 NRS Jan. 27, 2014 RuO |
| 140225_ItalianABC | Feb. 25, 2014 | 260 | Feb. 25, 2014 NRS |
| 140130_Furb_PROSE*[2] | Jan. 30, 2014-Jan. 31, 2014 | 260 | Jan. 30, 2014 NRS |
| 140115_PROSE | Jan. 15, 2014-Jan. 17, 2014 | 258 | Dec. 11, 2013* |
| 131118_ItalianABC | Nov. 18, 2013-Nov. 19, 2013 | 258 | Nov. 12, 2013 RuO |

*This was a quick concordance check two samples had a spot fail to acquire, but if you dropped these two samples it was concordant.
*[2]This run was done on the same plate as the 140115_PROSE run from instrument 258

What is claimed is:

1. A method for predicting in advance whether a non-small-cell lung cancer (NSCLC) patient is a member of a class of cancer patients likely to obtain greater benefit from a treatment for the NSCLC in the form of administration of an epidermal growth factor receptor inhibitor (EGFR-I) as compared to chemotherapy, comprising the steps of:
    (a) storing in a computer readable medium a training set comprising class-labeled mass spectral data obtained from a multitude of cancer patients who are determined by mass spectrometry of a blood-based sample to be members of a class of patients that are predicted to obtain overall survival benefit from an EGFR-I in treatment of the cancer, such class of patients further divided into two sub-classes:
        1) those patients which exhibited early progression of disease after administration of the EGFR-I in treatment of cancer, mass spectral data of such patients having a class label of "early" or the equivalent; and
        2) those patients which exhibited late progression of disease after administration of an EGFR-I in treatment of cancer, mass spectral data of such patients having a class label of "late" or the equivalent;
    (b) providing a blood-based sample from the NSCLC patient to a mass spectrometer and conducting mass spectrometry on the blood-based sample and thereby generating a mass spectrum for the blood-based sample;
    (c) conducting pre-defined pre-processing steps on the mass spectrum obtained in step b) with the aid of a programmed computer;
    (d) obtaining integrated intensity feature values of selected features in said mass spectrum at a plurality of pre-defined m/z ranges after the pre-processing steps on the mass spectrum recited in step c) have been performed; and
    (e) executing in the programmed computer a classifier including a classification algorithm comparing the integrated intensity values obtained in step (d) with the training set stored in step (a) and responsively generating a class label for the blood-based sample,
    wherein if the class label generated in step (e) is "late" or the equivalent for the mass spectrum of the blood based sample, the patient is identified as being likely to obtain greater benefit from the EGFR-I as compared to chemotherapy in treatment of the cancer.

2. The method of claim 1, wherein the EGFR-I comprises gefitinib, erlotinib, a second generation EGFR-I such as dacominitib, affatinib, or the equivalent.

3. The method of claim 1, wherein the classifier comprises a combination of filtered mini-classifiers after dropout regularization and logistical training (CMC/D classifier).

4. The method of claim 1, further comprising the steps of:
    conducting mass spectrometry of a reference sample and obtaining a set of reference sample feature values from a mass spectrum of the reference sample;
    checking the reference sample feature values for concordance with a predefined set of feature values;
    defining a feature correction function for the mass spectrum of the sample from the reference sample feature values; and
    correcting the feature values of the mass spectrum of the blood-based sample in accordance with the feature correction function.

5. The method of claim 1, further comprising the steps of:
    a) storing a set of feature dependent noise characteristics;
    b) generating a set of noisy feature value realizations of the feature values of the mass spectrum of the blood-based sample;
    c) applying the classifier to the noisy feature value realizations and collating the results of the applying step;
    d) generating statistical data on the results collated in step c) and
    e) using the statistical data generated in step d) in conjunction with the class label generated at step (e) of claim 1 to determine the class label for the mass spectrum of the blood-based sample.

6. The method of claim 1, further comprising the steps recited in claim 4 and the steps recited in claim 5.

7. The method of claim 1, wherein the training set comprises class-labeled mass spectra obtained from blood-based samples of a multitude of NSCLC patients.

8. The method of claim 1, wherein the classification algorithm comprises a k-nearest neighbor classification algorithm.

9. The method of claim 1, further comprising a preliminary step of determining whether the patient is a member of a class of a class of patients having a predicted overall survival benefit from treatment of the NSCLC by administration of an EGFR-I, and then conducting steps b)-e) of claim 1 on the sample from the patient.

10. The method of claim 3, wherein the classifier compares feature values of at least 50 features in the mass spectrum of the sample with feature values of the same at least 50 features of the training set.

11. The method of any of claim 10, wherein the feature values encompass the features listed in Appendix B.

12. The method of claim 3, wherein the CMC/D classifier is in the form of a multitude of final classifiers generated as a result of splitting a classifier development sample set into a multitude of training and test sets.

13. The method of claim 12, wherein the multitude of final classifiers comprises greater than 100 final classifiers resulting for greater than 100 splits of the development sample set into training and test sets.

14. A system for processing a blood-based sample of a non-small-cell lung cancer (NSCLC) patient to determine whether the patient is a member of a class of cancer patients likely to obtain greater benefit from a treatment for the NSCLC in the form of administration of an epidermal growth factor receptor inhibitor (EGFR-I) as compared to chemotherapy in treatment for the NSCLC, comprising, in combination:
    (a) a mass spectrometer generating a mass spectrum of the blood-based sample; and
    (b) a programmed computer including a processing unit and a memory storing mass spectral data from the mass spectrometer, the memory further storing:

1) non-transient data in the form of a training set comprising class-labeled mass spectral data obtained from a multitude of cancer patients who are members of a class of patients who are determined by mass spectrometry of a blood-based sample to be predicted to obtain overall survival benefit from an EGFR-I in treatment of the cancer, such class of patients further divided into two sub-classes:
   i) those patients which exhibited early progression of disease after administration of the EGFR-I in treatment of cancer, mass spectral data of such patients having a class label of "early" or the equivalent; and
   ii) those patients which exhibited late progression of disease after administration of an EGFR-I in treatment of cancer, mass spectral data of such patients having a class label of "late" or the equivalent;
2) program code for implementing a classifier in the form of a combination of filtered mini-classifiers after dropout regularization and logistical training (CMC/D classifier) on the training set;
3) program code for conducting pre-defined pre-processing steps on the mass spectrum stored in 1), obtaining integrated intensity feature values of selected features in said mass spectrum at a plurality of predefined m/z ranges after the pre-processing steps on the mass spectrum have been performed; and
4) program code applying the CMC/D classifier to the integrated intensity values obtained in 3) and the training set and responsively generating a class label for the blood-based sample,
wherein if the class label generated by program code 4) is "late" or the equivalent for the blood based sample the patient is identified as being likely to obtain greater benefit from the EGFR-I as compared to chemotherapy in treatment of the cancer.

15. The system of claim 14, wherein the EGFR-I comprises gefitinib, erlotinib, a second-generation EGFR-I such as dacomitinb or affatinib, or the equivalent.

16. The system of claim 14, wherein the system further comprises a blood-based reference sample, wherein the mass spectrometer conducts mass spectrometry of the reference sample, and wherein the memory further stores program code for:
   a. obtaining a set of reference sample feature values from a mass spectrum of the reference sample;
   b. checking the reference sample feature values for concordance with a predefined set of feature values;
   c. defining a feature correction function for the mass spectrum of the sample from the reference sample feature values; and
   d. correcting the feature values of the mass spectrum of the blood-based sample in accordance with the feature correction function.

17. The system of claim 14, wherein:
a) the memory stores data representing a set of feature dependent noise characteristics; and
b) the memory stores program code for:
i) generating a set of noisy feature value realizations of the feature values of the mass spectrum of the blood-based sample;
ii) applying the classifier to the noisy feature value realizations and collating the results of the applying step;
iii) generating statistical data on the results collated in step ii) and
iv) using the statistical data generated in iii) in conjunction with the class label generated by the program code 4) of claim 14 to determine the class label for the mass spectrum of the blood-based sample.

18. The system of claim 14, wherein the training set comprises class-labeled mass spectra obtained from blood-based samples of a multitude of NSCLC patients.

19. The system of claim 14, wherein the CMC/D classifier implements a K-nearest neighbor classification algorithm operating on the feature values of the test sample and feature values in the training set.

20. The system of claim 14, wherein the CMC/D classifier compares feature values of at least 50 features in the mass spectrum of the sample with feature values of the same at least 50 features of the training set.

21. The system of claim 20, wherein the feature values include the features listed in Appendix B.

22. The system of claim 14, wherein the CMC/D classifier is in the form of a multitude of final classifiers generated as a result of splitting a classifier development sample set into a multitude of training and test sets.

23. The system of claim 22, wherein the multitude of final classifiers comprises greater than 100 final classifiers resulting for greater than 100 splits of the development sample set into training and test sets.

24. Apparatus for use in classifying a sample, comprising:
a computer memory storing non-transient data in the form of a training set comprising class-labeled mass spectral data obtained from a multitude of cancer patients who are members of a class of patients that are predicted to obtain overall survival benefit from an EGFR-I in treatment of the cancer, such class of patients further divided into two sub-classes:
1) those patients which exhibited early progression of disease after administration of the EGFR-I in treatment of cancer, mass spectral data of such patients having a class label of "early" or the equivalent; and
2) those patients which exhibited late progression of disease after administration of an EGFR-I in treatment of cancer, such patients having a class label of "late" or the equivalent.

25. The apparatus of claim 24, wherein:
the memory further stores code for execution by a computer processing unit implementing a classifier in the form of a combination of filtered mini-classifiers after dropout regularization and logistical training (CMC/D classifier) on said training set.

26. The apparatus of claim 25, wherein:
the memory further stores storing mass spectral data from a blood-based sample for classification by the CMC/D classifier.

27. The apparatus of claim 26,
wherein the memory further stores a routine defining a feature correction function for feature values obtained from the mass spectral data, the feature correction function derived from mass spectral data obtained from a reference sample.

28. The apparatus of claim 27, wherein:
a) the memory stores data representing a set of feature dependent noise characteristics obtained from the reference sample; and
b) the memory stores program code for:
ii) generating a set of noisy feature value realizations of the feature values of the mass spectrum of the blood-based sample;
ii) applying the classifier to the noisy feature value realizations and collating the results of the applying step;
iii) generating statistical data on the results collated in step ii) and iv) using the statistical data generated in iii) to determine a class label for the mass spectrum of the blood-based sample.

29. A method of treating a NSCLC patient, comprising the steps of:
administering an EGFR-I to the NSCLC patient, wherein the patient is predicted to benefit more from the EGFR-I as compared to chemotherapy by executing in a programmed computer a classifier comparing mass spectral data produced by a mass spectrometer from a blood-based sample of the NSCLC patient to a training set comprising class-labeled mass spectral data obtained from a multitude of cancer patients who are determined by mass spectrometry of a blood-based sample to be members of a class of patients that are predicted to obtain overall survival benefit from an EGFR-I in treatment of the cancer, such class of patients further divided into two sub-classes:
  1) those patients which exhibited early progression of disease after administration of the EGFR-I in treatment of cancer, mass spectral data of such patients having a class label of "early" or the equivalent; and
  2) those patients which exhibited late progression of disease after administration of an EGFR-I in treatment of cancer, mass spectral data of such patients having a class label of "late" or the equivalent.

30. The method of claim 29, wherein the programmed computer implements a classifier in the form of a combination of filtered mini-classifiers after dropout regularization and logistical training (CMC/D classifier).

* * * * *